Figure 1:
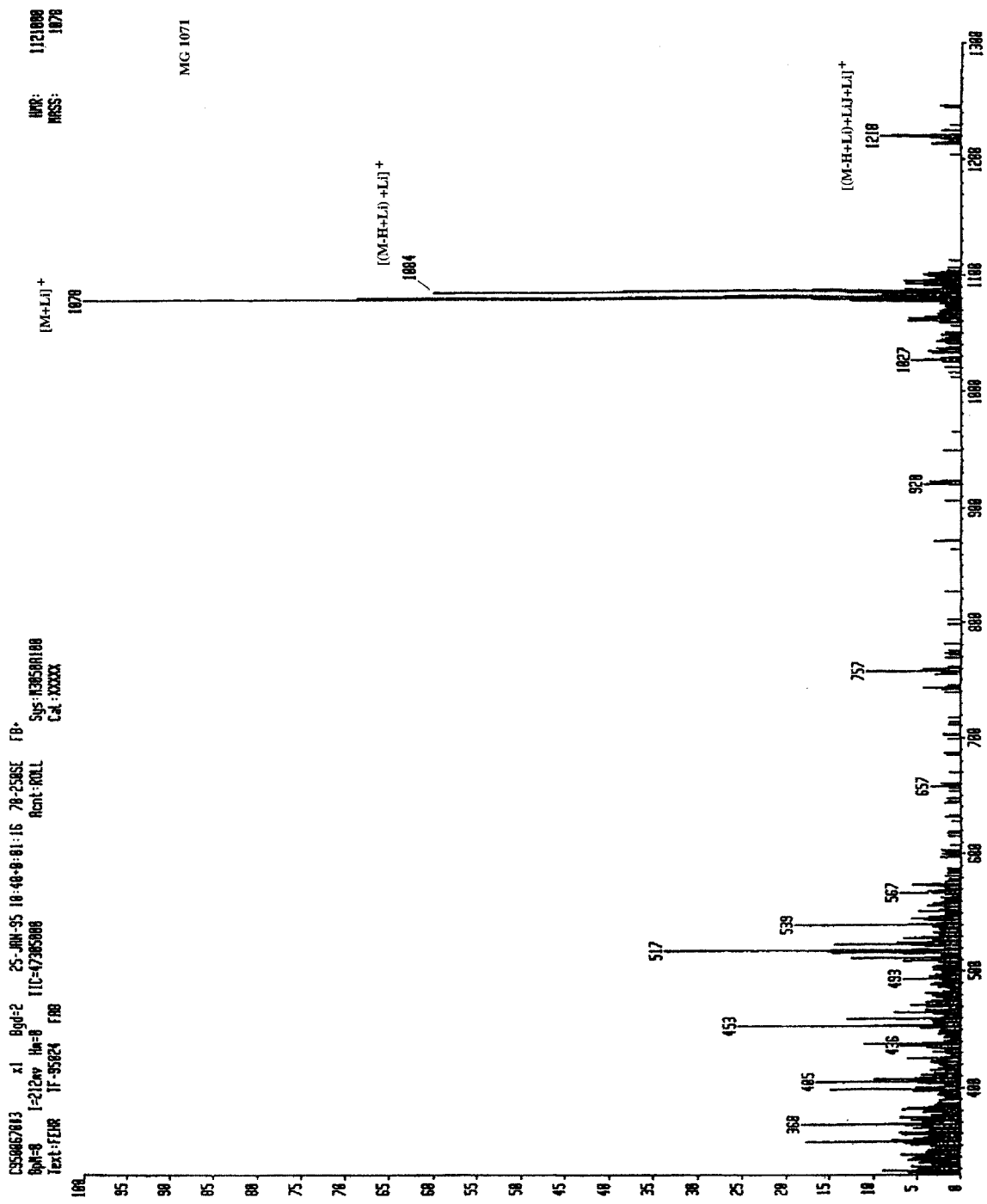

United States Patent [19]
Fehr et al.

[11] Patent Number: 6,124,453
[45] Date of Patent: Sep. 26, 2000

[54] MACROLIDES

[75] Inventors: Theodor Fehr, Dornach; Lukas Oberer, Tenniken, both of Switzerland; Valerie Quesniaux Ryffel, Huningue, France; Jean-Jacques Sanglier, Allschwil, Switzerland; Walter Schuler, Grenzach-Wyhlen, Germany

[73] Assignee: Novartis AG, Basel, Switzerland

[21] Appl. No.: 08/774,114

[22] Filed: Dec. 24, 1996

Related U.S. Application Data

[63] Continuation-in-part of application No. 08/701,604, Aug. 22, 1996, abandoned, and application No. PCT/EP96/02952, Jul. 4, 1996.

[30] Foreign Application Priority Data

Jul. 4, 1995 [DE] Germany .................... 9513596
Jul. 28, 1995 [DE] Germany .................... 9515495

[51] Int. Cl.[7] .................... C07D 267/00; C07D 31/33
[52] U.S. Cl. .................... 540/456; 540/453; 540/454; 540/455; 514/183
[58] Field of Search .................... 540/456; 514/183, 514/454, 455

[56] References Cited

U.S. PATENT DOCUMENTS

| | | | |
|---|---|---|---|
| 5,284,877 | 2/1994 | Organ et al. | 518/183 |
| 5,344,925 | 9/1994 | Goulet et al. | 540/456 |
| 5,346,893 | 9/1994 | Failli et al. | 314/183 |

FOREIGN PATENT DOCUMENTS

| | | |
|---|---|---|
| 9506649 | 3/1995 | WIPO . |
| 9515328 | 6/1995 | WIPO . |

OTHER PUBLICATIONS

Nakagawa et al., (CA 113:74347, abstract of Agric. Biol. Chem. (1990), 54(3), pp. 791–794, 1990.
Takeuchi et al., (CA 116:104496, abstract of JP 03240791), 1991.

*Primary Examiner*—Jose' G. Dees
*Assistant Examiner*—Sabiha N. Qazi
*Attorney, Agent, or Firm*—Carol A. Loeschorn

[57] ABSTRACT

A novel class of macrolides in which
i) positions 2 to 6 inclusive of the macrocyclic ring are provided by a piperidazinyl carboxylic acid residue; and/or
ii) positions 7 to 9 inclusive of the macrocyclic ring are provided by an aromatic α-amino acid residue; and/or
iii) positions 10 to 12 inclusive of the macrocyclic ring are provided by an aliphatic α-amino acid residue, preferably comprising two, or especially all three of the characteristic structural features i), ii) and iii), more especially a compound of formula IX

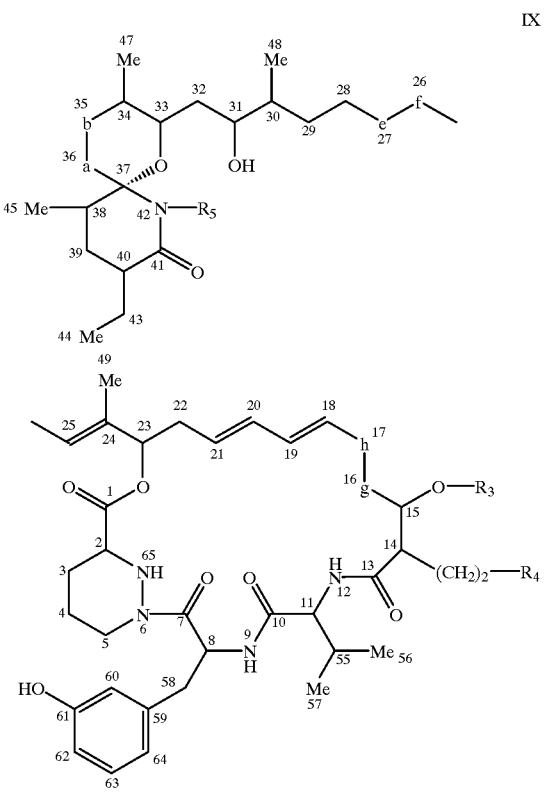

is provided having immunosuppressant and antinflammatory properties and protected and ring-open forms thereof.

9 Claims, 21 Drawing Sheets

MACROLIDES

This application is a continuation-in-part of U.S. patent application Ser. No. 08/701,604 filed on the Aug. 22, 1996 now abandoned, which in turn is a continuation-in-part of international patent application PCT/EP 96/02952 filed on Jul. 4, 1996, in respect of the designation of the United States of America contained in the said international patent application.

The present invention relates to a novel class of macrolides having valuable pharmaceutical and related activity. For convenience compounds of this novel macrolide class are referred to herein collectively as "Sanglifehrins".

The first of the Sanglifehrins were isolated from actinomycete fermentation broths. These are the Sanglifehrins A through D of formulae

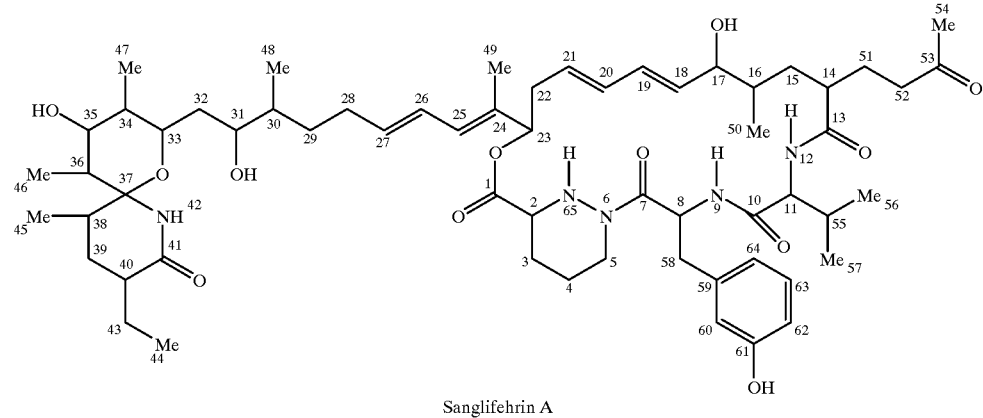

Sanglifehrin A

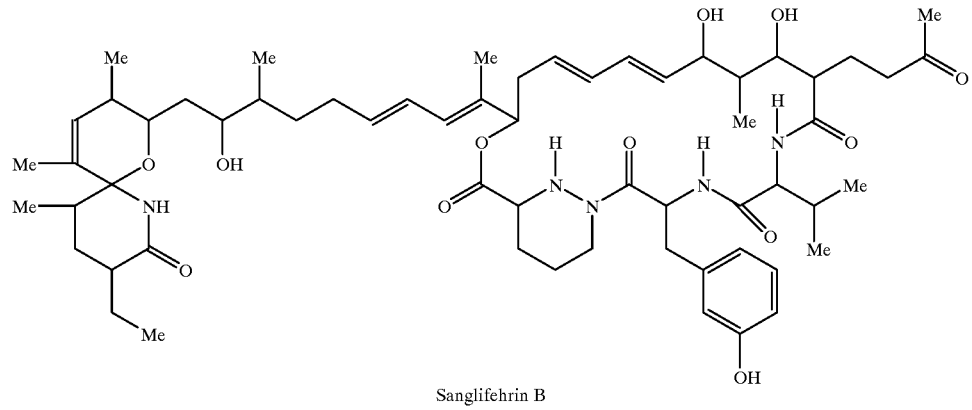

Sanglifehrin B

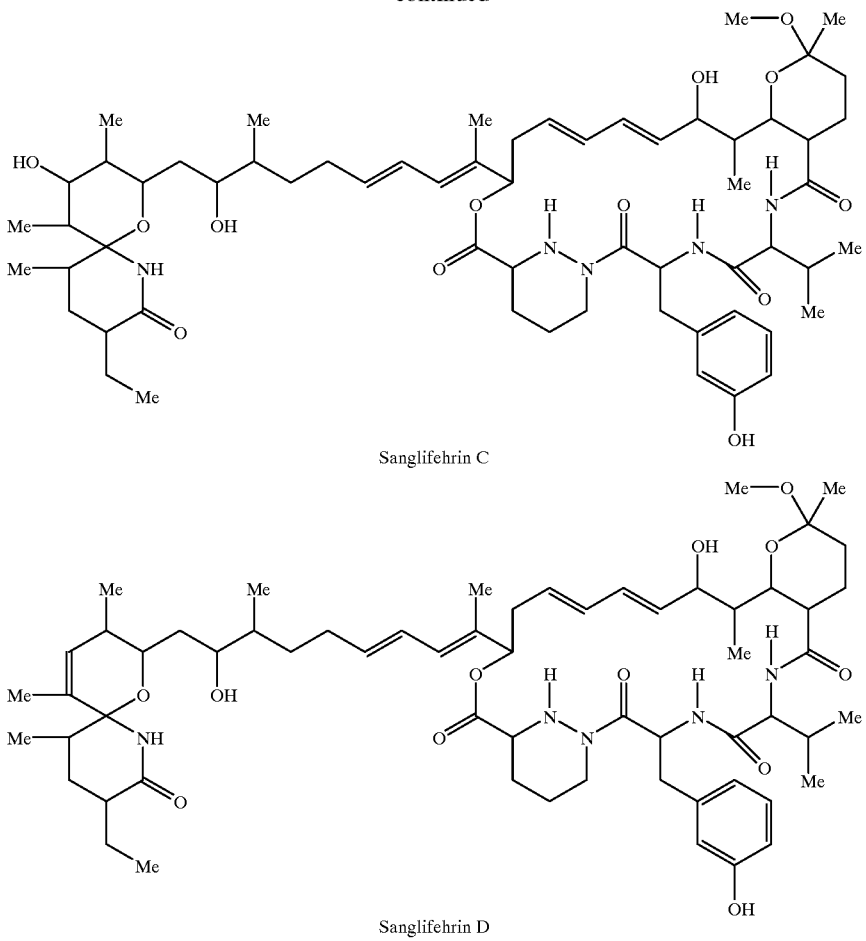

Sanglifehrin C

Sanglifehrin D

As can be seen, the macrocyclic ring of Sanglifehrins A to D is of entirely novel structure characterised in that i) positions 1 to 6 comprise a 3-carboxypiperidazinyl carboxylic acid residue, ii) positions 7 to 9 an aromatic α-amino acid residue, and iii) positions 10 to 12 an aliphatic α-amino acid residue. The remainder of the macrocyclic ring is comprised by an hydroxy carboxylic acid residue, providing, in the case of Sanglifehrins A to D a further 11 carbon atoms in the primary macrocyclic ring.

In accordance with conventional practice in macrolide chemistry the atoms of the Sanglifehrin primary macrocyclic ring are numbered as indicated above for Sanglifehrin A, starting with the carbon atom of the carbonyl group of the macrocyclic lactone linkage as position 1.

Sanglifehrins A to D are also characterised by the presence of a novel bicyclic Spiro system attached at the 23 position of the macrocyclic ring via a hydrocarbyl linker group.

Sanglifehrins A to D may be subjected to extensive chemical manipulation to obtain yet further macrolides of the Sanglifehrin class. Such manipulations include cleavage of the macrocyclic ring, in particular at the lactone oxygroup, cleavage of the linker group between the macrolide and Spiro ring systems, and manipulation, e.g. protection, derivatization or other chemical modification of substituent groupings; for example, as hereinafter described. Further means of modification will be apparent to those skilled in the art.

In accordance with the invention it has been found that Sanglifehrins, in particular those in which the Spiro ring system is present, as in the case of Sanglifehrins A to D, have a characteristic and entirely novel profile in terms of their biological activity. In particular they have been found to exhibit the combination of activities as hereinafter described.

The Sanglifehrins may be seen as providing an exciting and novel class of immunosuppressant and antiinflammatory compounds. In particular the Sanglifehrins have an activity profile that differs from that of previously known immunosuppressant and antiinflammatory compounds such as cyclosporins and macrolides, e.g. of the rpamycin and FK 506 class, indicating that the Sanglifehrins have a different mode of action than such previous compounds. Thus the Sanglifehrins provide a novel category of drug substance both in terms of structure and activity which may be anticipated to materially extend the bounds of immunosuppressive and/or antiinflammatory therapy; for example, to avoid or reduce undesirable side effects of previous immunosuppressive and antiinflammatory therapies and/or to improve or extend such therapy to new disease areas or new patient categories.

Sanglifehrins, e.g. in which the macrolide ring is in ring-opened form, in which the 26 and 27 positions in the hydrocarbyl linker between the macrolide and spiro ring systems are both hydroxy substituted, or in which the spiro residue attached to the macrocyclic ring has been cleaved or truncated, generally lack some or all of the combination of Sanglifehrin characteristic activities. For example, Sanglifehrins in which the spiro residue is cleaved typically possess cyclophilin binding activity but do not possess significant immunosuppressive activity. As will be apparent to those skilled in the art, however, such compounds provide valuable components, intermediates or key building blocks for the preparation of further novel Sanglifehrins, and hence further extend the therapeutic potential of the Sanglifehrin class.

In that its presence appears material to the biological activity, e.g. of the Sanglifehrins A to D, the bicyclic spiro system may also be viewed as providing a structural component with key biological significance, useful as a structural component for further derivatization or modification both in relation to the production of further Sanglifehrins or for application in the derivatisation or modification of other drug substances for example, to modify the activity of other immunosuppressive drug substances of the macrolide class.

As indicated, the Sanglifehrins represent a novel class of macrolide compounds of entirely novel and wholly characteristic structure.

Accordingly in a first aspect the invention provides:

a macrolide in which i) positions 2 to 6 inclusive of the macrocyclic ring are provided by a piperidazinyl carboxylic acid residue; and/or ii) positions 7 to 9 inclusive of the macrocyclic ring are provided by an aromatic α-amino acid residue; and/or iii) positions 10 to 12 inclusive of the macrocyclic ring are provided by an aliphatic α-amino acid residue, in free or protected form, or a salt thereof.

Suitably the macrolides of the invention comprise two, especially all three of the characteristic structural features i), ii) and iii).

The piperidazinyl carboxylic acid residue is suitably a 1,2-piperidazin-3-carboxy-1-yl residue of which the carboxy moiety occupies the 1-position, and the 1-nitrogen atom the 6-position of the macrocyclic ring, e.g. a residue of formula I

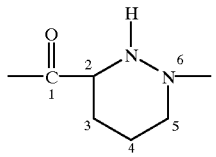

wherein the assigned numbers represent the position of the atoms of the residue in the macrocyclic ring. This residue may be ring substituted or unsubstituted. Suitably it is unsubstituted.

The carboxy moiety of the aromatic α-amino acid residue suitably occupies the 7-position of the macrocyclic ring, and the α-amino moiety the 9-position. Suitably the aromatic α-amino acid is a phenylalanine, especially 3-OH-phenylalanine, residue in free, protected or activated form.

The carboxy moiety of the aliphatic α-amino acid residue suitably occupies the 10-position of the macrocyclic ring, and the α-amino moiety the 12-position. Suitably the aliphatic α-amino acid residue is a valine residue in free, protected or activated form.

The remainder of the macrocyclic ring suitably comprises a hydroxy carboxylic acid residue, the oxy-moiety of which completes the macrocyclic lactone linkage and the carbonyl moiety of which forms an amide linkage with the α-amino group at position 12 of of the macrocyclic ring. The said hydroxy carboxylic acid residue suitably has a chain length of from 6 to 20, more suitably 11 carbon atoms. It may be substituted or unsubstituted and/or contain one or more unsaturated linkages in particular cumulative double bonds along its length. More suitably the remainder of the macrocyclic ring comprises a 11-oxy-undecanoyl-11-yl, especially 11-oxy-undeca-6,8-dienoyl-11-yl, residue optionally substituted, e.g. in the 2, 3, 4 and/or 5 positions. More suitably the said hydroxy carboxylic acid residue is a residue of formula II.

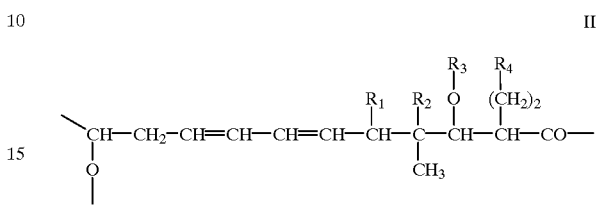

wherein $R_1$ is H, OH or represents an extra bond and $R_2$ is H or represents an extra bond;

$R_3$ is H, and $R_4$ is —CO—CH$_3$ or —CH(OH)—CH$_3$ or $R_3$ and $R_4$ together represent a structure of formula III

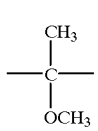

in free or protected form, or salt thereof.

Preferred macrolides in accordance with the invention are accordingly those comprising a macrocyclic ring of formula IV

wherein X, Y and Z are residues i), ii) and iii) as defined above and A is a hydroxy carboxylic acid residue as defined above in free or protected form, or salt thereof; in particular a macrocyclic ring of formula V

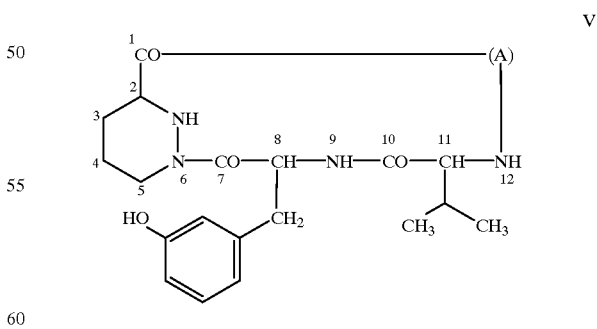

in free or protected form, or salt thereof

Generally in the Sanglifehrins, as in Sanglifehrins A to D, the macrocyclic ring is substituted at the carbon atom adjacent the oxy moiety of the lactone bridge. Typically this substituent comprises a 1-oxo-7-aza-spiro-{5.5}-undecan-8-one-2-yl residue, e.g. of the formula VI

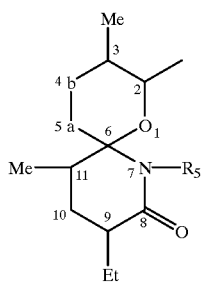

VI wherein

—a—b— is —(Me)C=CH— or —(Me)CH—CH(OH)— and

R, is H or Me (wherein Me and Et represent methyl and ethyl respectively) in free or protected form, or salt thereof linked to the macrolide ring via a linker comprising a linear sequence of from 6 to 11, typically 9, carbon atoms between the spiro residue and the macrolide ring.

The linker group may be substituted or unsubstituted and/or contain one or more unsaturated linkages in particular cumulative double bonds along its length. Suitably the linker group may be methyl substituted, e.g. by two methyl groups. Suitably the linker group may be further substituted by hydroxy, e.g. by three hydroxy substituents, and/or may be ethylenically unsaturated, e.g. contain two carbon-carbon double bonds. More suitably the linker group comprises a 1,7-dimethyl-nonan-9-yl, especially a 1,7-dimethyl-non-1-en-9-yl or a 1,7-dimethyl-nona-1,3-dien-9-yl, residue optionally substituted, e.g. in the 3, 4, and/or 8 position. Preferably the linker group is a group of formula VII

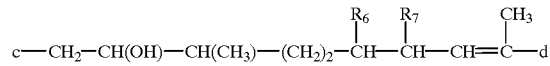

wherein c represents linkage to the spiro residue;

d represents linkage to the macrocyclic ring and $R_6$ and $R_7$ are each OH or together represent an additional bond, in free or protected form.

The linker group will generally be attached to the macrocyclic ring at the carbon atom immediately adjacent to the lactone oxy group, i.e. when the macrocyclic ring comprises an 11-oxy-undecanoyl-11-yl residue, at the 11 position of thereof.

Accordingly the invention provides compounds of formula VIII $$S—L—M \qquad \text{VIII}$$

wherein

S represents a spiro bicyclo residue as previously defined;

L represents a linker group as previously defined, and

M represents a macrolide ring as previously defined, in free or protected form, or salt thereof.

Particular compounds of the invention are those of formula IXa and IX

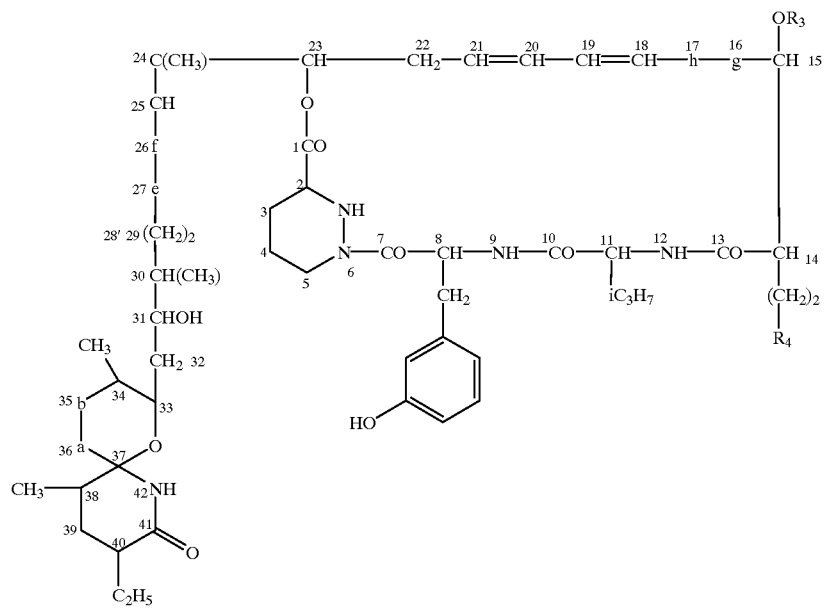

IXa

-continued

IX

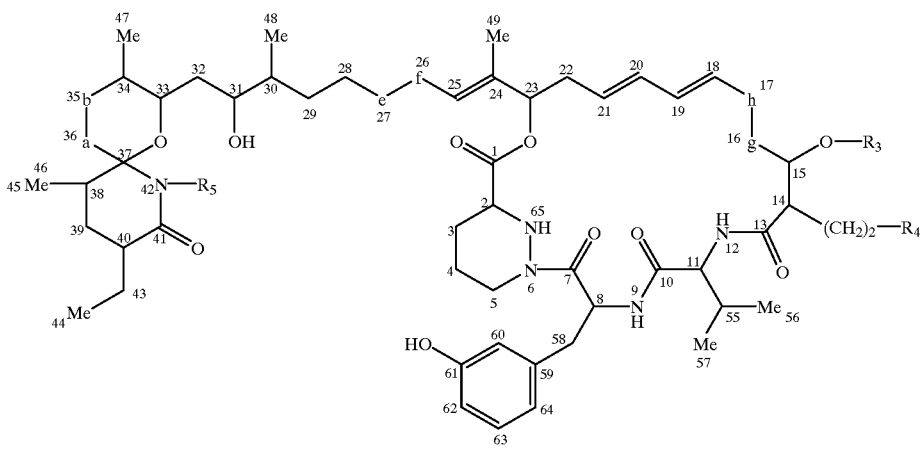

wherein

—a—b— is as defined above,

—e—f— is —CH(OH)—CH(OH)— or —CH=CH—;

—g—h— is as defined above for —a—b—, and $R_3$, $R_4$ and $R_5$ are as defined above, in free or protected form or salt thereof The compounds of formulae I to IX contain asymmetric carbon atoms and thus may exist in a number of epimeric forms. All of the possible epimers as well as diastereoisomeric mixtures thereof are encompassed in the invention. However, compounds of formulae VIII and IX in which the macrolide ring is in ring-closed form and which are of appropriate stereochemistry typically possess activities which are characteristics of Sanglifehrins, as herein referred to. Epimers which possess sanglifehrin characteristic activities are preferred. In general, e.g. for pharmaceutical use in accordance with the invention, epimers which possess sanglifehrin characteristic activities in pure or substantially pure form (i.e. free or substantially free of epimers which lack sanglifehrin characteristic activities), e.g. comprising at least 90%, e.g. at least 95% of active epimer (i.e. comprising less than 10%, e.g. less than 5% of inactive epimer) will be preferred.

Preferably the 3-carboxypiperidazinyl carboxylic acid residue i) at positions 1 to 6 of the macrocyclic ring has the following conformation:

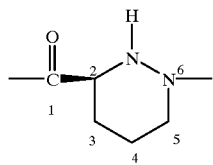

Preferably the aromatic amino acid ii) at positions 7 to 9 of the macrocyclic ring has the L configuration, e.g. is of configuration

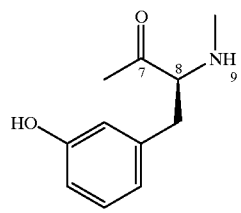

Preferably the aliphatic amino acid iii) at positions 10 to 12 of the macrocyclic ring has the L configuration, e.g. is of configuration

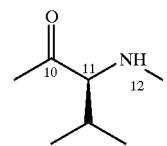

When the remainder of the macrocyclic ring comprises a residue of formula II, it preferably has the configuration

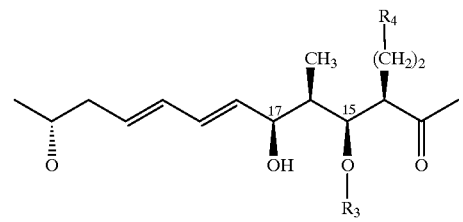

or

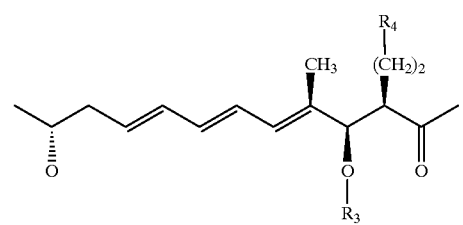

When R₃ and R₄ together represent

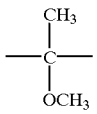

it preferably has the configuration

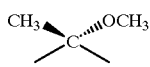

Preferably the 1-oxo-7-aza-spiro-{5.5}-undecan-8-one-2-yl residue has the configuration

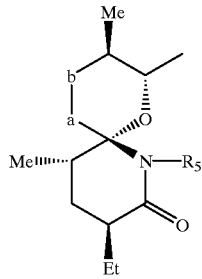

wherein when —a—b— is —(Me)CH—CH(OH)—, it preferably has the configuration

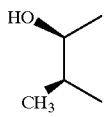

When the linker is of formula VII, it is preferably of configuration

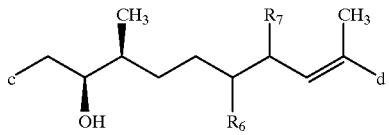

When R₆ and R₇ are each OH, the configuration at positions 26 and 27 is preferably either 26(S), 27(S) or 26(R), 27(R). When R₆ and R₇ together represent an additional bond, the configuration at positions 26 and 27 is preferably

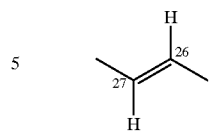

Compounds of the invention of formula IX preferably have the following conformation

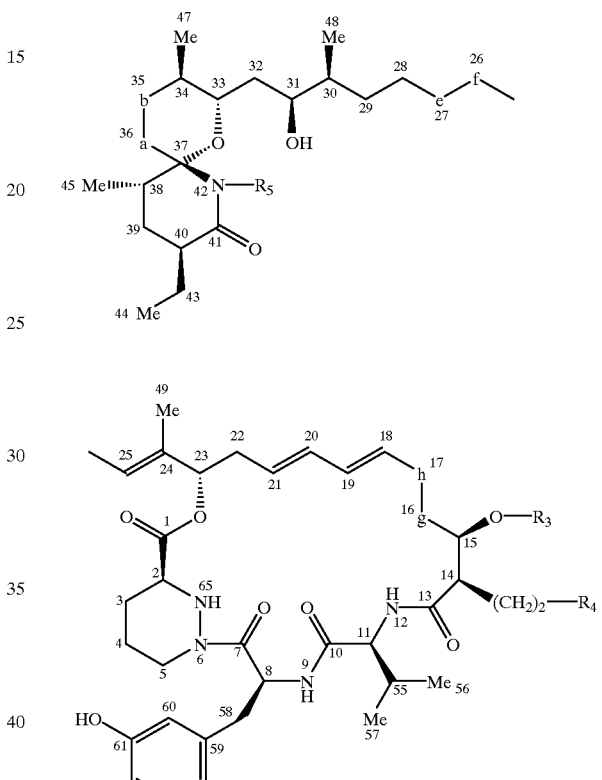

wherein when —a—b— is —(Me)CH—CH(OH)—, it preferably has the configuration:

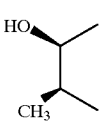

when —e—f— is —CH(OH)—CH(OH)—, it preferably has the (S),(S) configuration or the (R),(R) configuration; when —g—h— is —(Me)CH—CH(OH)—, it preferably has the configuration:

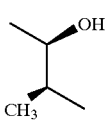

when —g—h— is —(Me)C=CH—, it preferably has the configuration:
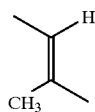
and when $R_3$ and $R_4$ are fused together they are preferably of configuration
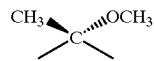
Preferably Sanglifehrins A to C have the following configurations
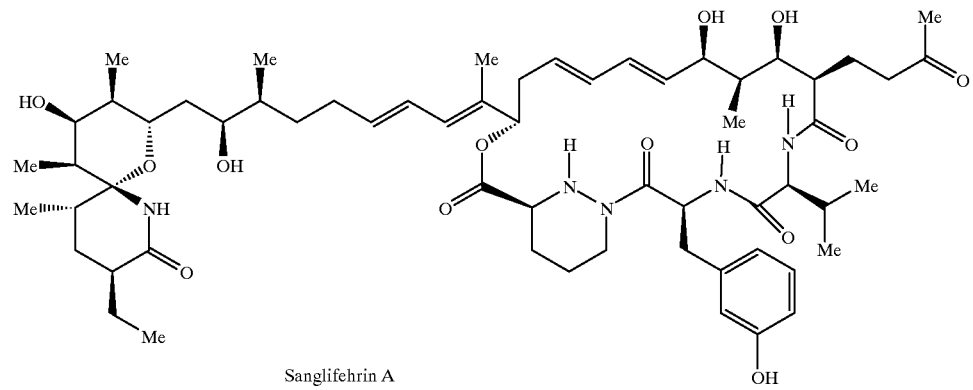
Sanglifehrin A
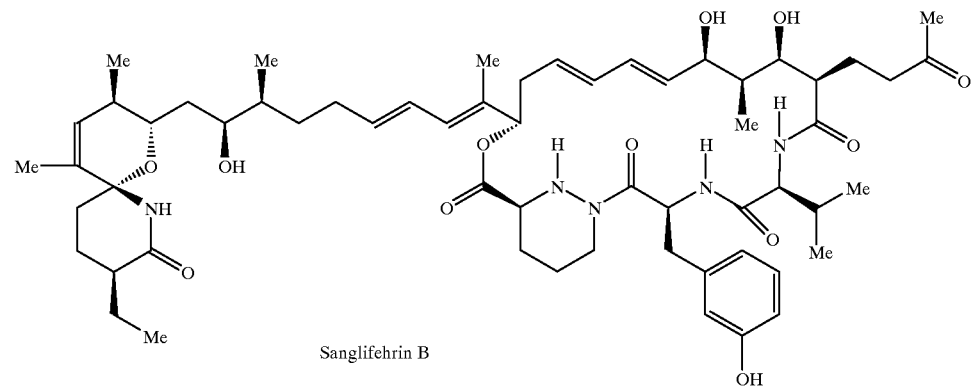
Sanglifehrin B
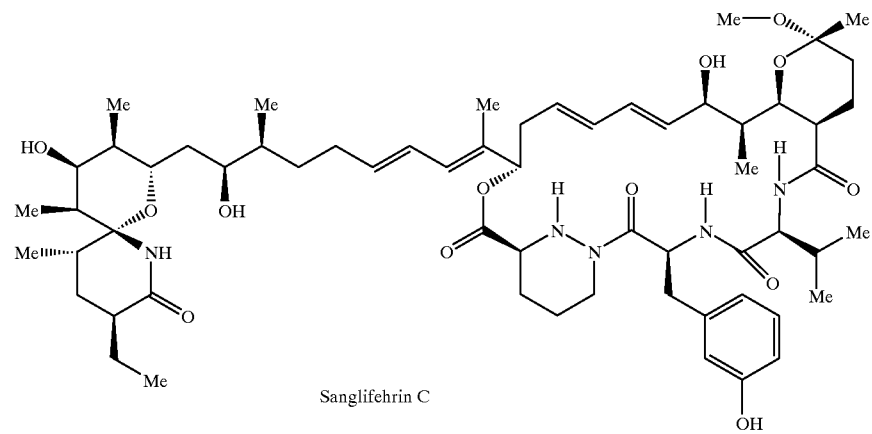
Sanglifehrin C

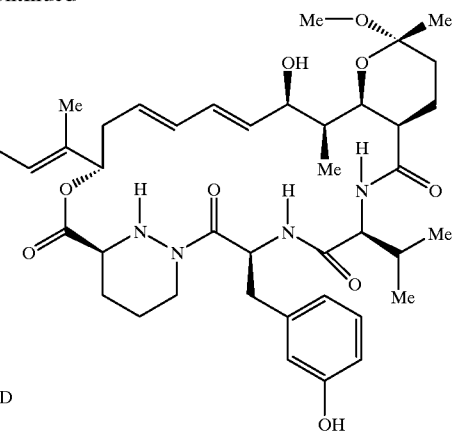

Sanglifehrin D

The compounds of the invention may be in free or protected form, e.g. in protected forms as described in "Protective Groups in Organic Synthesis" by T. W. Greene and P. G. M. Wuts, 2nd Edition, 1991, John Wiley & Sons Inc., New York. In particular OH groups may be in protected form, e.g. in the form of silyl ethers (for instance as described in pages 68–86 of Greene and Wuts ibid.), esters (see e.g. pages 87–103 of Greene and Wuts ibid) and carbonates (see e.g. pages 104–111 of Greene and Wuts ibid). Such protected forms also include internally protected forms; for example, in the case of macrolides of formula IX, wherein —g—h— is —CH(CH$_3$)—CH(OH)—, the protected form wherein the 14 to 17 positions of the macrocyclic ring comprise a residue of formula X:

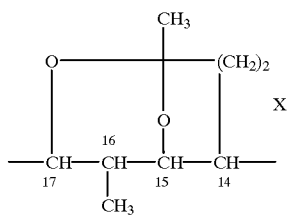

e. g. of configuration

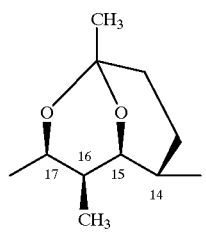

Also for example, 1,3 diols present in Sanglifehrins may be protected as appropriate ring structures, e.g. as described on pages 118–142 of Greene and Wuts ibid.

Compounds of the invention also exist in salt form. Examples of suitable pharmaceutically acceptable salts for use in accordance with the invention include acid and base addition salts as appropriate having, regard to the particular substituents present in the compound, e.g. HCl salt forms.

As previously indicated the macrocyclic ring of the compounds of the invention can be cleaved, in particular at the lactone oxy group, to provide compounds wherein the macrocyclic ring is in ring-open form. Generally cleavage of the lactone oxy group proceeds by hydrolysis (solvolysis), e.g. to provide ring-open macrocycle compounds of formula XI:

$$R_6O—X—Y—Z—A—OH \qquad XI$$

e.g. of formula XII

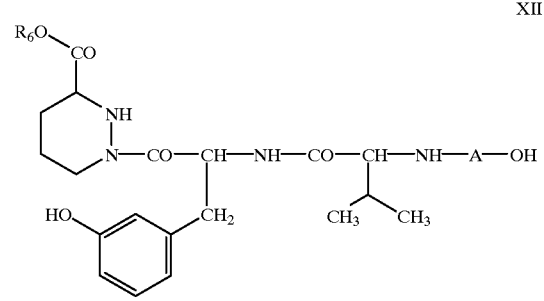

e.g. a compound of formula IX'

IX'

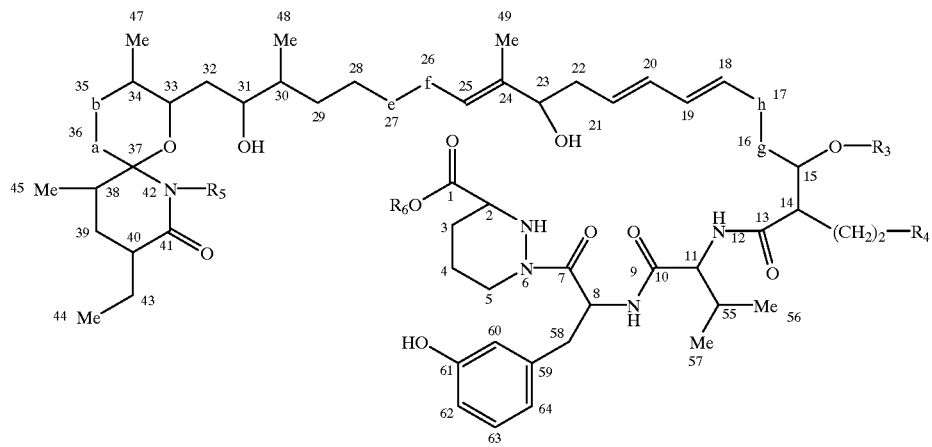

wherein X, Y, Z, A, —a—b—, —e—f—, —g—h—, R$_3$, R$_4$ and R$_5$ are as defined above and R$_6$ is H or C$_{1-4}$ alkyl, e.g. methyl.

Such ring-opened forms provide intermediate means for modification of the basic Sanglifehrin macrocyclic ring system and are also part of the present invention.

Accordingly in a further aspect the present invention provides:

- a macrolide as hereinbefore defined in ring-opened form, said ring-opened macrocycle being in free or protected form, or salt thereof;
- a compound R$_6$O—X—Y—Z—A—OH as defined above, in free or protected form, or salt thereof;
- a compound R$_6$O—X—Y—Z—A'—CH(OH)—L—S, wherein —A'—CH(OH)— is a hydroxy carboxylic acid residue, e.g. a residue of formula II, as defined above, and the other symbols are as defined above, in free or protected form, or a salt thereof;
- a compound of formula XII'

XII'

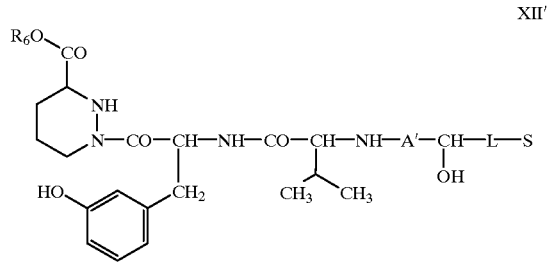

in free or protected form, or salt thereof;

a compound of formula IX'

IX'

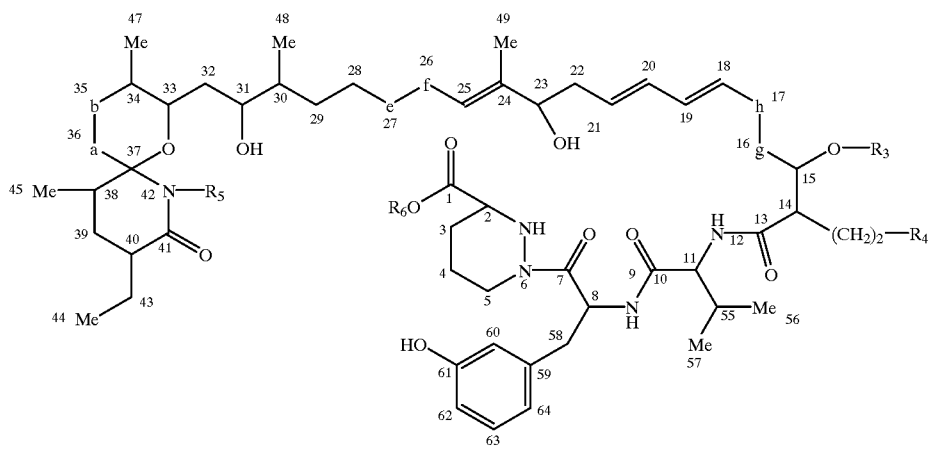

in free or protected form or a salt thereof.

In particular embodiments of this aspect the invention provides a compound of formula IX"

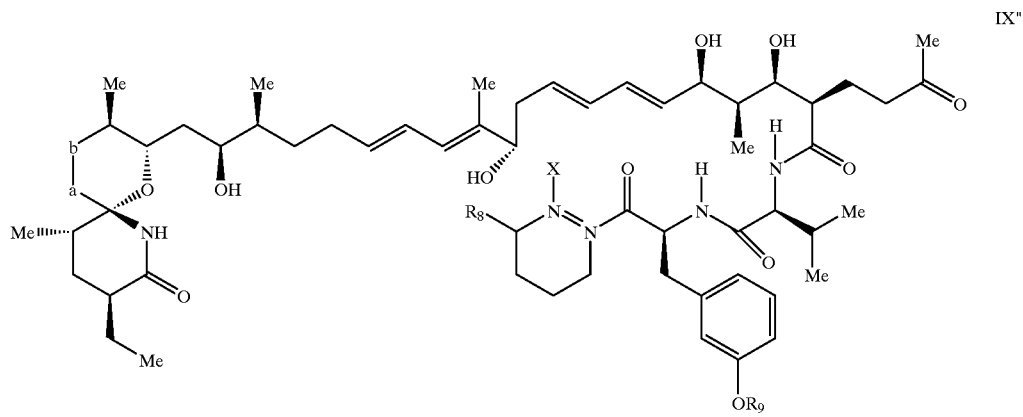

wherein —a—b— is —(Me)C=CH— or —(Me)CH—CH(OH)—;

$R_8$ is H or —C(O)—$OR_{10}$, wherein $R_{10}$ is H or Me;

$R_9$ is H or, when —a—b— is —(Me)CH—CH(OH)— and R is —C(O)—OMe, $R_9$ is Me, and X is H when —N═N— represents a single bond between the two N atoms, or X together with —N═N— represents a double bond between the two N atoms, in free or protected form or a salt thereof.

More particularly the invention provides compounds of formulae W, Y (Seco-sanglifehrin A), S (Seco-sanglifehrin B) and T

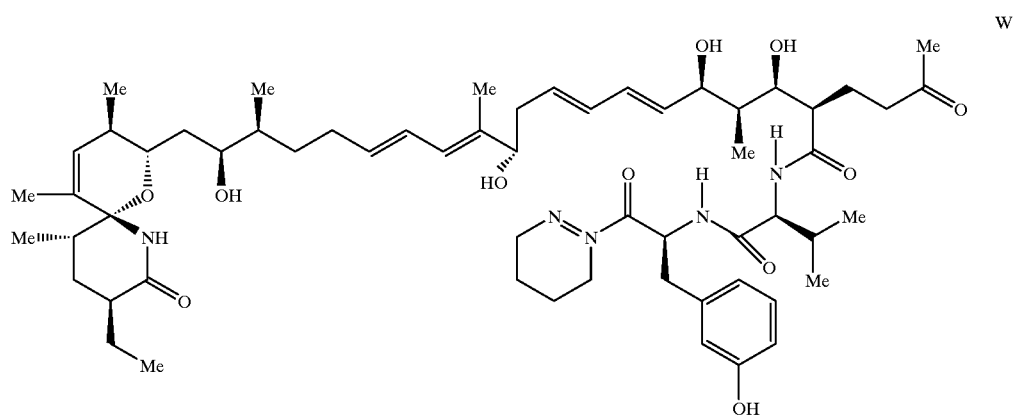

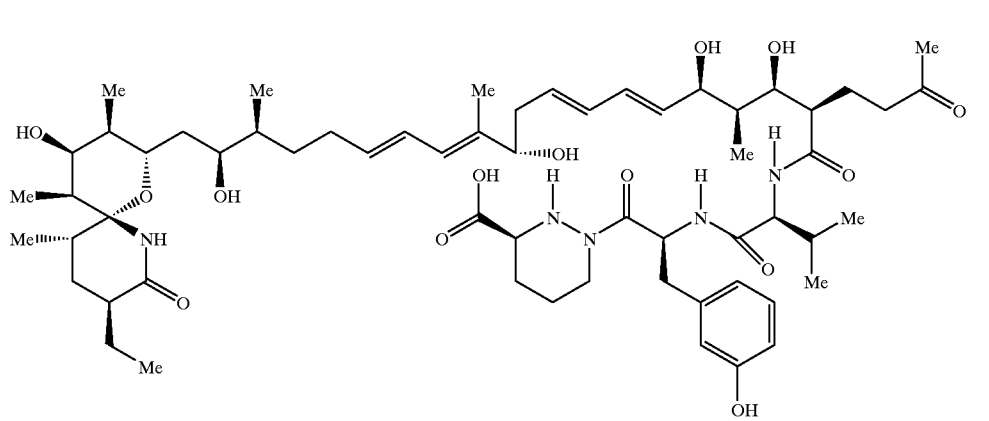

-continued

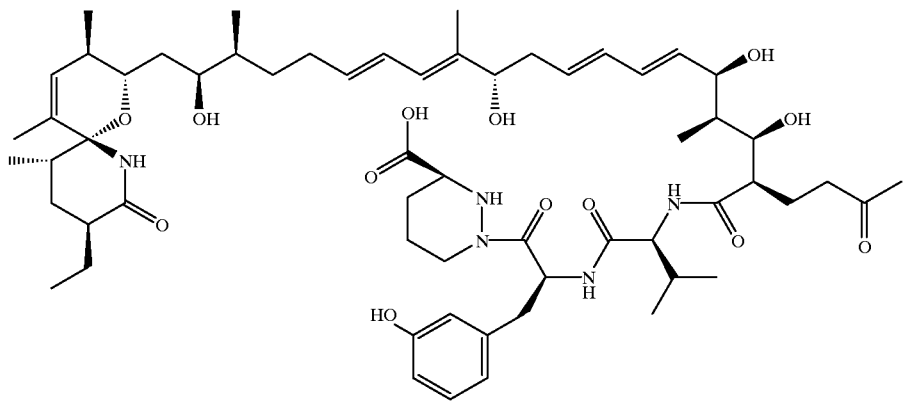

S

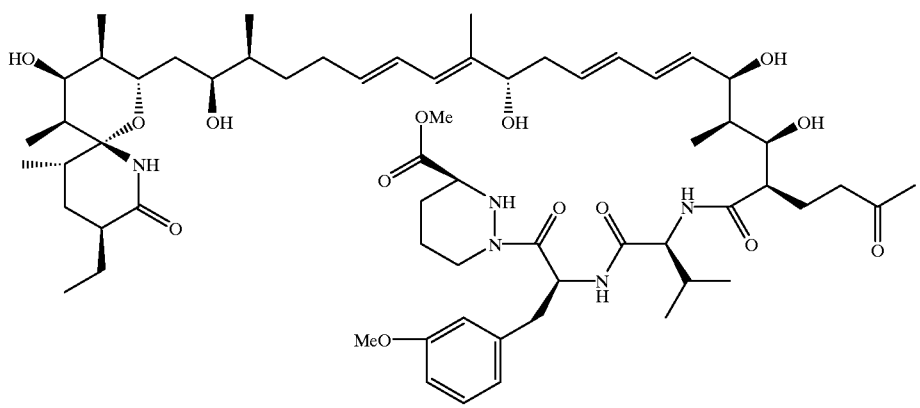

T

The invention also includes compounds in which the 1-oxo-7-aza-spiro-{5,5}-undecan-8-one-2-yl ring system is in ring-opened form, e.g. a compound of formula XIII

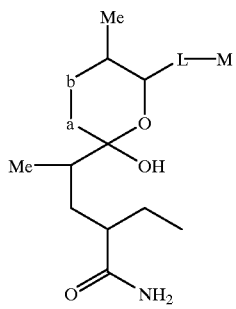

XIII wherein a, b, L and M are as defined above, in free or protected form, or a salt thereof.

The ring-opened compounds of the invention are preferably of conformation as the preferred conformations identified above for ring-closed compounds. The ring-opened spiro bicyclo ring system of compounds of formula XIII is preferably of conformation:

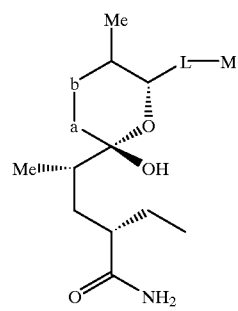

wherein when —a—b— is —(Me)CH—CH(OH)—, it preferably has the configuration:

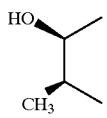

In particular the invention provides a compound of formula Z (Sanglifehrin E)

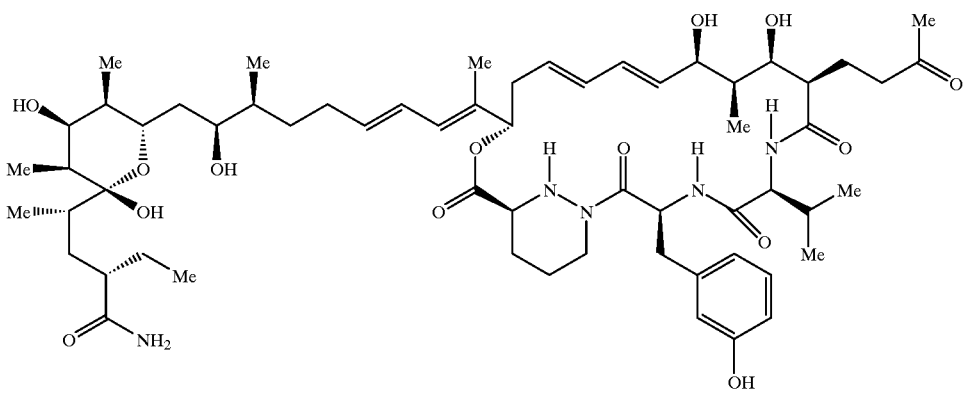

in free or protected form, or a salt thereof.

The compounds of formulae IX", S, T, W, Y, XIII and Z are useful intermediates for the preparation of sanglifehrins in general including ring closed forms and ring expanded ring closed forms.

The compounds of formulae IX" may be prepared by cleavage of the macrolide ring of a ring closed sanglifehrin, e.g. sanglifehrin A or B, at or in the vicinity of the lactone oxy group. Thus, for example, the compounds of formula Y and T are prepared by treatment of sanglifehrin A under basic conditions, e.g. for the compound of formula III in the presence of an alkali metal hydroxide and e.g. for the compound of formula IV in the presence of methanol and an alkali metal carbonate.

Alternatively compounds of formula IX" may be obtained as isolates from cultures of a sanglifehrin producing microorganism. For example, the compounds of formula Y and S may be obtained as isolates from the cultures of Streptomyces sp. A92-308110 as hereinafter described.

The isolation of the compounds of formulae Y and S from cultures of Streptomyces sp. A92-308110 is described in Example 2.

The compound of formula Z may be obtained by cleavage of the spiro bicyclic ring system between the nitrogen atom and the central atom of the spiro system. Alternatively the compound of formula Z may be obtained as an isolate from a culture of a sanglifehrin producing microorganism. For example, the isolation of the compound of formula Z from cultures of Streptomyces sp. A92-308110 is described in Example 2.

Macrolides in accordance with the invention having a spiro bicyclo residue attached to the macrocyclic ring may also be subjected to cleavage of the intervening linker group, e.g. in relation to formula IX, in particular at the linkage between residues 26 and 27 to yield separate novel Spiro bicyclo compounds and further macrolides. As also previously indicated these compounds too are useful as intermediates, the spiro bicyclic moiety of the Sanglifehrins in particular having an integral functional role in the biological activity of the Sanglifehrins as a class.

Accordingly the present invention provides a 1-oxo-7-aza-spiro-{5.5}-undecan-8-one-2-yl, in free or protected form, or a salt thereof, in particular a compound of formula VI'

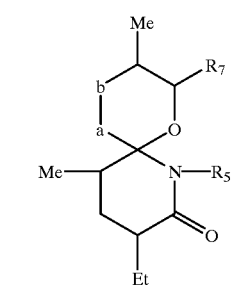

wherein $R_7$. is H, an optionally protected OH group, a reactive functional group, or a —$CH_2$—CH(OH)—CH($CH_3$)—$CH_2$—$CH_2$—CHO group or the delta lactol equivalent thereof, in free or protected form or salt thereof.

Preferably the compound of formula VI' has the following configuration

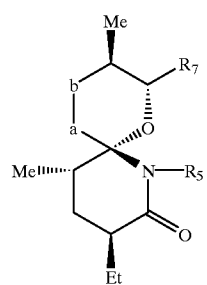

wherein when —a—b— is —(Me)CH—CH(OH)—, it preferably has the configuration:

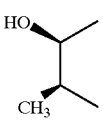

The invention also includes a ring-open 1-oxo-7-aza-spiro-{5.5}-undecan-8-one-2-yl, in free or protected form, or a salt thereof, in particular a compound of formula XIII'

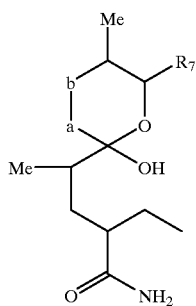

wherein —a—b— and R$_7$ are as previously defined, in free or protected form, or a salt thereof. The ring-opened spiro bicyclo ring system of compounds of formula XIII' is preferably of conformation:

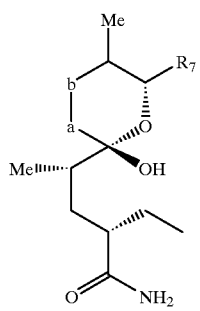

wherein when —a—b— is —(Me)CH—(OH)—, it preferably has the configuration:

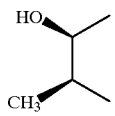

The invention also provides a macrolide of formula XIV

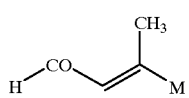

wherein M is a macrolide ring as defined above, in particular a macrolide of formula XV

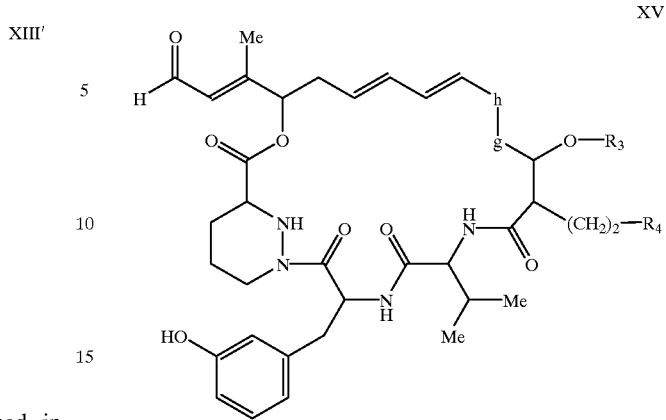

preferably of conformation

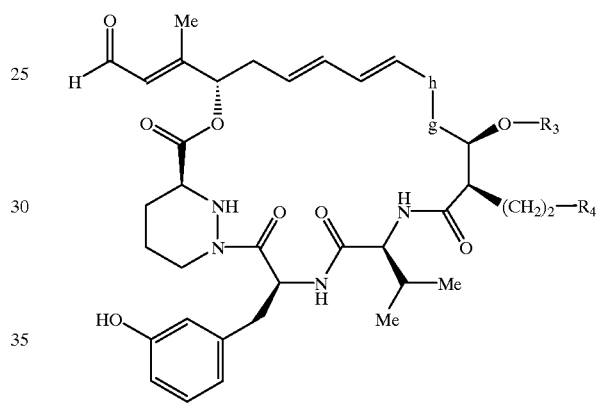

wherein when —g—h— is —(Me)CH—CH(OH)—, it preferably has the configuration:

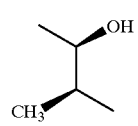

and when —g—h— is —(Me)C=CH—, it preferably has the configuration:

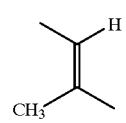

and when R$_3$ and R$_4$ are fused together they are preferably of configuration

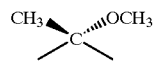

in free or protected or ring-opened form, or a salt thereof.

In a further aspect the invention includes the macrolides and compounds of the invention, in particular those which are natural products in substantially purified form, e.g. at least 90%, preferably at least 95%, especially at least 98% pure form.

In addition to the foregoing the present invention also provides a process for the production of any compound of the invention as hereinbefore defined, which process comprises:

i). for the production of any one of Sanglifehrins A, B, C, D, E, Seco-sanglifehrin A or Seco-sanglifehrin B, cultivating a Sanglifehrin A, B, C, D, E, Seco-sanglifehrin A or Seco-sanglifehrin B producing actinomycete strain in a culture medium and isolating the desired Sanglifehrin A, B, C, D, E, Seco-sanglifehrin A or Seco-sanglifehrin B from the obtained culture broth;

ii). for the production of Sanglifehrins C and D subjecting Sanglifehrins A and B to cyclisation at positions 15 and 16;

iii). for the production of Sanglifehrins A and B subjecting Sanglifehrins C and D to ring opening of the lactol ring at positions 15 and 16;

iv). for the production of a macrolide of formula IXa, IX or IX', wherein —g—h— is —C(CH$_3$)=CH—, dehydrating a compound of formula IXa, IX or IX' wherein —g—h— is —CH(CH$_3$)—CH(OH)— or a protected form thereof;

v). for the production of a macrolide of formula IXa, IX or IX' wherein R$_4$ is —CH(OH)—CH$_3$, hydrogenating a compound of formula IXa, IX or IX' wherein vi)). for the production of a macrolide of formula IXa, IX or IX' wherein R$_4$ is —C(O)—CH$_3$, dehydrogenating a compound of formula IXa, IX or IX' wherein R$_4$ is —CH(OH)—CH$_3$;

vii) for the production of a macrolide of formula IXa, IX or IX' wherein the 14 to 16 positions of the macrolide ring comprise a residue of formula X

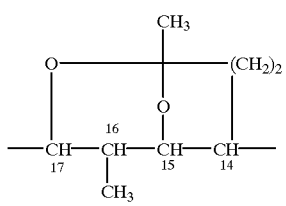

causing a compound of formula IXa, IX or IX' to undergo internal protection at positions 15 and 17;

viii). for the production of a macrolide of formula IXa, IX or IX', causing a compound of formula IXa, IX or IX' wherein the 14 to 16 positions of the macrolide ring comprise a residue of formula X

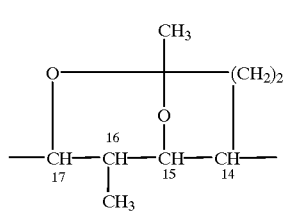

to undergo reversal of internal protection at positions 15 and 17;

ix). for the production of a macrolide of formula IXa, IX or IX', in which R$_5$ is methyl, subjecting a macrolide of formula IXa, IX or IX', in which R$_5$ is H to methylation;

x). for the production of a macrolide of formula IXa, IX or IX', in which R$_4$ is in O-protected form, subjecting a macrolide of formula IXa, IX or IX', in which R$_4$ is in O-unprotected form to O-protection;

xi). for the production of a macrolide of formula IXa, IX or IX', in which R$_4$ is in O-unprotected form, subjecting a macrolide of formula IXa, IX or IX', in which R$_4$ is in O-protected form to O-deprotection;

xii). for the production of a macrolide of formula IXa, IX or IX', which comprises an O-protected hydroxyphenylalanine residue at positions 7 to 10 of the macrocyclic ring, subjecting a macrolide of formula IXa, IX or IX', which comprises an O-unprotected hydroxyphenylalanine residue at positions 7 to 10 of the macrocyclic ring to O-protection;

xiii). for the production of a macrolide of formula IXa, IX or IX', which comprises an O-unprotected hydroxyphenylalanine residue at positions 7 to 10 of the macrocyclic ring, subjecting a macrolide of formula IXa, IX or IX' which comprises an O-protected hydroxyphenylalanine residue at positions 7 to 10 of the macrocyclic ring to O-deprotection;

xiv). for the production of a macrolide of formula IXa, IX or IX', in which —e—f— is —CH(OH)—CH(OH)—, subjecting a macrolide of formula IXa, IX or IX' in which —e—f— is —CH=CH— to oxidative hydrolysis;

xv). for the production of a compound of formula V' or a compound of formula XIII, subjecting a compound of formula IXa, IX or IX' to cleavage of the linker group between the spiro bicyclo group and the macrocyclic ring.

xvi). for the production of a compound of formula R$_6$O—X—Y—Z—A—OH or of formula R$_6$O—X—Y—Z—A'—CH(OH)—L—S, subjecting a macrocycle of formula IV or the macrocyclic ring of a compound of formula VIII to ring-opening at the lactone bridge thereof;

xvii). for the production of a macrolide of formula IX or XII in ring-closed form, subjecting a compound of formula R$_6$O—X—Y—Z—A—OH or of formula R$_6$O—X—Y—Z—A'—CH(OH)—L—S to closure of the macrocyclic ring.

xviii). for the production of a compound of formula XIII or XIII', subjecting a compound of formula IX or VI' to ring-opening within the spiro bicyclic ring system, and xix). for the production of a compound of formula IX or VI', subjecting a compound of formula XIII or XIII' to ring-closure within the spiro bicyclic ring system.

Processes of the invention may be performed, e.g. as described in the examples. As will be appreciated the processes defined above may be applied in any appropriate sequence or combination to obtain other macrolides in free, protected, rig-open and ring-closed form as hereinbefore described.

The macrolides of the invention, e.g. Sanglifehrins A to D, are, or are derived from, natural compounds typically obtained from members of the family Streptomycetaceae.

Microorganisms capable of producing macrolides as hereinbefore defined have not previously been identified.

Accordingly in a yet further aspect the present invention provides:

a macrolide producing actinomycete strain wherein the macrolide is a macrolide in which
i) positions 2 to 6 inclusive of the macrocyclic ring are provided by a piperidazinyl carboxylic acid residue; and/or
ii) positions 7 to 9 inclusive of the macrocyclic ring are provided by an aromatic α-amino acid residue; and/or
iii) positions 10 to 12 inclusive of the macrocyclic ring are provided by an aliphatic α-amino acid residue, in particular any such macrolide as hereinbefore defined, more particularly a Sanglilfehrin A, B, C or D producing actinomycete strain.

Suitably the actinomycete strain is of the family Streptomycetaceae, more suitably of the genus Streptomyces, in particular the strain Streptomyces sp. A92-308110 as hereinafter described, or is derived therefrom, e.g. including mutants, variants, fusants, recombinants or modified forms, including genetically modified and mutagenised forms, thereof.

Suitably the strains of the invention are in the form of biologically pure isolates.

For example Streptomyces sp. A92-308110 may be mutated or modified into different forms by conventional techniques, e.g. by UV radiation or by treatment with a chemical mutagen such as N-methyl-N'-nitro-nitrosoguanidine. Recombinant clones may be obtained by protoplast fusion. All such mutants or recombinants or modified forms, capable of producing sanglifehrins, including mutants and recombinants capable of producing increased yields of, sanglifehrins are included within the scope of the present invention.

In a particular embodiment of the invention Sanglifehrins A, B, C, and D, amongst others, are isolated from the novel Streptomyces sp. A92-308110. Samples of Streptomyces sp. A92-308110 were deposited with the Deutsche Sammlung von Mikroorganismen und Zelikulturen GmbH, Mascheroder Weg 1b, D-38124 Braunschweig, Germany on the May 3, 1995 under the terms of the Budapest Treaty and have been assigned deposition number DSM 9954. Samples of Streptomyces sp. A92-308110 may also be obtained from Sandoz Ltd. CH-4002 Basel, Switzerland.

The isolation of Sanglifehrins A, B, C, and D from cultures of Streptomyces sp. A92-30810 is described in Example 2.

Streptomvces sp. strain A92-308110 belongs to the genus Streptomyces according to the description in Bergey's Manual (Volume 4, 1989, Williams and Wilkins. Baltimore) and The Prokaryotes (1992 Springer Verlag, New York). The cell walls contain LL-diaminopimelic acid. The fatty acids are iso- and anteiso-branched, straight and unsaturated. The sugar spectrum is non distinctive. The vegetative mycelium does not break down into fragments. The aerial mycelium forms long chains of spores.

According to the reference books cited above, the strain designated A92-308110 is a new Streptomyces. A92-308110 grows on various organic and inorganic media and in most cases forms aerial mycelium. The primary substrate mycelium grows as hyphae and is generally beige to greyish-brown. The color of the aerial mycelium belongs to the grey series, number 4, and this mycelium forms long chains of spores which belong to the type spira b.

The ability of Streptomyces sp. A92-308110 to grow on usual biological media, its carbon utilization, and its physiological characteristics are presented in the following tables.

TABLE 1

Growth on various biological media

| Culture medium | Culture charcteristics |
|---|---|
| yeast extract/ malt agar | growth: good substrate mycelium: brownish aerial mycelium: grayish-brown soluble pigment: none |
| oatmeal agar | growth: good substrate mycelium: dark brown aerial mycelium: greyish-brown soluble pigment: brownish |
| glucose-asparagine | growth: moderate substrate mycelium: brownish aerial mycelium: greyish-brown soluble pigment: none |
| Inorganic salts/ starch agar | growth: moderate substrate mycelium: grey aerial mycelium: greyish-brown soluble pigment: none |
| Sucrose/ nitrate agar | growth: very poor substrate mycelium: whitish aerial mycelium: poor, greyish brown soluble pigment: none |
| Glycerol/ asparagine agar | growth: moderate substrate mycelium: brownish aerial mycelium: greish-brown soluble pigment: none |
| Nutrient agar | growth: moderate substrate mycelium: beige aerial mycelium: none soluble pigment: brown |

TABLE 2 carbon utilization

| moderate or good: | glucose, fructose, arabinose, xylose, mannose, |
| poor: | rhamnose, sucrose, raffinose, cellulose, salicin |
| negative: | m-inositol |

TABLE 3 physiological characteristics

| nitrate reduction: | positive |
| starch hydrolysis: | moderate on inorganic salts-starch agar, negative on oatmeal agar. |
| tyrosine degradation: | negative |
| milk peptonisation: | positive |
| melanin formation: | positive |
| growth temperatures: 18–37° C. Very poor growth at 13° C. No growth at 45° C. | |
| pH-range: | rich growth at pH 5 and 7, good growth at pH 9 |
| NaCl resistance: | up to 6%, but reduced growth already at a 2% concentration. |

Macrolides of the invention, including Sanglifehrins A, B, C and D may be produced by cultivating Streptomyces sp.

A92-308110 or a mutant, recombinant or modified form thereof on an appropriate culture medium. Example 1 describes, by way of illustration only of the invention, a procedure for the cultivation of Streptomyces sp. A92-308110.

Thus in further aspects the invention includes:

a) a biologically pure isolate of strain Streptomyces sp. A92-308110 (DSM 9954) or a mutant, recombinant or modified form thereof which is capable of producing a macrolide of the invention, and b) a process for the production of a macrolide of the invention, which comprises cultivating strain Streptomyces sp. A92-308110 (DSM 9954) or a mutant, recombinant or modified form thereof in an appropriate culture medium and optionally recovering the sanglifehrin.

Macrolides in accordance with the invention, e.g. compounds of formula IX; for example, Sanglifehrins A, B, C and D, and their pharmaceutically acceptable salts, hereinafter generically "agents of the invention", exhibit sanglifehrin characteristic activities, i.e. the following combination of activities:

have cyclophilin binding activity;

have immunosuppressive activity;

inhibit proliferation of both B-cells and T-cells;

but do not have FK binding protein binding activity, and do not inhibit calcineurin activity.

These activities and assays to determine these activities are described hereinafter in greater detail. Biological activity of macrolides of the invention, e.g. of formula IX, e.g of Sanglifehrins A to D, may be demonstrated in standard in vitro and in vivo test methods, e.g. as follows.

1. Proliferative Response Of Lymphocvtes to Allogenic Stimulation

Two-way MLR (Murine Mixed Lymphocyte Reaction)

Spleen cells ($2 \times 10^5$) from Balb/c mice (female, 8–10 weeks) are co-incubated for 4 days with $2 \times 10^5$ spleen cells from CBA mice (female, 8–10 weeks). The allogenic cells induce a proliferative response in the responder spleen cell population which is measured by labelled precursor incorporation into the DNA. Macrolides invention, e.g. compounds of formula IX and their pharmaceutically acceptable salts, e.g. Sanglifehrins A, B, C and D, have $IC_{50}$s in the range from about 30 up to about 200 nM as compared with an $IC_{50}$ of about 20 nM for cyclosporin A when tested in this assay.

Reference

T. Meo (1979) The MLR in the mouse. In: "Immunological Methods", L. Lefkovits and B. Pernis, Eds. Academic Press, N.Y. pp. 227–239

LPS-stimulated Murine B-cells

Spleen cells ($2 \times 10^5$) from CBA mice are incubated for 48 hours with 50 μg/ml LPS plus test compound. Proliferation is measured by labelled precursor incorporation into DNA. Macrolides of the invention, e.g. compounds of formula IX and their pharmaceutically acceptable salts, e.g. Sanglifehrins A, B, C and D, inhibit B-cell proliferation and have $IC_{50}$s in the range from about40 up to about 100 μM.

References

Greaves, M. and J. Janossy, 1972, Elicitation of selective T and B lymphocyte response by cell surface binding ligands, Transplant Rev., 11:87

Janossy, G. and M. F. Greaves, 1971, Lymphocyte activation, I, Response of T and B lymphocytes to phytomitogens, Clin. Exp. Immunol. 9:483–498

3. Cytotoxic and Cytostatic Activity in Vitro Using the THP1 Cell Line

Cytotoxicity is determined using the human monocytic cell line THP1 ($5 \times 10^4$ cells/well) which are incubated in the presence of IFNγ (100 U/ml)and LPS (5 μg/ml) plus test compound (up to 10 μM) for 24 to 72 h at 37° C. Living cells are quantified using the colourimetric read-out MTT which measures mitochondrial dehydrogenase enzymatic activity in living cells (Mossman 1983). Macrolides of the invention, e.g. compounds of formula IX and their pharmaceutically acceptable salts, e.g. Sanglifehrins A, B, C and D, have $IC_{50}$s of about 1000–5000 nM after 24 h incubation in this assay.

Reference

Mossman T. J. (1983), Rapid calorimetric assay for cellular growth and survival: application to proliferation and cytotoxic assays, J. Imm. Methods, 65, 55–63.

4. TNF Release by Human Peripheral Blood Mononuclear Cells

Mononuclear cells are prepared from the peripheral blood of healthy volunteers using Ficoll-Hypaque density separation according to the method of Hansell et al. (1991). Cells ($10^5$ cells/well in 200 μl RPMI 10% FCS by volume) are incubated with serial dilutions of the test compounds for 30 min at 37° C. prior to the addition of stimulus. Interferon γ (100 U/ml) and LPS (5 μg/ml) are used as stimuli to induce Tumour Necrosis Factor (TNF) α release by peripheral blood mononuclear cells. After 3 h incubation, the cells are centrifuged (1200 rpm for 10 min) and the supernatants are collected. The amount of TNF present in the cell supernatants is determined using a commercially available enzyme-linked immunosorbent assay kit. Macrolides of the invention, e.g. compounds of formula IX and their pharmaceutically acceptable salts, e.g. Sanglifehrins A, B, C and D, have $IC_{50}$s in the range from about 200 nm to about 1000 nm when tested in this assay.

5. Cyclophilin Binding Assay

A suitable cyclophilin binding assay is the competitive ELISA test described by Quesniaux in *Eur. J. Immunol.* 1987 17 1359–1365. In this test, the compound to be tested is added during the incubation of cyclophilin (human recombinant cyclophilin A) with coated BSA-cyclosporin A and the concentration required to give a 50% inhibition of the control reaction without competitor is then calculated ($IC_{50}$). An alternative assay is the competitive binding test described by Schneider et al. in Biochemistry (1994), 33, 8218–8224, which involves addition of test compound during the incubation of biotinylated cyclophilin (human recombinant cyclophilin A) with coated BSA-cyclosporin A. The amount of biotinylated cyclophilin bound in the presence and absence of a test compound is determined by incubation with streptavidin-coupled alkaline phosphatase. Macrolides of the invention, e.g. compounds of formula IX, e.g. Sanglifehrin A. B, C and B, have $IC_{50}$s in the range from about 10 to about 100 nM, compared with an $IC_{50}$ of about 80 nM for cyclosporin A when tested in these assays.

Further in vitro assays which may be used to demonstrate the biological activity of Sanglifehrns are IL-2 reporter gene assays and ConA-stimulated spleen cell assays (indicative of effect on T-cell activation).

Macrolides of the invention, e.g. compounds of formula IX, e.g. Sanglifehrin A, B, C and B, do not have FK binding protein binding activity and do not inhibit calcineurin activity when tested in standard tests for these activities.

6. Localised Graft-versus-Host (GvH) Reaction in the Rat [Ford et al., TRANSPL. PROC. 10 (1979) 258]

Spleen cells ($1 \times 10^7$) from 6 week old female Wistar/Furth (WF) rats are injected subcutaneously on day 0 into the left hind-paw of female (F344×WF)$F_1$ rats weighing about 100 g. Animals are treated for 4 consecutive days and the popliteal lymph nodes are removed and weighed on day 7. The difference in weight between the two lymph nodes is taken as the parameter for evaluating the reaction.

Inhibition of GvH reaction in the above test is indicative of pharmaceutical utility. Macrolides of the invention, e.g. compounds of formula IX and their pharmaceutically acceptable salts, e.g. Sanglifehrins A, B, C and D, are able to inhibit the GvH reaction by up to about 30% when administered at a dose of about 1 mg/kg s.c.

7. DTH Induced by SRBC-$T_H$ Cells

Fifty microliters of a 1:1 (v/v) mixture of a $T_H$ (sheep red blood cell primed) cell clone ($2\times10^6$) and a 10% sheep red blood cell (SRBC) suspension are injected s.c. into the right hind footpad of female C57 BL/6 mice (6–12 weeks old). 50 $\mu$l of the SRBC cell suspension (diluted 1:1 v/v with PBS) is injected s.c. into the left hind footpad (to measure non specific increase in footpad swelling due to the injection procedure). Right and left hind footpad thickness is measured 24 hours later.

The percent increase in thickness of the right footpad over the left footpad (z) is calculated. Thickness of right footpad=x. thickness of left footpad=y; % specific increase=z $$z=((x-y)/y)\cdot 100$$

Macrolides of the invention, e.g. compounds of formula IX and their pharmaceutically acceptable salts, e.g. Sanglifehrins A, B, C and D, reduce swelling of the DTH mouse by up to about 50% at doses of the order of 5 mg/kg s.c.

References

A. T. J. Bianchi, H. Hooijkaas, R. Brenner, R. Tees, A A. Nordin & M. H. Schreier (1981) Clones of helper T-cells mediate antigen specific, H-2 restricted DTH. *Nature* 290:62–63

P. Herrmann, M. H. Schreier, J. -F. Borel & C. Feurer (1988) Mast cell degranulation as a major event in the effector phase of delayed-type hypersensitivity induced by cloned helper T cells. *Int. Archs Allergy appl. Immun.* 86: 102–105

8. Rat/Mouse Heart Allotransplantation

The in vivo efficacy of macrolides of the invention is assessed in rat and mouse heart allotransplantation using Alzet osmotic minipumps for s.c. administration. In mouse heart allotransplantation (BALB/c to C3H), macrolides of the invention, e.g. compounds of formula IX and their pharmaceutically acceptable salts, e.g. Sanglifehrins A, B, C and D, prolong graft survival at doses of the order of 30 mg/kg/day. In rat heart allotransplantation (DA to Lewis) treatment with suboptimal doses of cyclosporin A in combination with Macrolides of the invention, e.g. compounds of formula IX and their pharmaceutically acceptable salts, e.g. Sanglifehrins A, B, C and D, prolonged graft survival as exemplified in the table below.

| Cyclosporin A (mg/kg) | Sanglifehrin A (mg/kg) | Graft survival (days) |
|---|---|---|
| 1 | — | 12, 12, 12, 13, 13, 14 |
| 1 | 10 | 29, 30, 45, 48, >51, >46 |
| Control (Placebo) | Control (Placebo) | 6, 6, 6, 6, 6, 6 |

Agents of the invention are useful as pharmaceuticals, e.g. as immunosuppressive as well as an anti-inflammatory agents.

They are, in particular, useful for the prevention of acute and/or chronic organ or tissue allo- and xenotransplant rejection, e.g. for the treatment of recipients of heart, lung, combined heart-lung, liver, kidney, pancreatic, skin or corneal transplants. They are also indicated for the prevention of graft-versus-host disease, such as following bone marrow transplants.

Agents of the invention are also useful for the treatment of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific autoimmune diseases for which the agents of the invention may be employed include autoimmune haematological disorders (including e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal and/or allergic keratoconjunctivitis, interstitial lung fibrosis, psoriatic arthritis, glomerulonephritis (with and without nephrotic syndrome, e.g. including idiopathic nephrotic syndrome or minimal change nephropathy) and asthma.

For these and other uses agents of the invention may be administered on their own or together with other immunosuppressant or antiinflammatory agents, including cyclosporins, rapamycins, FK 506, and steroids.

For the above indications the appropriate dosage will, of course, vary depending, and the agent of the invention chosen, for example, on the subject to be treated, the mode of administration and the nature and severity of the condition being treated. However, in general, satisfactory results in animals are obtained at daily dosages of from about 0.01 to 10 mg/kg/day p.o. In larger mammals, for example humans, an indicated daily dosage is in the range of from about 0.5 to about 500 mg of sanglifehrin administered orally once or, more suitably, in divided dosages two to four times/day.

In organ transplantation in humans, oral doses of 0. 1 to 100, preferably 0.3 to 30, more preferably 0.5 to 10, mg/kg of a compound of agent of the invention. When an agent of the invention is given along with other immunosuppressants (e.g. with corticosteroids or with compounds of the cyclosporin or rapamycin class as part of a double, triple or quadruple drug therapy) lower doses (e.g. 0.1 mg/kg/day i.v.; 3 mg/kg/day oral initially) may be used. In particular agents of the invention may be given with other nonsteroidal immunosuppressants, e.g. with cyclosporin A, rapamycin or FK 506, with a view to the partial or complete replacement of steroids.

Agents of the invention may be administered by any conventional route, in particular enterally, e.g. orally, for example in the form of solutions for drinking, tablets or capsules or parenterally, for example in the form of injectable solutions or suspensions. Normally for systemic administration oral dosage forms are preferred, although for some conditions, for example for prevention of rejection of liver transplants, an intravenously injectable form is desirable. Compounds may also be administered topically or dermally, e.g. in the form of a dermal cream or gel or like preparation or, for the purposes of application to the eye, in the form of an occular cream, gel or eye-drop preparation. Suitable unit dosage forms for oral administration comprise e.g. from 0.5 to 100 mg of the compound per dosage.

In accordance with the foregoing the present invention also provides in a further series of embodiments:

A. A method of effecting immunosuppression in a subject in need of such treatment which method comprises administering to said subject an effective amount of an agent of the invention.

B. A method:
1) for the prevention of acute and/or chronic organ allo- or xenotransplant rejection, for example for the treatment of recipients of organ transplants of any of the particular types listed above; or
2) for the prevention of graft-versus-host disease, for example in recipients of bone marrow transplants; or
3) for the treatment of autoimmune disease or for the treatment of any such disease or condition listed above; or
4) for the treatment of asthma in a subject in need of such treatment, which method comprises administering to said subject an effective amount of an agent of the invention.

C. An agent of the invention for use as a pharmaceutical, e.g. for use as an immunosuppressant or for use in the treatment of any disease or condition as set forth under B above.

D. A pharmaceutical composition comprising an agent of the invention in association with a pharmaceutically acceptable diluent or carrier.

In addition macrolides of the invention which possess cyclophilin binding activity, may be useful as reagents in displacement immunoassays for cyclosporins and other cyclophilin binding compounds, for example in the assay procedure described in our copending patent application WO 95/07468. This patent application relates to an assay procedure for determining the concentration of an immunophilin-binding pharmaceutical, e.g. Ciclosporin, in blood; the procedure comprising adding a binding competitor that displaces the pharmaceutical from immunosuppressant-immunophilin complexes in the blood; adding a receptor that binds to the pharmaceutical but not significantly to the binding competitor; separating the receptor-pharmaceutical complex from the sample; and determining the amount of the pharmaceutical. Sanglifehrins may be used as the binding competitor in such assays; for instance, to displace cyclosporins from cyclophilins, thereby releasing the cyclosporin for quantitation, e.g. by a monoclonal antibody which is specific for the cyclosporin.

The invention is further described by way of illustration only in the following Examples which refers to the accompanying Figures:

in which

Figure 2:
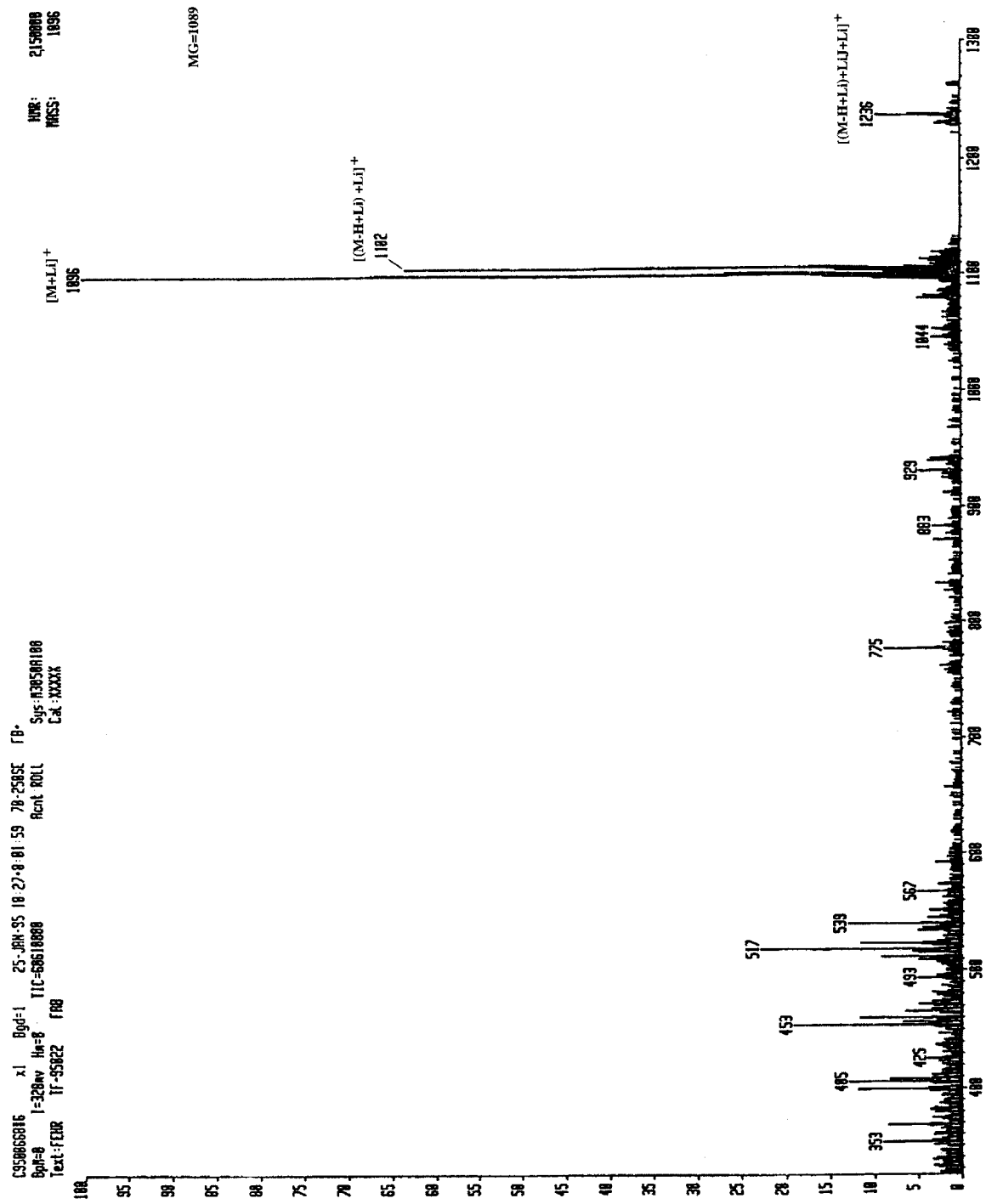
Figure 3:
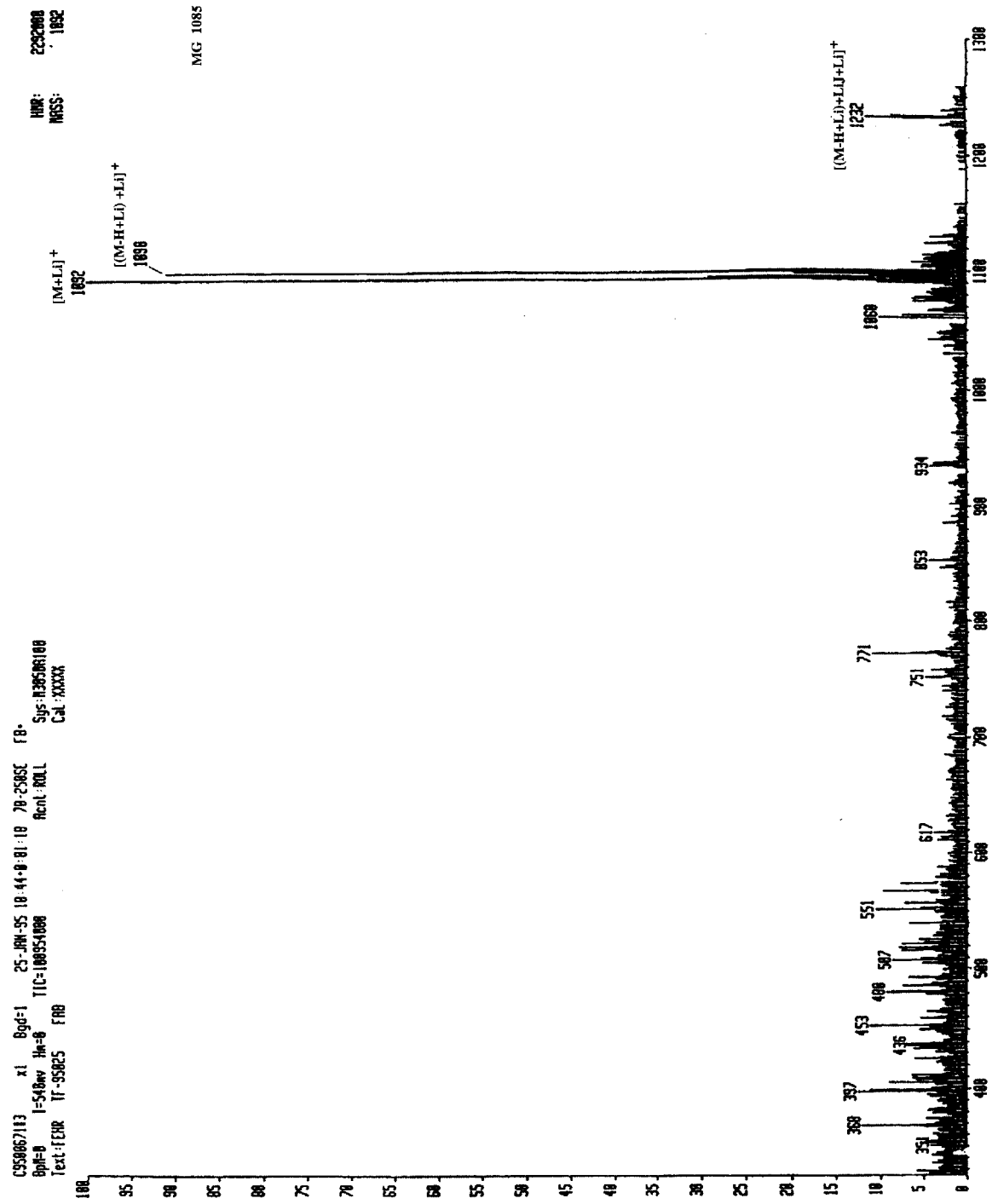
Figure 4:
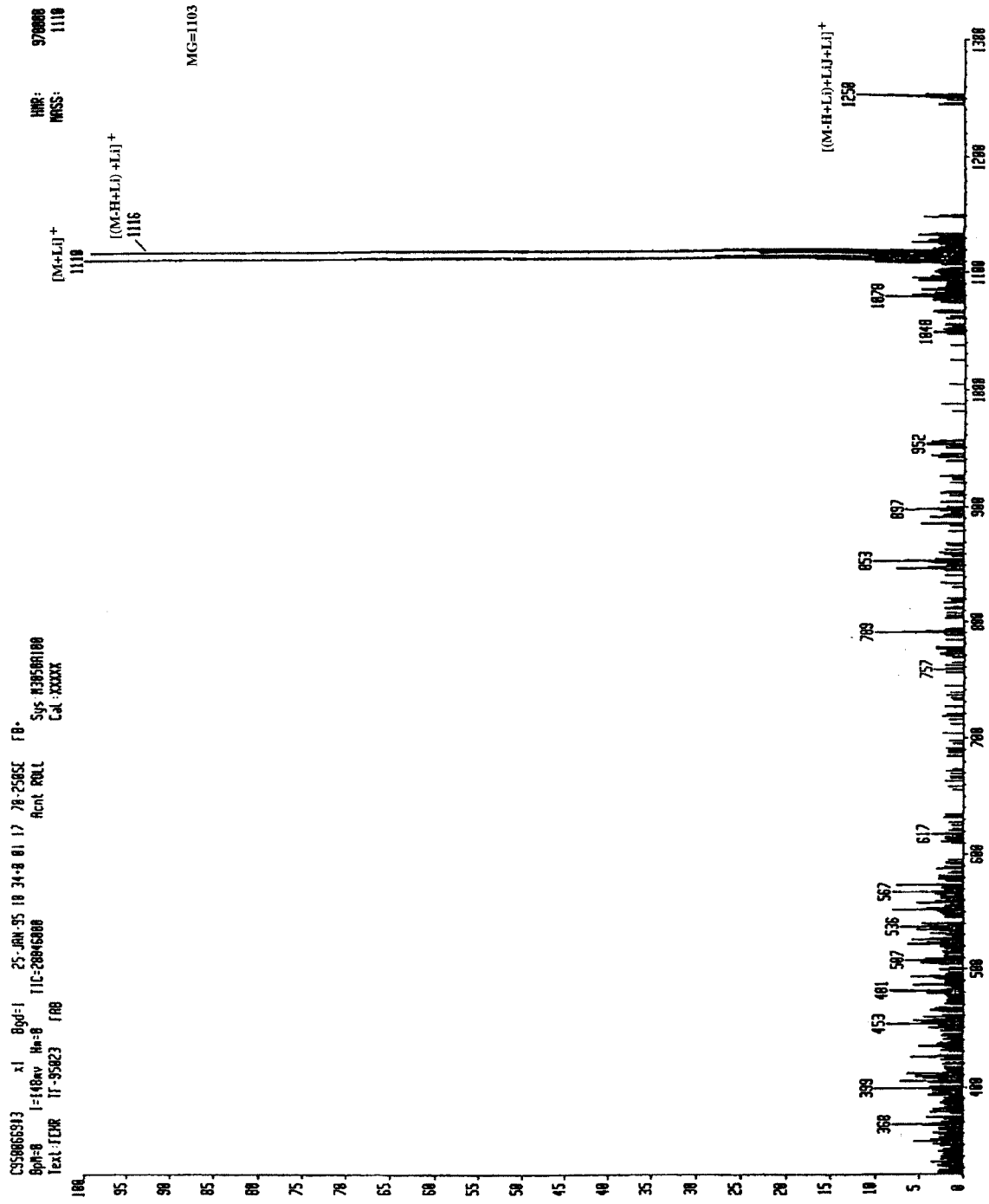
Figure 5:
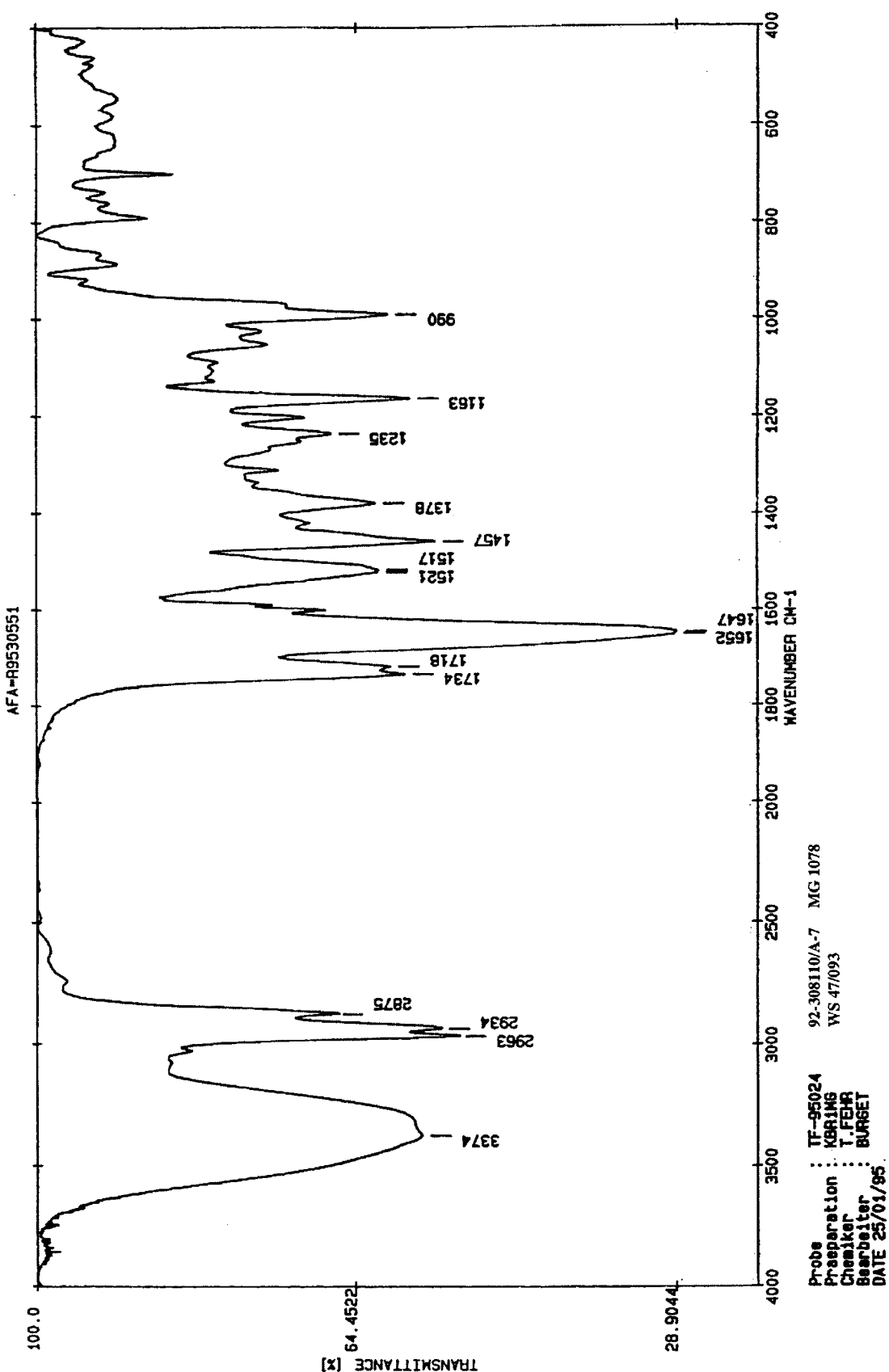
Figure 6:
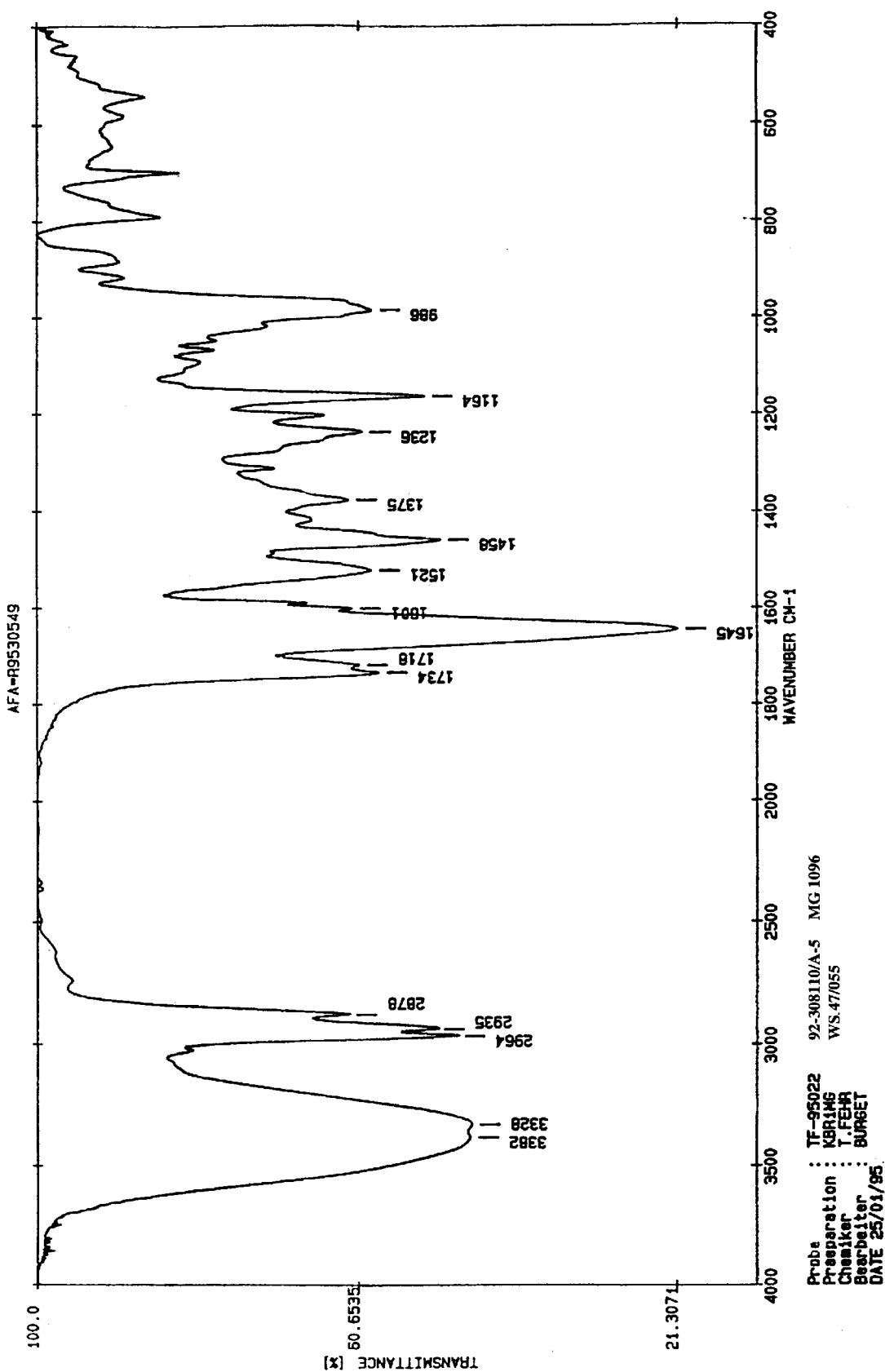
Figure 7:
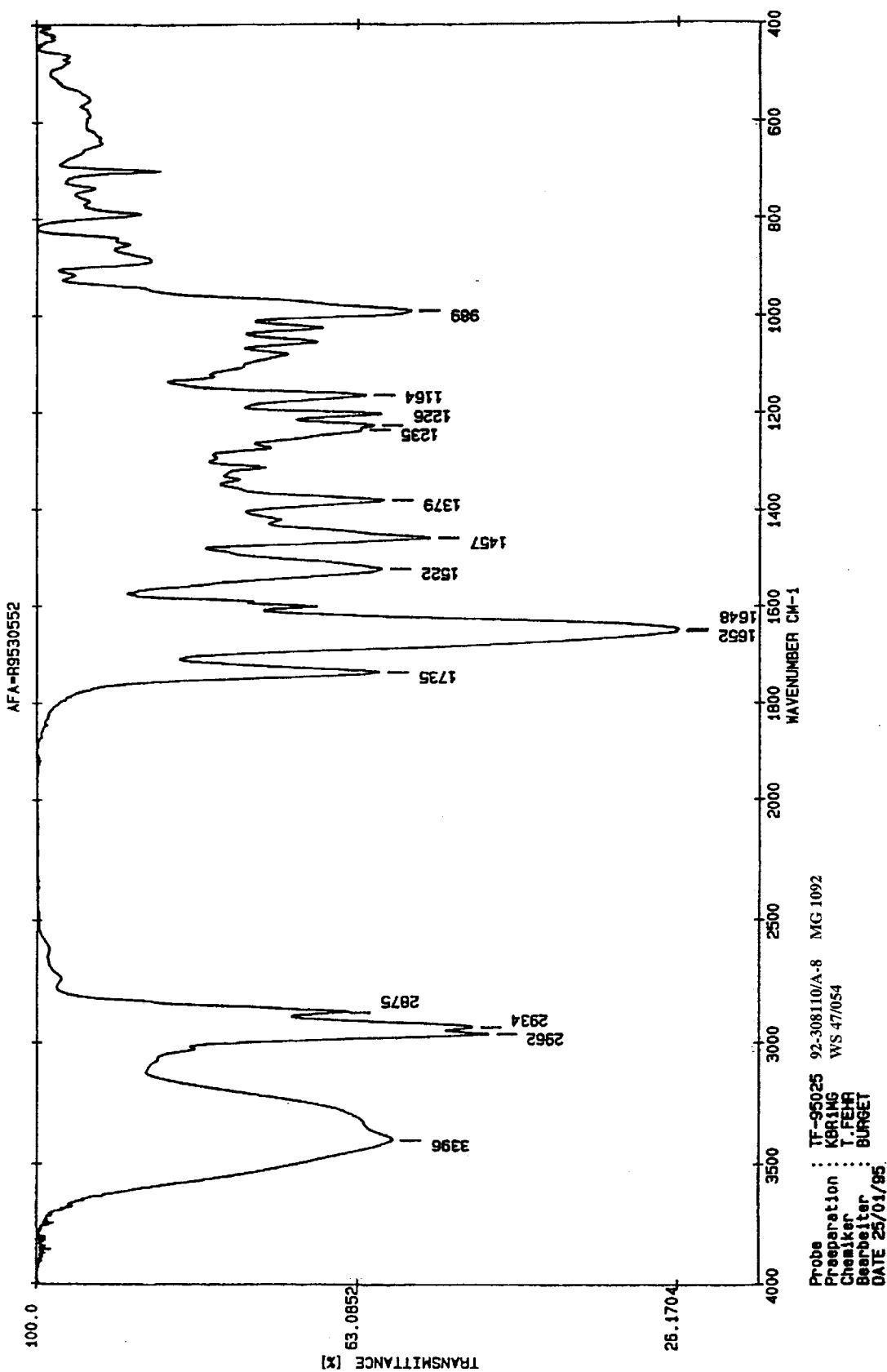
Figure 8:
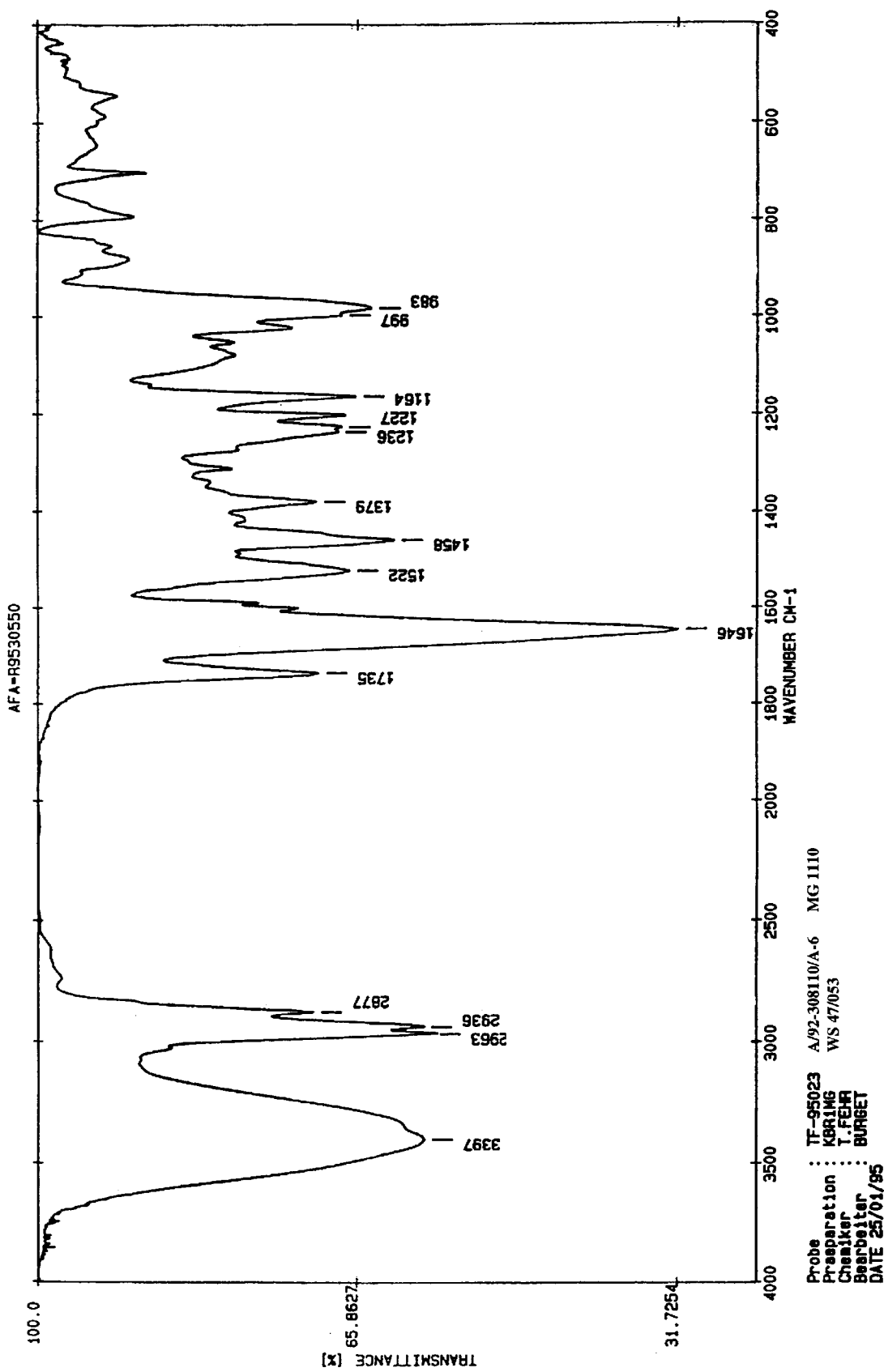
Figure 9:
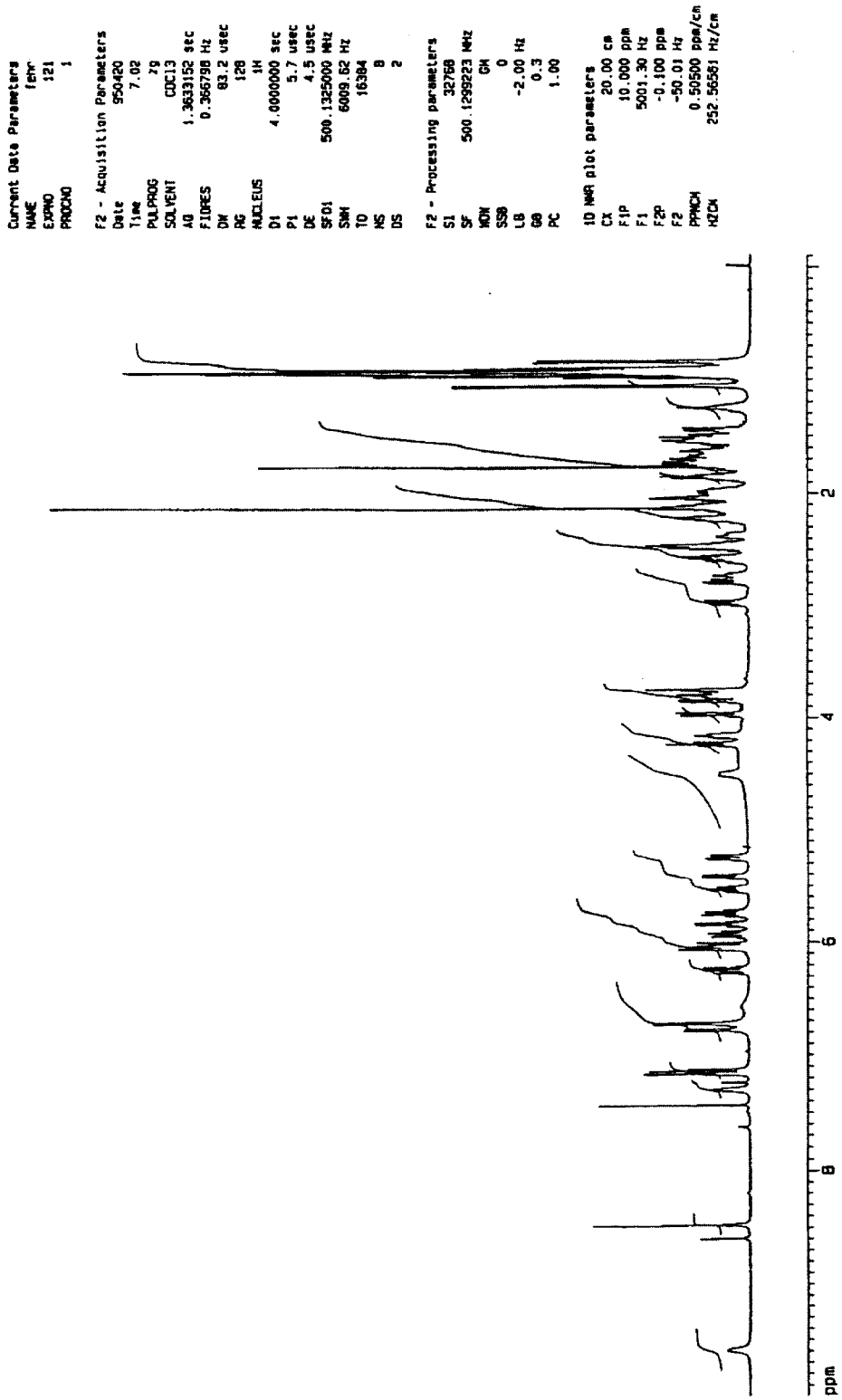
Figure 10:
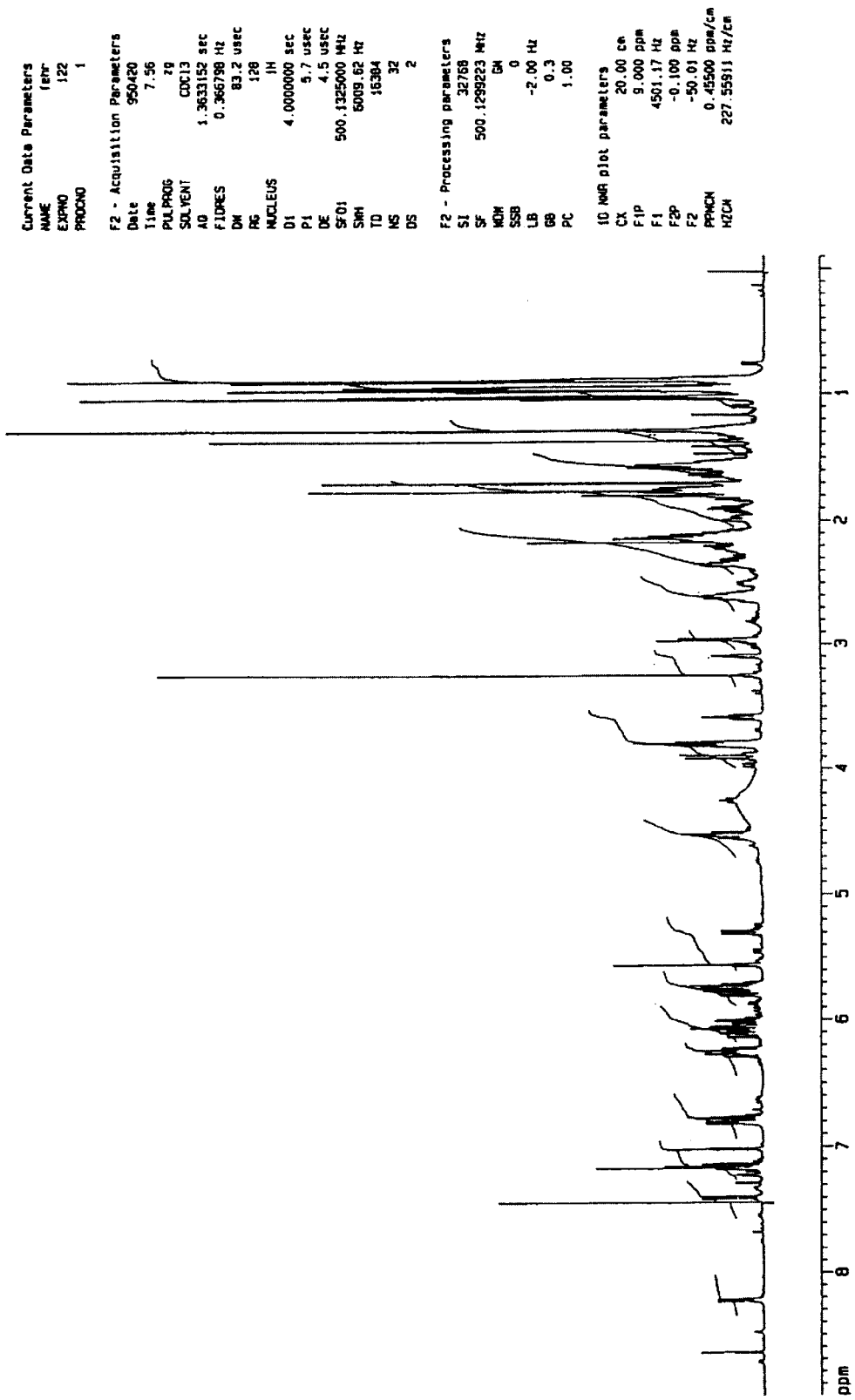
Figure 11:
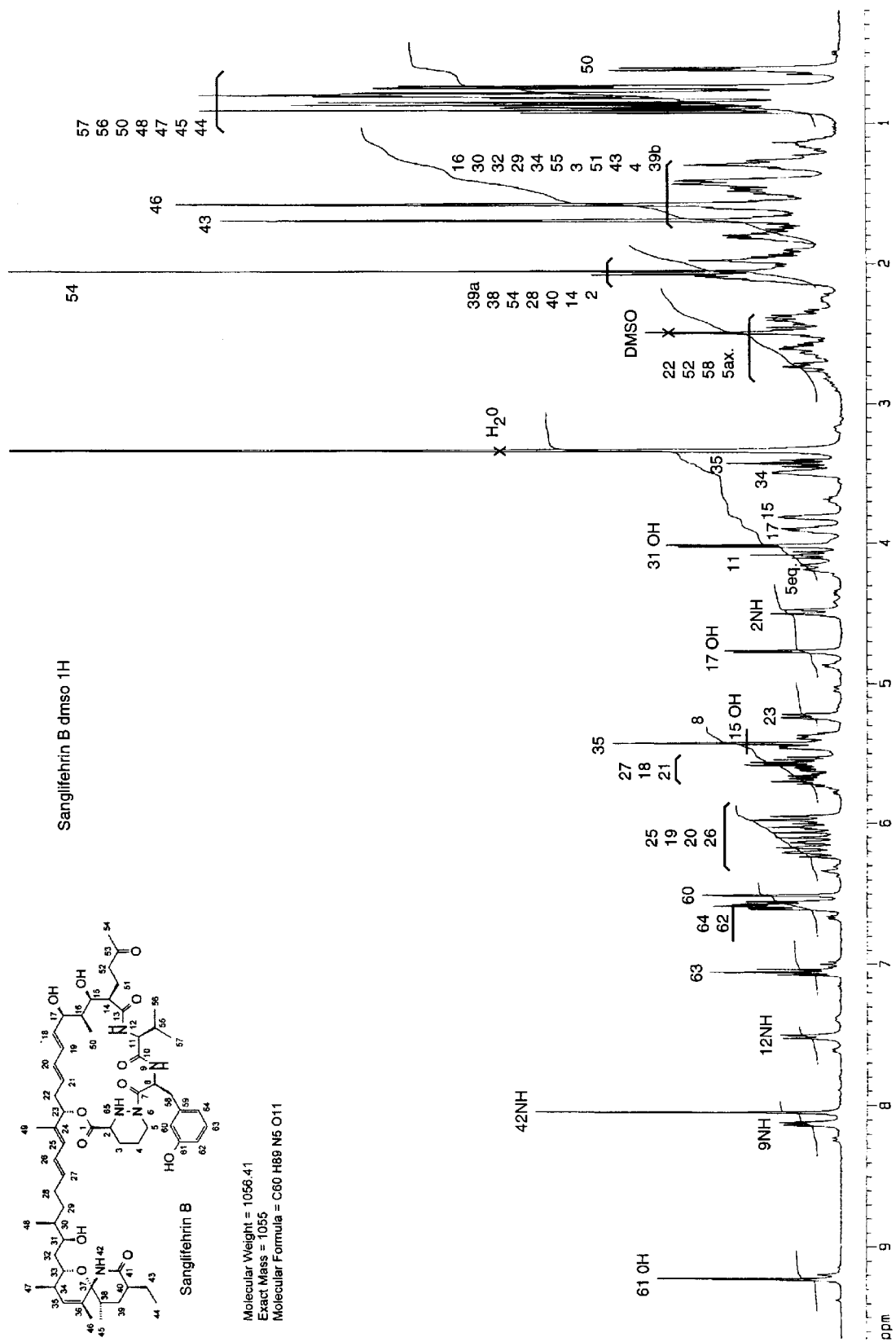
Figure 12:
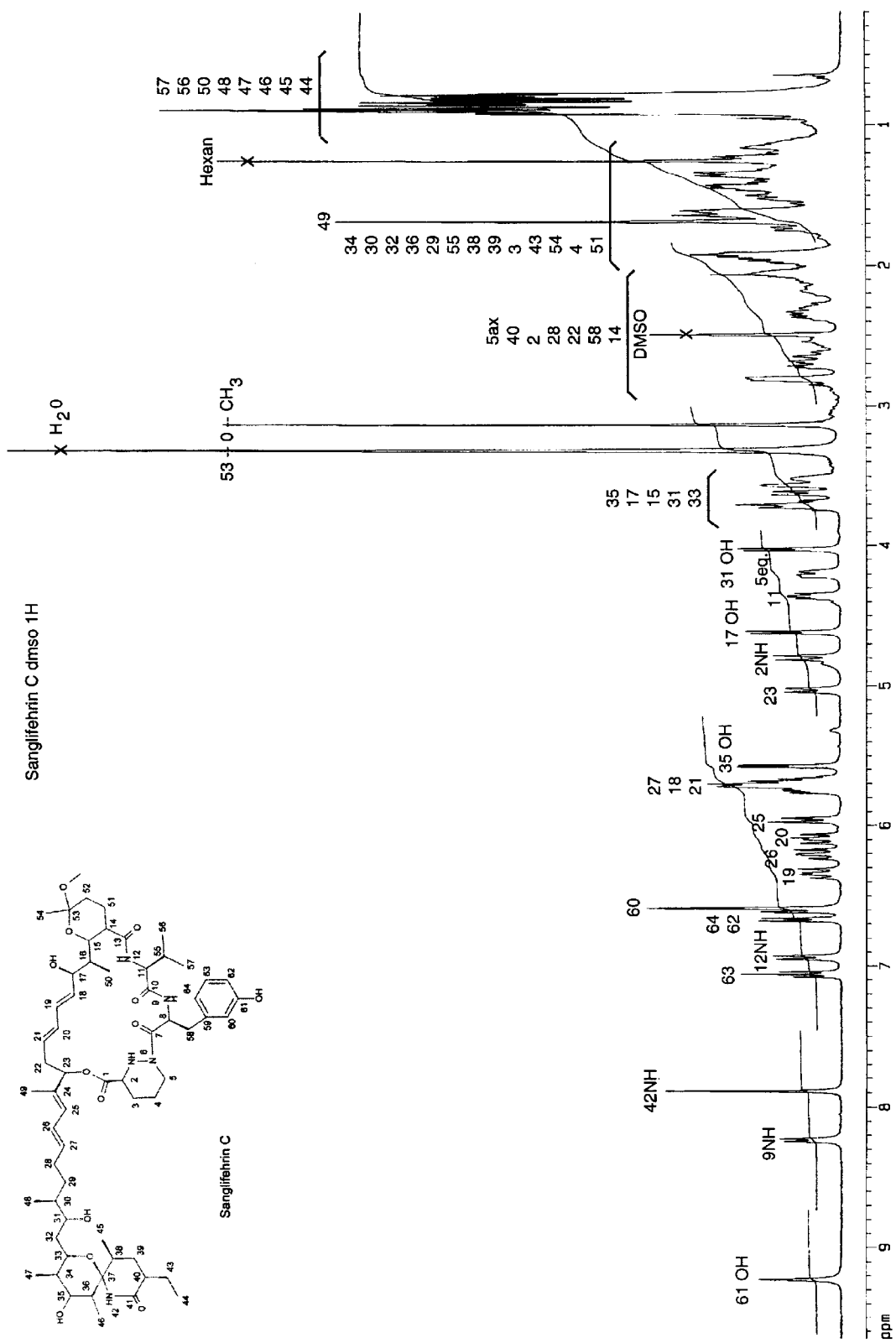
Figure 13:
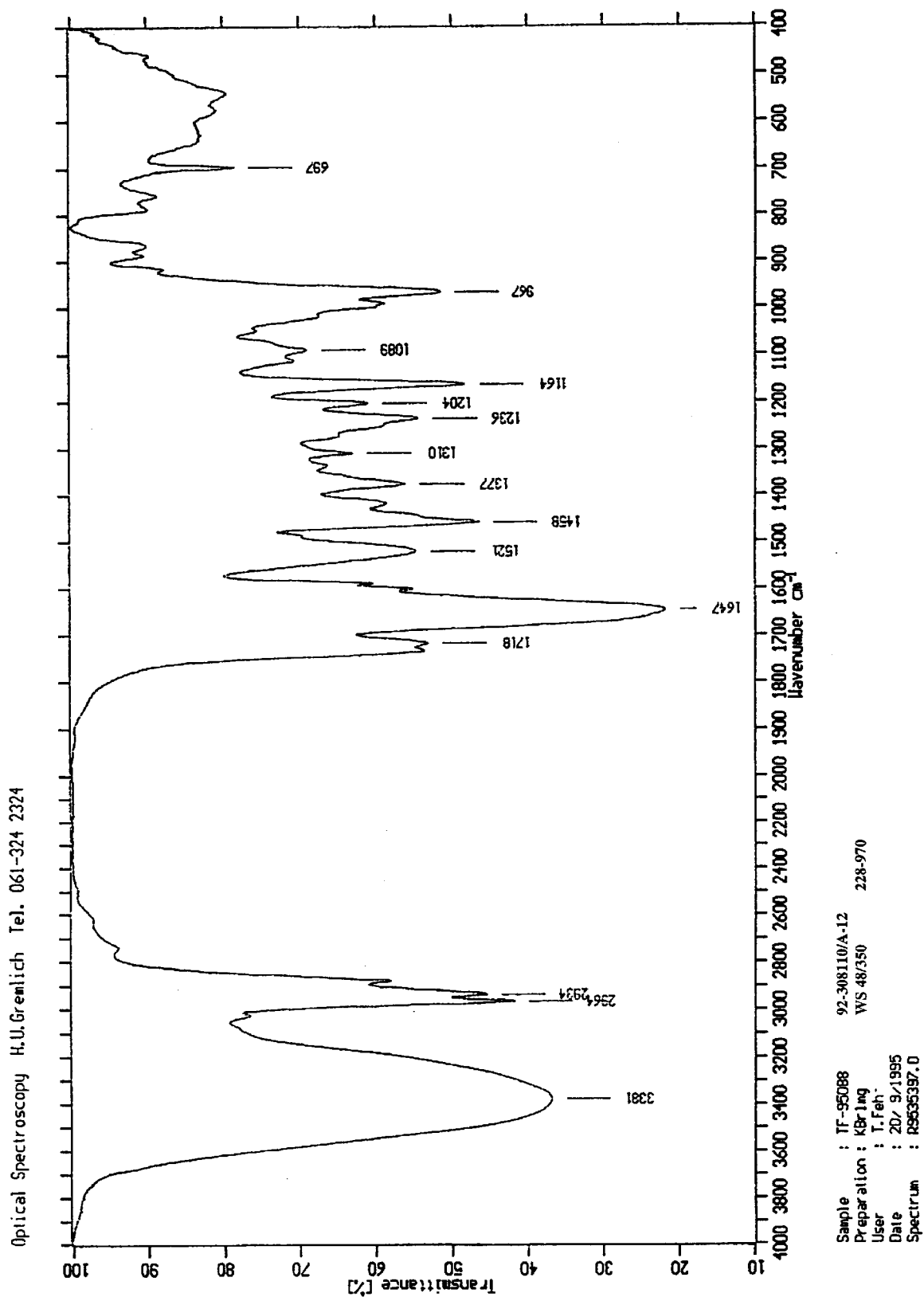
Figure 14:
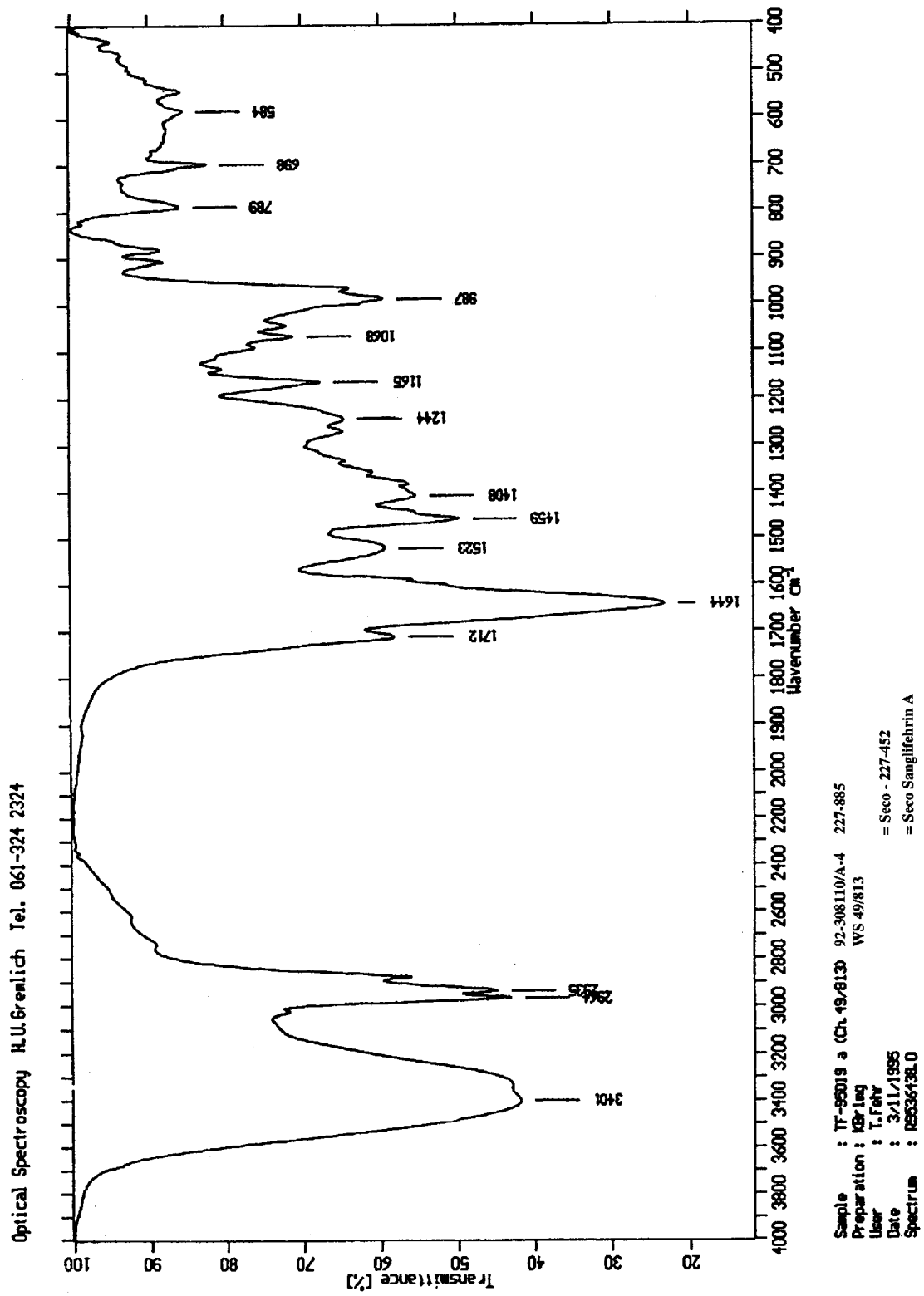
Figure 15:
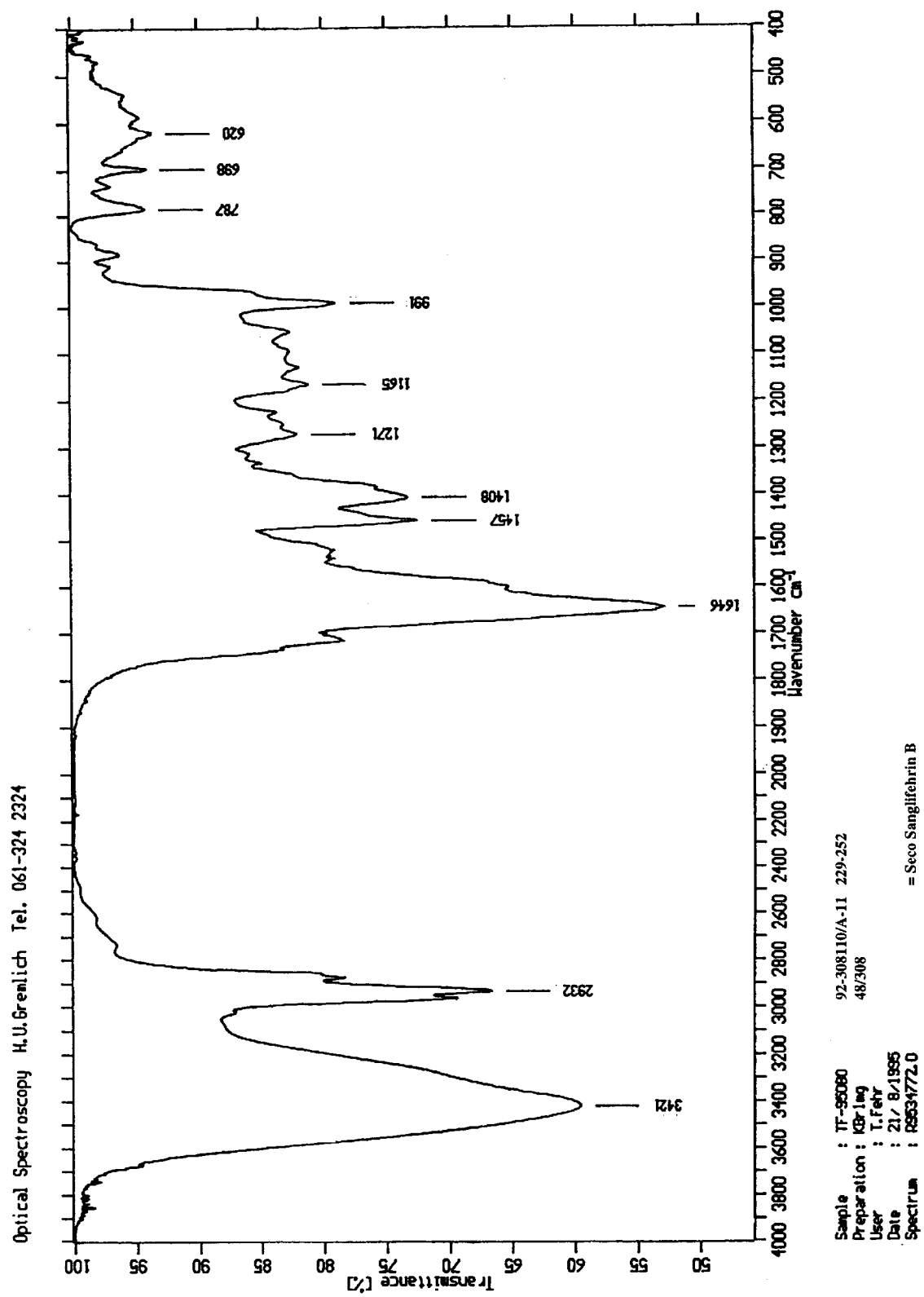
Figure 17:
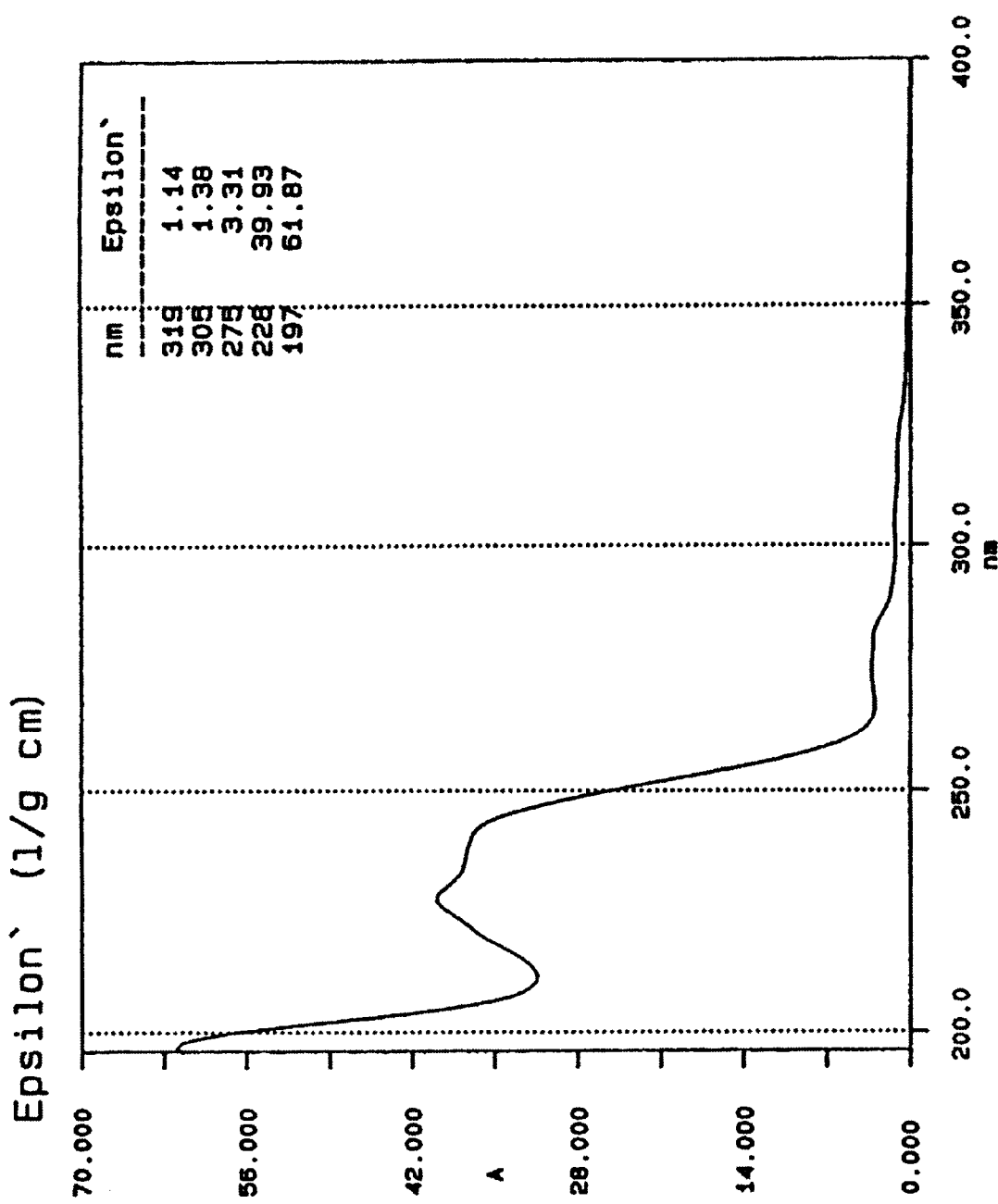
Figure 18:
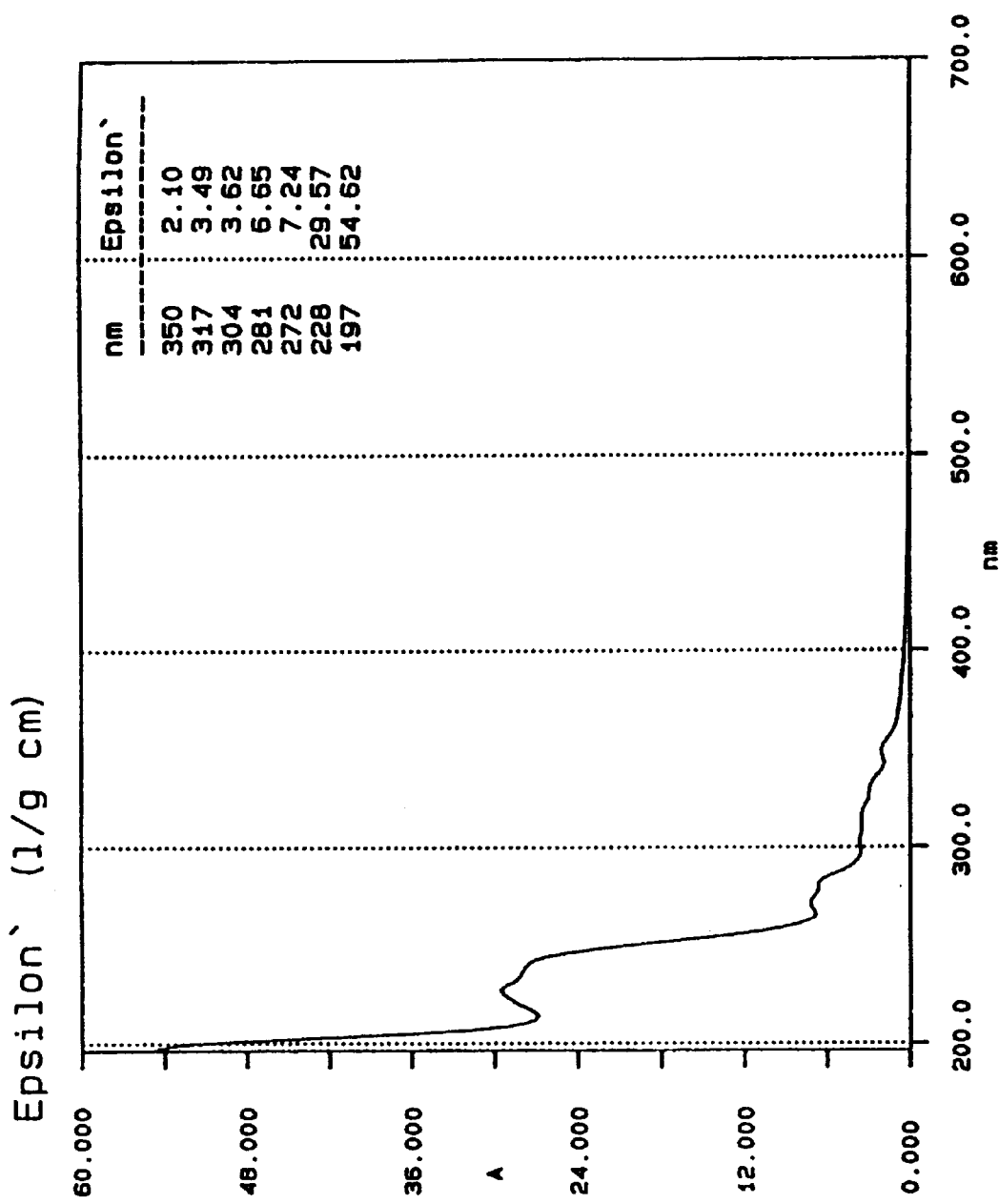
Figure 19:
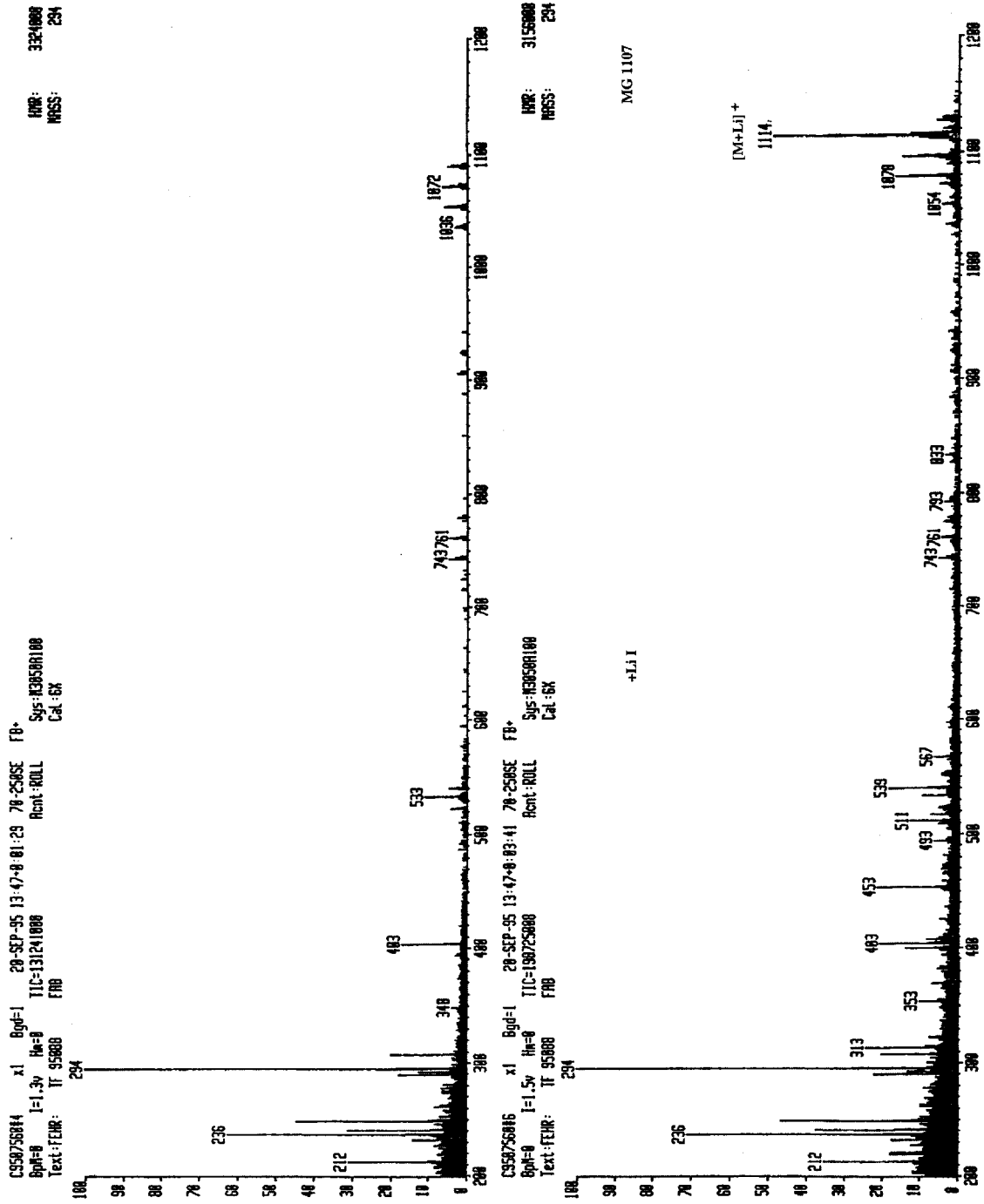
Figure 20:
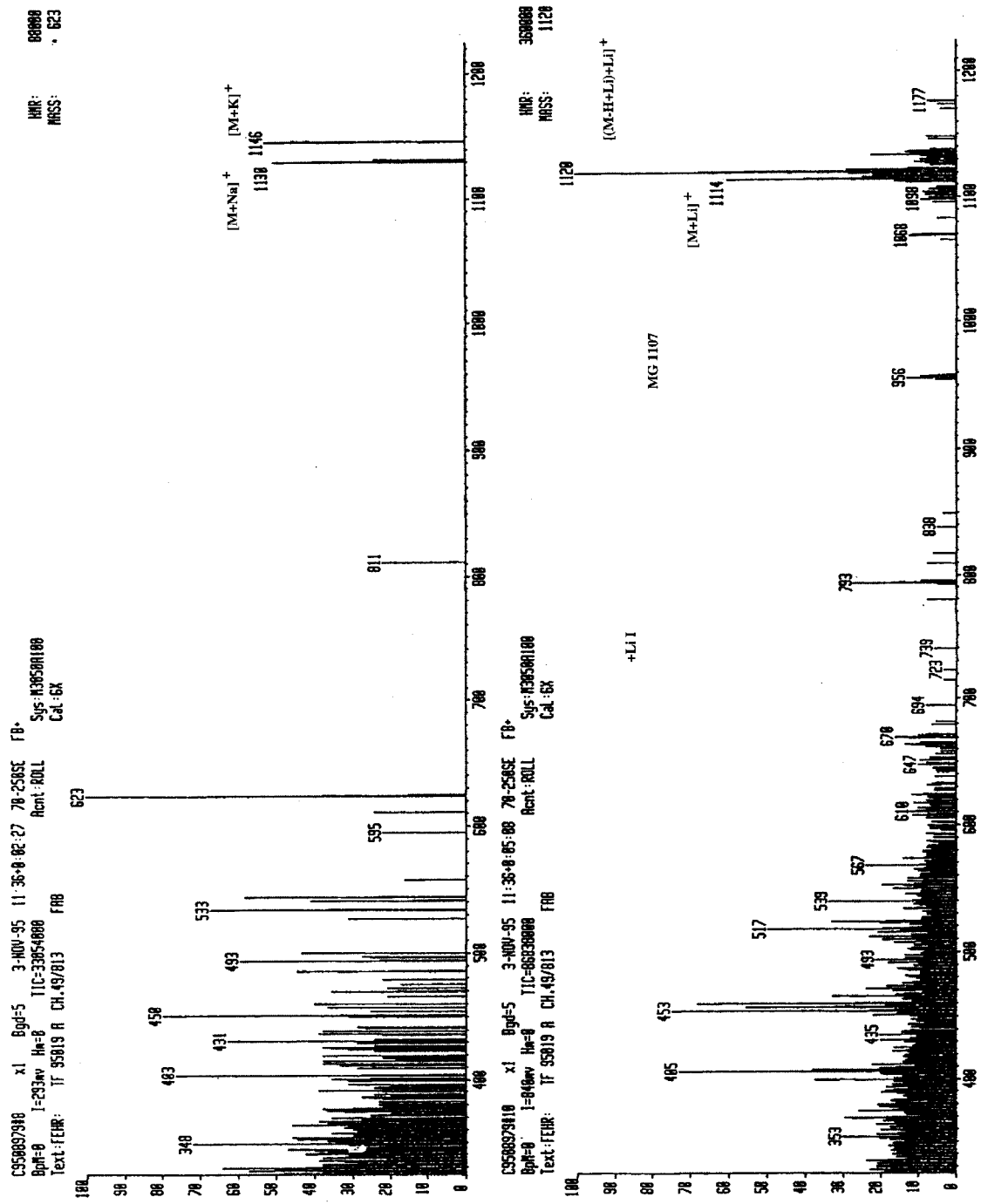
Figure 21:
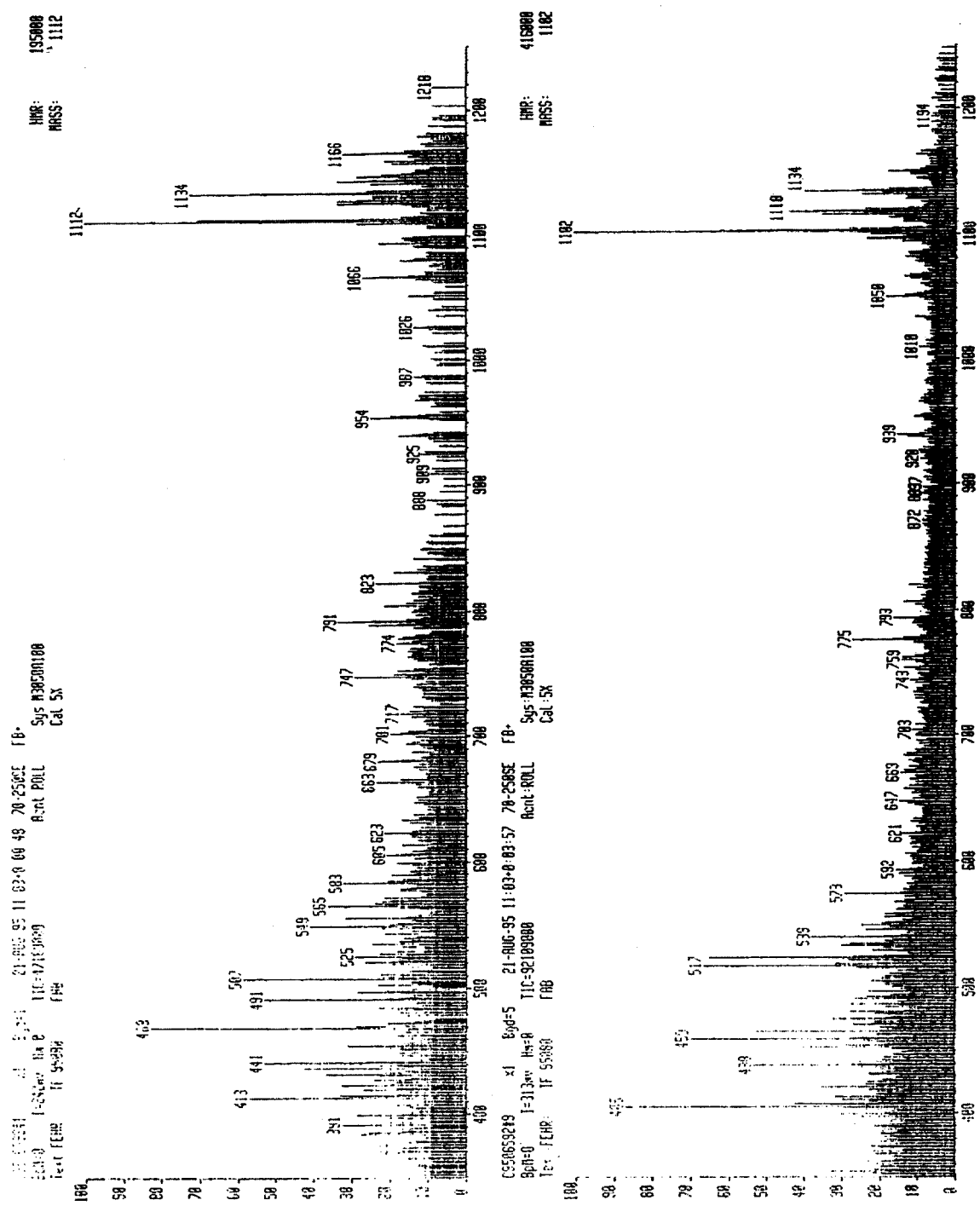

FIG. 1 shows the Mass spectrum of Sanglifehrin B;
FIG. 2 shows the Mass spectrum of Sanglifehrin A;
FIG. 3 shows the Mass spectrum of Sanglifehrin D;
FIG. 4 shows the Mass spectrum of Sanglifehrin C;
FIG. 5 shows the IR spectrum of Sanglifehrin B;
FIG. 6 shows the IR spectrum of Sanglifehrin A;
FIG. 7 shows the IR spectrum of Sanglifehrin D;
FIG. 8 shows the IR spectrum of Sanglifehrin C;
FIG. 9 shows the NMR spectrum of Sanglifehrin A;
FIG. 10 shows the NMR spectrum of Sanglifehrin D;
FIG. 11 shows the NMR spectrum of SanglifehrinB;
FIG. 12 shows the NMR spectrum of Sanglifehrin C;
FIG. 13 shows the IR spectrum of Sanglifehrin E;
FIG. 14 shows the IR spectrum of Seco-sanglifehrin A;
FIG. 15 shows the IR spectrum of Seco-sanglifehrin B;
FIG. 17 shows the UV spectrum of Sanglifehrin E;
FIG. 17 shows the UV spectrum of Seco-sanglifehrin A;
FIG. 18 shows the UV spectrum of Seco-sanglifehrin B;
FIG. 19 shows the Mass spectrum of Sanglifehrin E;
FIG. 20 shows the Mass spectrum of Seco-sanglifehrin A, and
FIG. 21 shows the Mass spectrum of Seco-sanglifehrin B.

EXAMPLES

Culture Conditions

Streptomyces sp. A 92-308110 may be cultured at suitable temperatures on various culture media using appropriate nutrients and mineral substances, using aerobic or immersion culture procedures. The fermentation media typically contains a utilisable source of carbon, sources of nitrogen and mineral salts including trace elements, all of which can be added in the form of well defined products or as complex mixtures, for instance as are found in biological products of various origins.

Example 1 describes the original conditions under which compounds of formula I were obtained. Improved yields may be obtained by optimisation of the culture conditions (aeration, temperature, pH, quality and quantity of the carbon and nitrogen sources, quantity of the mineral salts and of the trace elements) and by controlling the fermentation conditions in bioreactors.

Example 1

Culture of Strain A 92-308110 a. Agar Starting Culture

Agar slant cultures of the strain A 92-308110 are grown for 10 to 14 days at 27° C. on the following altar medium:

| | |
|---|---|
| Glucose | 10.0 g |
| Soluble starch | 20.0 g |
| Yeast extract | 5.0 g |
| (Gistex, Gist Brocades) | |
| NZ-Amine, Type A (Sheffield) | 5.0 g |
| Calcium carbonate | 1.0 g |
| Agar (Bacto) | 15.0 g |
| Demineralised water to 1000 ml | |

The medium is adjusted to pH 6.6–6.8 with NaOH/$H_2SO_4$, then sterilised for 20 min. at 121° C.

The cultures or cell suspensions can be stored, e.g. at −25°–70° C. in a protective medium, such as glycerol-peptone, e.g. under liquid nitrogen.

b Preculture

Spores and mycelium of 10 starting cultures are suspended in 100 ml of a 0.9% salt solution. Two 2 Liter-Erlenmeyer flasks each containing 1 liter of preculture medium are inoculated each with 50 ml of this suspension. The composition of the preculture medium is as follows:

| | |
|---|---|
| Glucose techn | 7.50 g |
| Glycerin | 7.50 g |
| Yeast extract (BBL) | 1.35 g |
| Malt extract liquid (Wander) | 7.50 g |
| Starch soluble | 7.50 g |
| NZ-Amine, Type A (Sheffield) | 2.50 g |
| Soya protein | 2.50 g |
| L(−) Asparagine | 1.00 g |
| $CaCO_3$ | 0.050 g |
| NaCl | 0.050 g |
| $KH_2PO_4$ | 0.250 g |
| $K_2HPO_4$ | 0.500 g |
| $MgSO_4 \cdot 7H_2O$ | 0.100 g |

-continued

| | |
|---|---|
| Trace element solution A | 1 ml |
| Agar (Bacto) | 1 g |
| Demineralised water to 1000 ml | |

The medium is adjusted to pH 6.8–7.2 with NaOH/H$_2$SO$_4$ and sterilised for 20 m at 121° C.

The composition of the trace element solution A is as follows:

| | |
|---|---|
| FeSO$_4$.7H$_2$O | 5.0 g |
| ZnSO$_4$.7H$_2$O | 4.0 g |
| MnCl$_2$.4H$_2$O | 2.0 g |
| CuSO$_4$.5H$_2$O | 0.2 g |
| CoCl$_2$.6H$_2$O | 2.0 g |
| H$_3$BO$_3$ | 0.1 g |
| KI | 0.05 g |
| H$_2$SO$_4$ (95%) | 1 ml |
| Demineralised water to 1000 ml | |

The precultures are fermented for 24 hr. at 27° C. on a rotary shaker at 200 rpm with an eccentricity of 50 mm.

c First Intermediate Culture

Two 75 Liter bioreactors containing each 50 liters of preculture medium are inoculated each with 1 liter of the preculture and fermented for 96 hr. at 27° C. The fermenter is rotated at 150 rpm. Air is introduced at a rate of 0.5 liter per minute per liter medium.

d Second Intermediate Culture

Two 750 liter fermentation vessels each containing 500 liters of the preculture medium are each inoculated with 50 liter of the first intermediate culture. The second intermediate cultures are incubated for 70 hr at 27° C. The fermenters are rotated at 100 rpm and air is intoduced at a rate of 0.8 liter per minute per liter medium.

e. Main Culture

Two 5'000 Liter bioreactors each containing 3'000 liters of the main medium are inoculated respectively with 250 and 300 liters of the second intermediate cultures. The main cultures are incubated during 96 hr at 24° C. The bioreactors are rotated at 45 rpm and air introduced at a rate of 0.5 liter per minute per liter medium.

The composition of the main culture medium is as follows:

| | |
|---|---|
| Glucose techn | 20 g |
| Malt extract liquid (Wander) | 2 g |
| Yeast extract (Bacto) | 2 g |
| Soytone (Bacto) | 2 g |
| KH$_2$PO$_4$ | 0.2 g |
| K$_2$HPO$_4$ | 0.4 g |
| MgSO$_4$.7H$_2$O | 0.2 g |
| NaCl | 0.05 g |
| CaCl$_2$.6H$_2$O | 0.05 g |
| Trace element solution B | 1 ml |
| Agar (Bacto) | 1 g |
| demineralised water to 1000 ml. | |

The pH is adjusted to 6.3 with KOH/HCl. The medium is sterilised for 20 min at 121° C.

The composition of the trace element solution B is the following:

| | |
|---|---|
| FeSO$_4$.7H$_2$O | 5.0 g |
| ZnSO$_4$.7H$_2$O | 4.0 g |
| MnCl$_2$.4H$_2$O | 2.0 g |
| CuSO$_4$.5H$_2$O | 0.2 g |
| (NH$_4$)$_6$ Mo$_7$O$_{24}$ | 0.2 g |
| CoCl$_2$.6H$_2$O | 1.0 g |
| H$_3$BO$_3$ | 0.1 g |
| KJ | 0.05 g |
| H$_2$SO$_4$ (95%) | 1 ml |
| Demineralised water to 1000 ml | |

An optimised culture medium for the main culture is as follows:

| | |
|---|---|
| Soybean meal | 20.0 g |
| Glycerol | 40.0 g |
| MES | 0.1M (2-{N-Morpholino} ethane sulfonic acid) |
| Demineralised water to 1000 ml at pH 6.8 | |

Example 2

Isolation of Sanglifehrins A, B, C and D from Streptomyces sp. A92-308110

The first isolation and characterization of the 4 new CBA active metabolites was done from two 3000 l tank fermentations by activity guided fractionation and HPLC and thin layer chromatographic analysis. CBA (cyclophilin binding assay) as described above was used to test for biological activity.

The two 3000 liter fermentations are processed separately. 1500 liter from each fermentation is stirred with 2000 l ethyl acetate in 4000 liter stainless steel vessel for 20 hours. The separation of the organic phase is done with a Westfalia-Separator typ SA-20. The ethyl acetate extracts are washed twice with 80 liters of water and evaporated to dryness under reduced pressure to give 1.64 and 2 kg extracts. The two crude extracts are defatted by a three step extraction with 40 liter methanol/water 9:1 and 40 liter of hexane. Evaporation to dryness under reduced pressure gives 1.34 kg extract.

The defatted extract is chromatographed in two portions (670 g) on a column of 10 kg Sephadex H in methanol solution. Each portion is dissolved in 3.3 liters of methanol when added to the column. After collection of the first 15 liters eluate as fraction 1 the chromatography is continued by collecting 2 liter fractions. The most active fractions were 2, 3 and 4 and are therefore combined to give 146 g. This sample is further chromatographed on 1 kg Silicalgel Merck 0.04–0063 mm with methyl-tertiary-butyl-ether (MTBE), MTBE/5% methanol and MTBE/10% methanol. Fractions of 2 liters are collected. Fractions 5 to 9 are the most active ones and are combined to give a sample of 43.8 g. This sample is further separated on a column of 1 kg Silicagel (Merck) 0.04–0.063 mm with a gradient of hexane/acetone 7:3 to acetone. From this chromatography fraction 6 (7.0 g) is further separated on a column of 3 kg Lichroprep RP 18 (Merck) 40–63 um with methanol/water 94:6 (fraction 4–7 2.16 g) then on a column of 100 g Silicagel H with methylenechloride and 3% methanol (733 mg), a column of 3 kg Lichroprep RP18 with methanol/water 9:1 (621 mg) and then on 100 g Lichroprep RP18 with acetonitrile/water 1:1 to yield 324 mg of pure Sanglifehrin A (mp 142–145° C. (amorphous), $(\alpha)^D{}_{25}$=−67.30 (c=0-988, methanol)).

Fractions 5 and 7 from the hexane/acetone column are combined (7.1 g) and further purified on a column of 3 kg Lichroprep RP18 40–63 μm with methanol/water 9:1 (769 mg), on a column of 100 g silicagel H with MTBE 3% methanol (309 mg) and finally on 100 g silicagel H with methylenechloride and 3% methanol to yield 90 mg pure Sanglifehrin B (mp. 117–121° C. (amorphous), $(\alpha)^D{}_{25}$=−52.80 (c=1-128 in methanol)).

Fractions 9 and 10 (2.147 g) of the chromatogramm with methanol/water 94:6 on 3 kg Lichroprep RP18 are further purified on 100 g Silicagel H with methylenechloride/5% methanol (800 mg) and finally on 3 kg Lichroprep RP18 with methanol/water 9:1 to give 480 mg of Sanglifehrin C (mp. 165–170° C., $(\alpha)^D{}_{25}$=−35.60 (c=0-736 in methanol).

Fractions 11 and 12 (835 mg) of the chromatogramm with methanol/water 94:6 on 3 kg Lichroprep RP18 are purified on 100 g Silicagel H with MTBE/5% methanol to give 140 mg of Sanglifehrin D (mp. 137–142° C., amorphous).

Sanglifehrin A, B, C and D are then characterised by UV, IR, Mass and NMR spectroscopy. The results obtained are given in Table 4 below and in the accompanying FIGS. 1–12.

TABLE 4

Sanglifehrin A

| | |
|---|---|
| molecular formula: | $C_{60}H_{91}N_5O_{13}$ (1090.4) |
| UV (MeOH): | 275 (1962), 242 (54500), 197 (75755) |
| H⁺: | 275 (1635), 242 (51884), |
| OH⁻: | 292 (1973), 242 (60495) |
| IR-spectra: | FIG. 6 |
| Mass-spectra: | FIG. 2 |
| FAB 1096[MH + Li]⁺: | |
| NMR spectra: | FIG. 9 |

Sanglifehrin B

| | |
|---|---|
| molecular formula: | $C_{60}H_{89}N_5O_{12}$ (1072.4) |
| UV (MeOH): | 273 (4395), 242 (50600), 197 (78577) |
| IR-spectra: | FIG. 5 |
| Mass-spectra: | FIG. 1 |
| FAB 1098[MH + Li]⁺: | |
| NMR spectra: | FIG. 11 |

Sanglifehrin C

| | |
|---|---|
| molecular formula: | $C_{61}H_{93}N_5O_{13}$ (1104.4) |
| UV (MeOH): | 275 (1876)), 242 (51557), 197 (72643) |
| H⁺: | 275 (1391), 242 (50120) |
| OH⁻: | 292 (1832), 242 (57960) |
| IR-spectra: | FIG. 8 |
| Mass-spectra: | FIG. 4 |
| FAB 1110[MH + Li]⁺: | |
| NMR spectra: | FIG. 12 |

Sanglifehrin D

| | |
|---|---|
| molecular formula: | $C_{61}H_{91}N_5O_{12}$ (1086.4) |
| UV (MeOH): | 273 (3194), 242 (47584), 197 (73766) |
| H⁺: | 273 (3237), 242 (46389) |
| OH⁻: | 285 (2600), 242 (52907) |
| IR-spectra: | FIG. 7 |
| Mass-spectra: | FIG. 3 |
| FAB 1092[MH + Li]⁺: | |
| NMR spectra: | FIG. 10 |

In addition Sanglifehrin E and Seco-sanglifehrins A and B are analogously isolated from cultures of sp. A92-308110.

Sanglifehrin E

Figure 16:
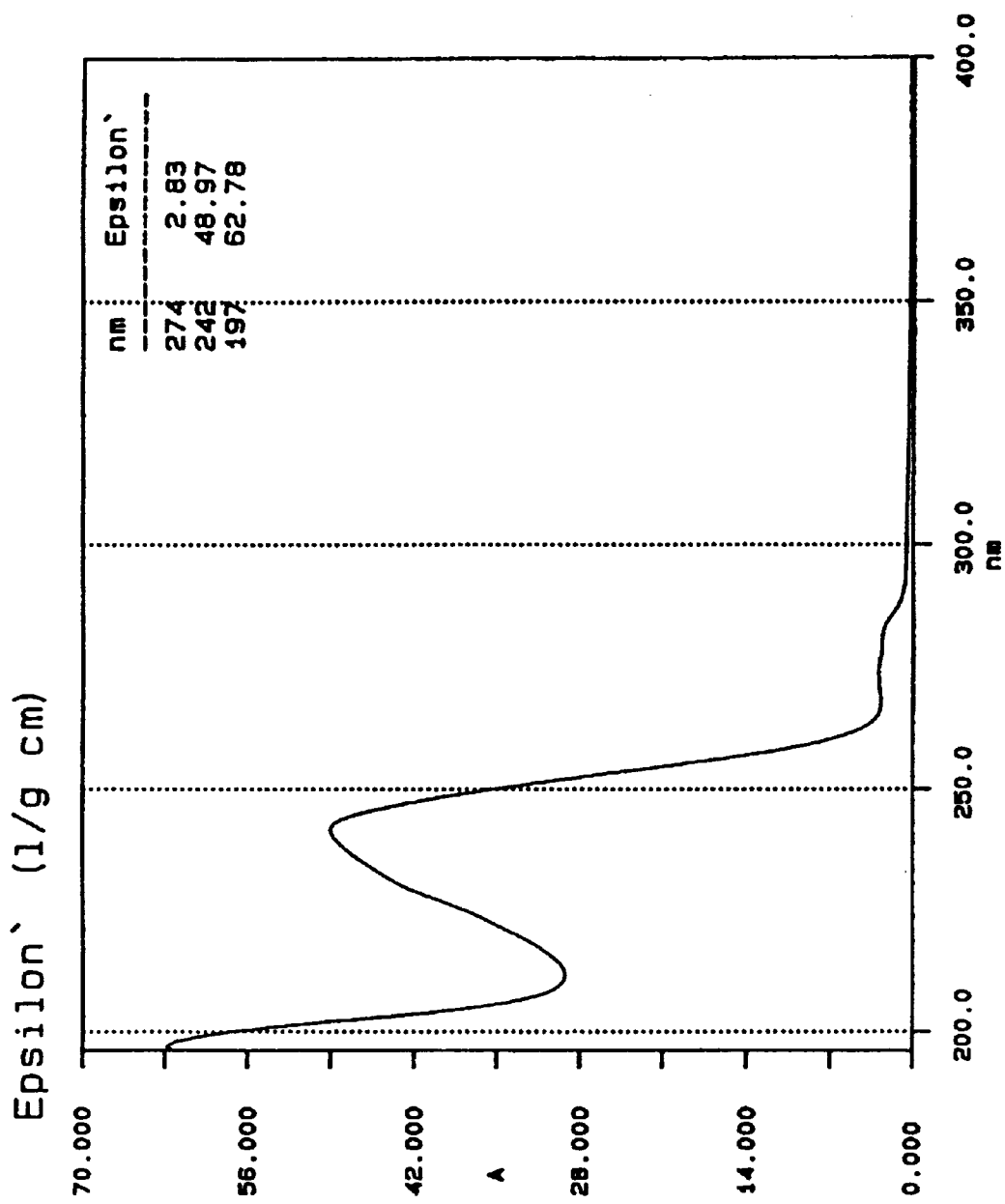

During the large scale fermentation and purification of Sanglifehrin A as described above, 91 g of crude product obtained from the Sephadex column is chromatographed on a column of 1 kg Silicagel Merck 0.040 to 0.063 μm with hexane, acetone 7:3, 5:5, 3:7, 2:8, 1:9, acetone and methanol. Fractions of 2 l are collected. The fractions containing the sanglifehrins, fractions 4 to 6 21.3 g, are further separated on a column of 3 kg Lichroprep RP18 Merck, with methanol/water 8:2. Beside the fractions with Sanglifehrin A and Sanglifehrin B, fraction 3, 1.6 g was analysed by HPLC and TLC and found to contain a new sanglifehrin-like compound. Final purification, on a column of 100 g Silicagel H with ethyl acetate saturated with water as eluent, yielded 360 mg sanglifehrin E. mp. 131–135° C. amorph, $(\alpha)_D{}^{20}$=−55.7° (c=0.998, methanol). The IR-, UV- and MS-spectra of this product are given in FIGS. 13, 16 and 19 respectively.

Secosanglifehrin A 670 g defatted extracts from two 3000 l fermentations, as described above, are chromatographed on 10 kg Sephadex LH20 with methanol. The sanglifehrin containing fractions were combined to give 150 g of crude product. Further chromatography on 1 kg Silicagel Merck MTBE, MTBE 10% methanol elutes Sangliferins A and B. Washing of the column with 5 l methanol yields 71 g fraction 1 1.

15 g of this fraction are further chromatographed on 150 g Silicagel with ethyl acetate/methanol 95:5, 90:10, 85:15, 80:20, 70:30 and fractions of 1 l collected. Fractions 6 to 8 are combined (5.7 g) and further purified by chromatographic steps on 3 kg Lichroprep RP18 with methanol/water 75:25 and 1 kg Sephadex LH20 in methanol to give 511 mg, pure secosanglifehrin A. The IR-, UV- and MS-spectra of this product are given as FIGS. 14, 17 and 20 respectively.

Secosanglifehrin B

From two 50 l fermentations, the defatted extract (18 g) is chromatographed on 1 kg, Sephadex LH20 to give a 3.5 g sanglifehrin-containing fraction. Separation on a column of 3 kg Lichroprep RP 18 Merck 40–60 μm with methanol/water (no pressure) yields 272 mg of a mixture of sanglifehrins. Further separation is done on a 20×20 cm preparative layer chromatography plate with methylene chloride/methanol/water 92:7.7:0.5 three times running. The plate is separated into three zones. The most polar zone is eluted with methanol and once more chromatographed on a preparative layer chromatography plate with methylene chloride/methanol/water 80:17.5:2. The zone with the new compound is eluted to yield 30 mg, of secosanglifehrin B. The IR-, UV- and MS-spectra of this product are given as FIGS. 15, 18 and 21 respectively.

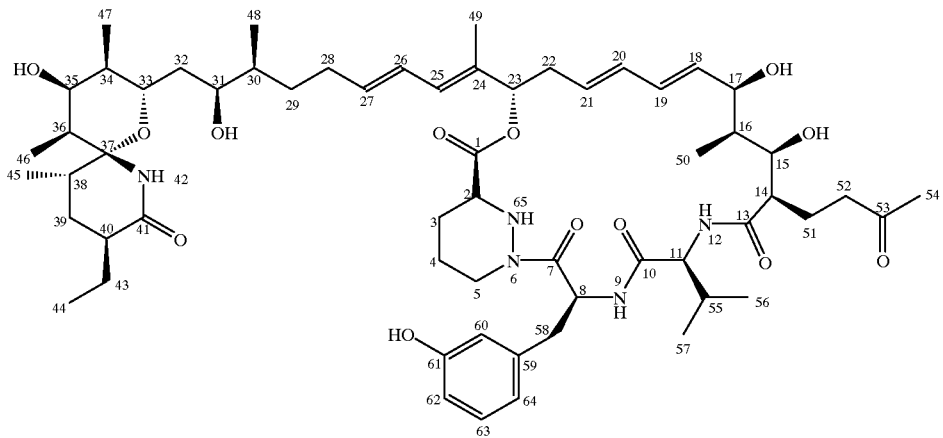

Sanglifehrin A

Example 3

Transformation of Sanglifehrin A into Sanalifehrin C

To a stirred, cooled (0° C.) solution of 20 mg (18.3 μmol) of Sanglifehrin A in 0.5 mL of methanol is added one crystal of paratoluenesulfonic acid monohydrate. The resulting yellow solution is stirred for one hour and the reaction is quenched with saturated aqueous sodium bicarbonate solution. The resulting mixture is extracted twice with ethyl acetate. The organic solution is washed twice with saturated brine, dried over anhydrous sodium sulfate, filtered and concentrated under reduced pressure. The residue is purified by column chromatography on silica gel (95:5 methyl-tert.-butyl ether:methanol) to yield Sanglifehrin C as a white amorphous powder. The latter consisted of a 4:1 mixture of Sanglifehrin C and its C53 epimer, Sanglifehrin C having the (S) configuration as depicted below (R=Me).

paratoluenesulfonate, hydrochloric acid or sulfuric acid) or Lewis acids (such as zinc chloride, magnesium bromide or chloride, titanium tetraisopropoxide or boron trifluoride) in methanol. Use of other alcoholic solvents or cosolvents like ethanol, isopropanol, butanol, allyl alcohol, propargyl alcohol, benzyl alcohol lead in the same manner to analogues where R in the structure above is respectively ethyl, isopropyl, butyl, allyl, propargyl, benzyl.

In the same manner as described above, Sanglifehrin B can be transformed into Sanglifehrin D.

Example 4

Transformation of Sanglifehrin C into Sanglifehrin A

A solution of 550 mg (0.50 mmol) of sanglifehrin C in 5 mL of 4:1 THF-water is treated with 0.5 mL of 2N aqueous sulfuric acid and stirred for 1.5 h. The reaction is quenched 4:1 mixture of diastereomers

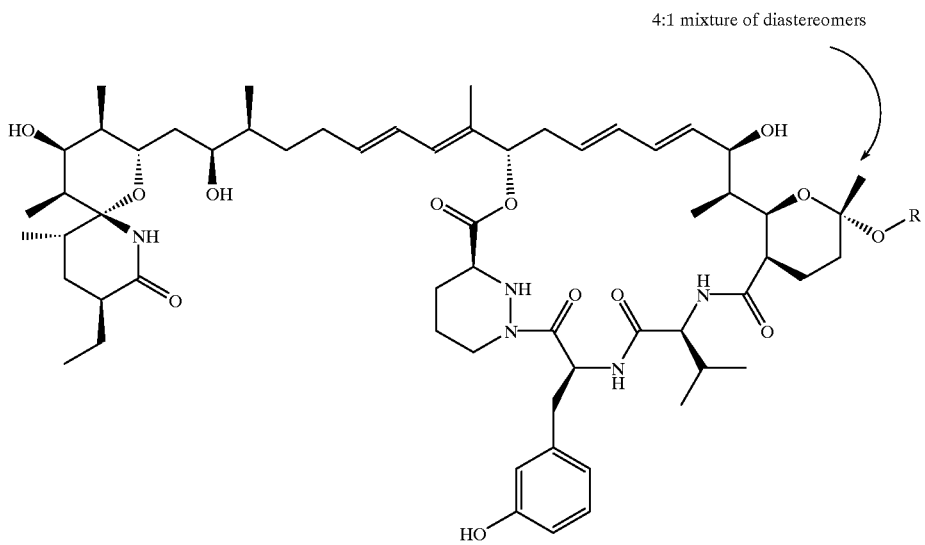

Alternatively, this transformation can be carried out by using other protic acids (such as pyridinium with saturated aqueous sodium bicarbonate and the resulting mixture is extracted twice with ethyl acetate. The organic solution is washed with saturated aqueous sodium bicarbonate solution and twice with saturated brine, dried over anhydrous sodium sulfate, filtered and concentrated under reduced pressure. The residue is purified by column chromatography on silica gel (90:10 methyl-tert.-butyl ether:methanol) to yield sanglifehrin A as a white amorphous powder.

Other inorganic or organic acids can be used in a medium containing water and optionally an organic cosolvent. Suitable acids include hydrochloric acid, paratoluenesulfonic acid or other sulfonic acids, pyridinium paratoluenesulfonate, acetic acid, trifluoroacetic acid, formic acid. Suitable organic cosolvents are acetonitrile. dimethylformamide, dimethylsulfoxide, dioxane.

These reactions are accompanied by the formation of varying amounts of the compound of formula XVI, depending among others on the reaction time (for a better procedure leading to the compound of formula AVI see Example 5 below). Analogously, sanglifehrin D can be transformed into sanglifehrin B.

Example 5

Transformation of Sanglifehrin A into the compound of formula XVI

To a stirred, cooled (0° C.) solution of 50 mg (46 μmmol) of sanglifehrin A in 1.9 mL of acetonitrile is added 0.1 mL of hydrogen fluoride-pyridine. The resulting yellow solution is stirred for 1 hour and the reaction is quenched with saturated aqueous sodium bicarbonate. The resulting mixture is extracted twice with ethyl acetate. The organic solution is washed twice with saturated brine, dried over anhydrous sodium sulfate, filtered and concentrated under reduced pressure. The residue is purified by column chromatography on silica gel (95:5 methyl-tert.-butyl ether:methanol) to yield the compound of formula XVI as a white amorphous powder.

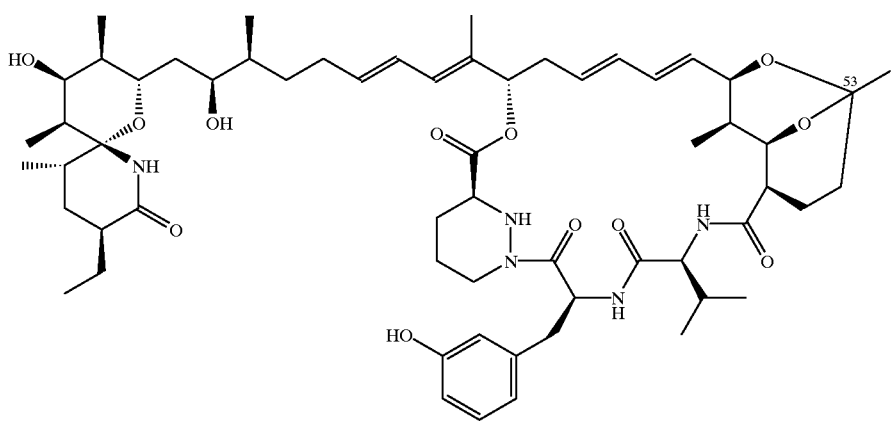

XVI

In an analogous manner sanglifehrin B can be transformed into the compound of formula XVII. These substances exist as a single epimer at C53, but the absolute configuration has not been unambiguously determined.

pressure. Column chromatography of the residue on silica gel gel (90:10 methyl-tert.-butyl ether:methanol) yields sanglifehrin A as a white amorphous solid.

Analogously the compound of formual XVII can be transformed into Sanglifehrin B.

XVII

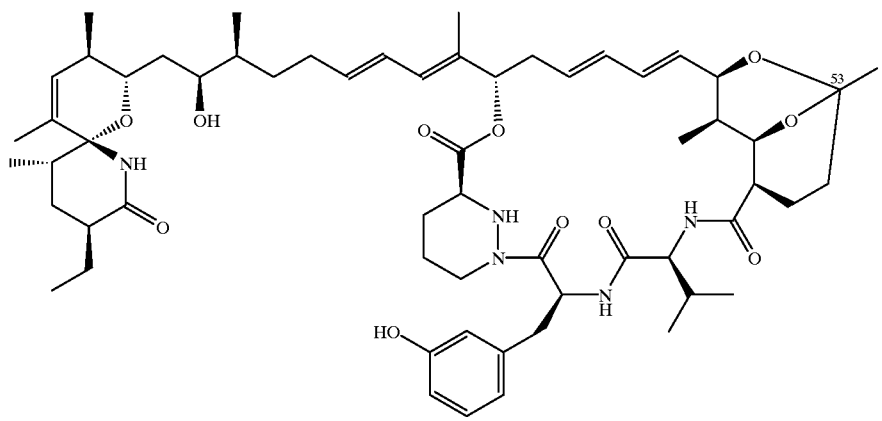

Formula XVI: MS m/z 1078 [M+Li]$^+$(rel. intensity 100); $^1$H NMR (DMSO) (only characteristic signals listed) δ0.40 (3H, d, H-50), 1.20 (3H, s, H-54), 1.69 (3H, s, H-49), 4.20 (1H, t, H-15), 4.58 (1H, dd, H-17), 5.19 (1H, dd, H-18), 5.28 (1H, dd, H-23), 5.62 (1H, m, H-21), 5.67 (1H, m, H-27), 5.99 (1H, d, H-25), 6.03 (1H, dd, H-19), 6.14 (1H, dd, H-20), 6.22 (1H, dd, H-26).

Example 6

Transformation of the compound of formula XVI into Sanglifehrin A

To a stirred solution of 54 mg (50 μmol) of the compound of formula XVI in 0.5 mL of 4:1 THF-water is added 50 μL of 2N aqueous sulfuric acid. The resulting solution is stirred at ambient temperature for 12 hours and the reaction is quenched with saturated aqueous sodium bicarbonate solution. This mixture is extracted twice with ethyl acetate. The combined organic solution is washed with saturated aqueous sodium bicarbonate solution and brine, dried over anhydrous sodium sulfated, filtered and concentrated under educed The procedures described in examples 3 to 6 can be used as selective intramolecular protection-deprotection sequences. Thus, by the reaction described in example 5, the hydroxyl at position 15 can be selectively protected, which allows the selective manipulation of the remaining free hydroxyls. The procedure in example 5 allows for the selective protection of both the hydroxyls in the 15 and 17 positions. Both procedures can also be used as an intramolecular protection of the C53 ketone. The hydroxyls and the ketone can be regenerated by the reactions described in 4 and 6. Sanglifehrins C and D, as well as the compounds of formulae XVI and XVII are therefore important intermediates for the generation of further sanglifehrins.

Example 7

Preparation of 16-Dehydro-17-Dehydroxy-sanglifehrin A (Formula XVIII)

XVIII

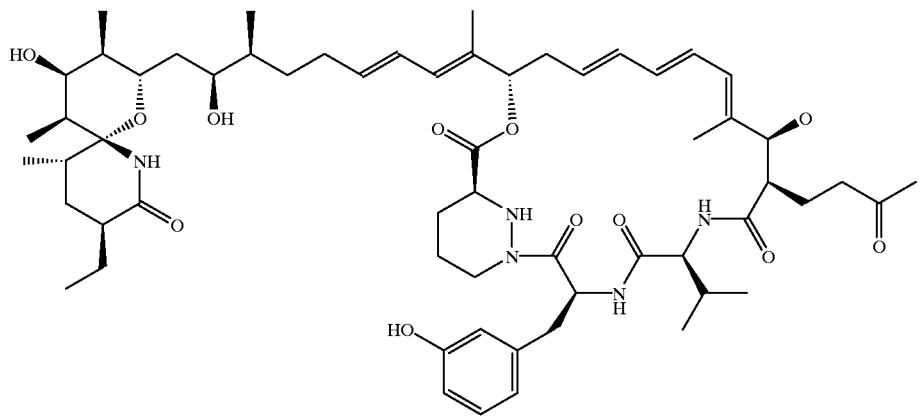

A solution of 54 mg (50 μmol) of the compound of formula XVI and a crystal of paratoluenesulfonic acid monohydrate in 1 mL of 4:1 acetonitrile-water is heated to 80° C. for 1.5 hours. The reaction is quenched by the addition of saturated aqueous sodium bicarbonate solution. The resulting mixture is extracted twice with ethyl acetate. The organic layer is washed with saturated aqueous sodium bicarbonate and brine, dried over anhydrous sodium sulfate, filtered and concentrated. The residue is purified by column chromatography on silica gel (90:10 methyl-tert.-butyl ether:methanol), followed by reverse phase chromatography (RP18, 50:50 acetonitrile-water to acetonitrile over 45 minutes) to yield the pure title compound as a white amorphous solid.

MS m/z 1078 [M+Li]+ (rel. intensity 100); $^1$H NMR (DMSO) (only characteristic signals listed) δ1.58 (3H, s, H-50), 1.71 (3H, s, H-49), 2.08 (3H, s, H-54), 4.03 (2H, d, H-15 and C31-OH), 5.57 (2H, m, H-21 and C35-OH), 5.72 (1H, dt, H-27), 5.96 (1H, d, C15-OH), 6.03 (1H, d, H-25), 6.09–6.28 (4H, m, H-18, H-19, H-20 and H-26), 6.37 (1H, d, H-17).

Example 8

Preparation of 42-N-methyl-Sanglifehrin A
(Formula XIX)

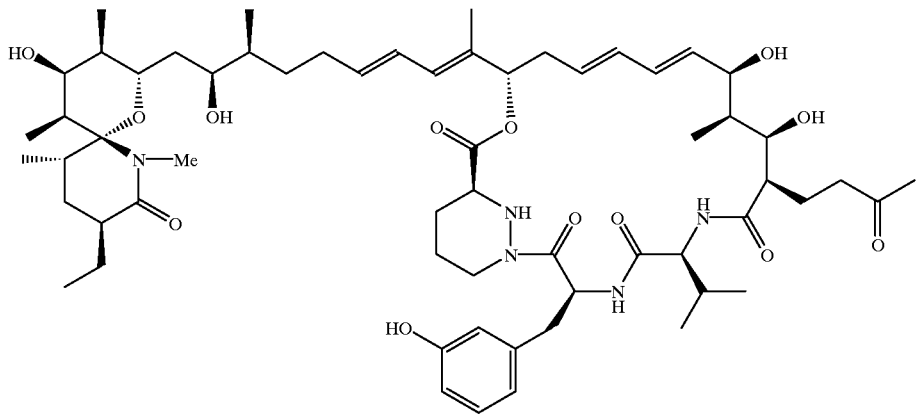

XIX

To a stirred, cooled (−15° C.) solution of 109 mg (0.1 mmol) of sanglifehrin A and 67 μL (0.3 mmol) of 2,6-di-tert.-butylpyridine in 1 mL of methylene chloride is added 16.5 μL of methyl triflate. The mixture is allowed to warm to room temperature and stirring is continued for six hours, after which the reaction is quenched by addition of saturated aqueous sodium bicarbonate solution. The resulting mixture is extracted twice with ethyl acetate. The organic layer is washed with brine, dried over anhydrous sodium sulfate, filtered and concentrated. The residue is purified by two-successive chromatographies on silica gel (90:10 methyl-tert.-butyl ether:methanol then 95:5 methyl-tert.-butyl ether:methanol) to yield the pure title compound as a white amorphous solid.

MS m/z 1110 [M+Li]⁺ (rel. intensity 100); ¹H NMR (DMSO) (only characteristic signals listed) δ1.70 (3H, s, H-49), 2.06 (3H, s, H-54), 3.53 (3H, s, 42 N—Me), 3.98 (1H, d, C31-OH), 4.50 (1H, d, H-65), 4.77 (1H, d, C17-OH), 5.43 (1H, d, C15-OH), 5.49(1H, d, C35-OH), 7.50 (1H, d, H-12), 8.11 (1H, d, H-9), 9.22 (1H, s, C61-OH).

purified by chromatography on silica gel (95:5 methyl-tert.-butyl ether:methanol followed by 90:10 methyl-tert.-butyl ether:methanol) to yield the pure title compound as a white amorphous solid. The isolated product corresponds to a ca. 1:1 mixture of diastereoisomers at C-53)

Example 9

Preparation of 53 Dihydro sanglifehrin A (Formula XX)

MS m/z 1098 [M+Li]⁺ (rel. intensity 63), 1104 [M+2Li-H]⁺+(rel. intensity 100); ¹H NMR (DMSO) (only characteristic signals listed) δ0.62 (3H, d, H-50), 1.02 (3H, d, H-54), 3.55 and 3.59 (1H, 2 m, H-53).

XX

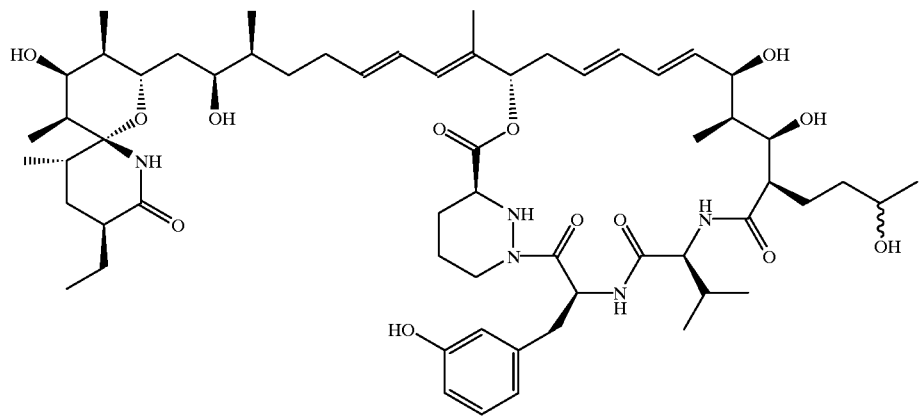

To a stirred, cooled (0° C.) solution of 54 mg (50 μmol) of sanglifehrin A in 0.5 mL of methanol is added 2.8 mg (75 μmol) of sodium borohydride. Stirring is continued for one hour and saturated aqueous sodium bicarbonate is added. The mixture is extracted twice with ethyl acetate. The organic solution is washed with brine, dried over anhydrous sodium sulfate, filtered and concentrated. The residue is Example 10

Preparation of 53- Tosylhydrazone-Sanglifehrin A (formula XXI)

XXI

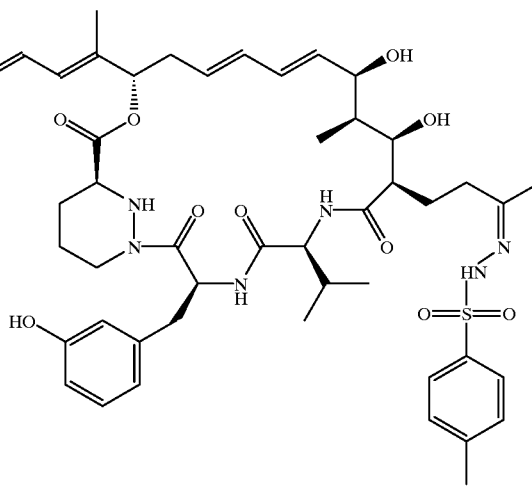

A mixture of 55 mg (50 μmol) of sanglifehrin A and 23 mg (125 μmol) of tosylhydrazide in 0.5 mL of methylene chloride is stirred at room temperature for six hours. The solvent is removed and the residue is purified by chromatography on silica gel (90:10 methyl-tert.-butyl ether:methanol) to yield the title compound as a white amorphous powder.

MS m/z 1264 [M+Li]$^+$ (rel. intensity 100); $^1$H NMR (DMSO) (only characteristic signals listed) δ1.70 (3H, s, H-49), 1.77 (3H, s, H-54), 2.37 (3H, s, -NSO$_2$C$_6$H$_4$CH$_3$), 6.51 (1H, s, H-60), 6.59 (2H, 2d, H-62 and H-64), 7.06 (1H, dd, H-63), 7.35 (2H, d, tosyl meta protons), 7.73 (2H, d, tosyl para protons).

Example 11

Preparation of 26S,27S-Dihydroxy-sanglifehrin A (Formula XXII) and 26R,27R-Dihydroxy-sanglifehrin A (Formula XXIII)

extracted twice with ethyl acetate. The combined organic layer is washed with saturated aqueous sodium bicarbonate and brine, dried over anhydrous sodium sulfate, filtered and concentrated. The residue is purified by reverse phase chromatography (RP18, 30:70 acetonitrile-water to acetonitrile over 60 minutes) yielding the 26S,27S-diol as an amorphous powder.

The corresponding 26R,27R-diol is obtained by the above procedure, but using (DHQD)$_2$PHAL instead of (DHQ)$_2$PHAL.

26S,27S-diol: MS m/z 1130 [M+Li]$^+$ (rel. intensity 100); $^1$H NMR (DMSO) (only characteristic signals listed) δ1.64 (3H, s, H-49), 2.06 (3H, s, H-54), 3.20 (1H, broad m, H-27), 3.45 (1H, broad m, H-31), 3.94 (3H, m, H-17, H-26 and C31-OH), 4.30 (1H, d, C27-OH), 4.57 (1H, d, C26-OH), 5.20 (1H, t, H-23), 5.33 (1H, d, H-25), 5.57 (3H, m, H-18, H-21 and C35-OH), 6.03 (1H, dd, H-19), 6.14 (1H, dd, H-20). 26R,27R-diol: MS m/z 1130 [M+Li]$^+$ (rel. intensity 100); $^1$H NMR (DMSO) (only characteristic signals listed)

XXII

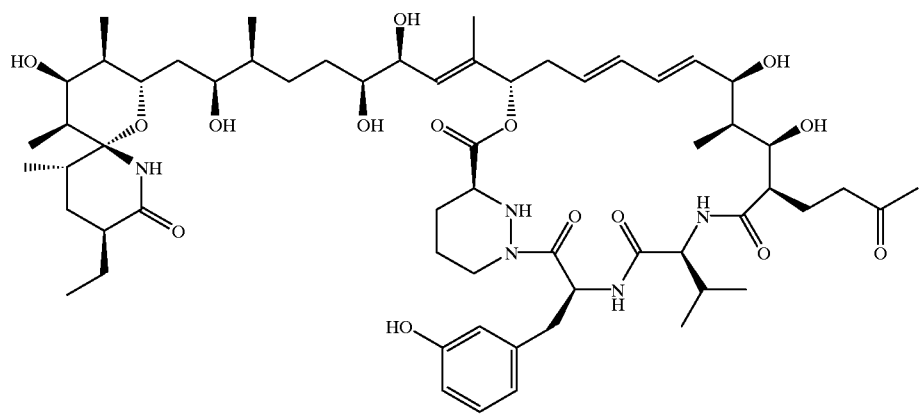

XXIII

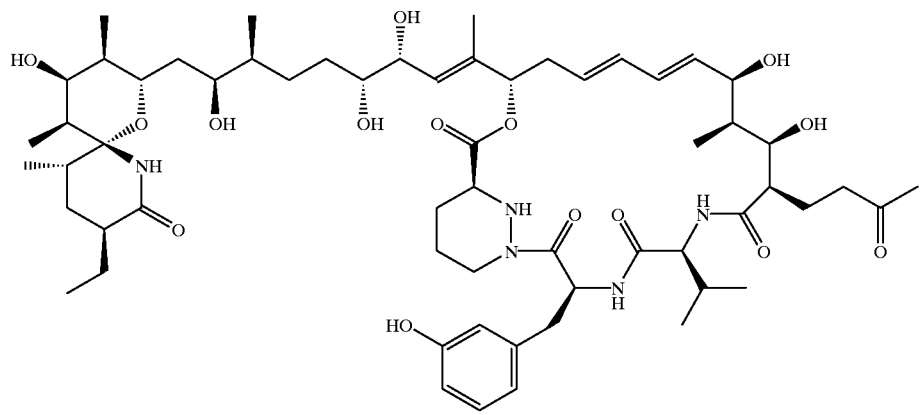

To a stirred, cooled (0° C.) solution of 495 mg (1.5 mmol) of potassium ferricyanide, 207 mg (1.5 mmol) of potassium carbonate, 19.5 mg (0.025 mmol) of (DHQ)$_2$PHAL, 65 μL (0.005 mmol) of 0.08 M osmium tetroxide in t-butanol and 95 mg (1 mmol) of methyl sulfonamide in 2.5 mL of t-butanol and 5 mL of water is added a solution of 545 mg (0.5 mmol) of sanglifehrin A in 2.5 mL of t-butanol. The resulting biphasic mixture is allowed to warm to room temperature and stirred for three hours. Then 1.08 g (8.6 mmol) of sodium sulfite is added, followed by ethyl acetate and water, and the mixture is vigorously stirred for 15 minutes. The layers are separated and the aqueous layer is δ1.64 (3H, s, H-49), 2.06 (3H, s, H-54), 3.16 (1H, broad m, H-27), 3.48 (1H, broad m, H-31), 3.94 (3H, m, H-17, H-26 and C31-OH), 4.30 (1H, d, C27-OH), 4.57 (1H, d, C26-OH), 5.20 (1H, dd, H-23), 5.35 (1H, d, H-25), 5.57 (3H, m, H-18, H-21 and C35-OH), 6.03 (1H, dd, H-19), 6.14 (1H, dd, H-20).

Example 12

Cleavage of the diol in 26S,27S-Dihydroxy-sanglifehrin A

To a solution of 90 mg (79 μmol) of the 26S,27S diol in 0.9 mL of 2:1 THF-water is added 33.7 mg (157 μmol) of sodium periodate. Stirring is continued for one hour and saturated aqueous sodium bicarbonate is added. The mixture is extracted twice with ethyl acetate. The organic solution is washed with brine, dried over anhydrous sodium sulfate, filtered and concentrated. Purification of the residue on silica gel (95:5 methyl-tert.-butylether:methanol) yields the compounds of formula XXIV (foam) and XXV (powder).

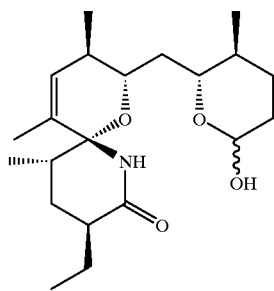

XXIV

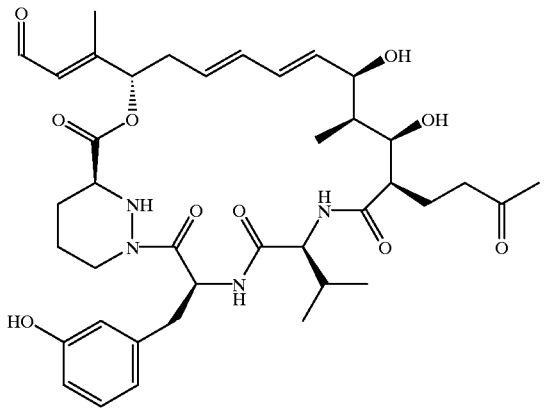

XXV formula XXIV: MS m/z 366 [M+H–H$_2$O]$^+$ (rel. intensity 100); $^1$H NMR (DMSO) (2:1 mixture of OH$_{ax}$:OH$_{eq}$ epimers at the anomeric center) (only characteristic signals listed) δ3.54 and 4.08 (1H, 2m, H-31), 3.57 (1H, broad m, H-35), 3.66 (1H, m, H-33), 4.38 (0.67H, ddd, H-27$_{ax}$), 4.95 (0.33H, broad m, H-27$_{eq}$), 5.40 (0.33H, d, C27-OH$_{eq}$), 5.59 (0.33H, d, C35-OH), 5.61 (0.67H, d, C35-OH), 5.96 (0.67H, d, C27-OH$_{ax}$), 7.89 (0.67H, s, NH-42), 7.91 (0.33H, s, NH-42).

formula XXV: MS m/z 745 [M+Li]$^+$ ; $^1$H NMR (DMSO) (only characteristic signals listed) δ0.64 (3H, d, H-50), 0.81 (6H, d, H-56 and H-57), 2.06 (3H, s, H-54), 2.17 (4H, s, H-14 and H-49), 3.80 (1H, broad m, H-15), 3.94 (1H, dd, H-17), 5.33 (1H, broad d, H-23), 5.62 (2H, m, H-18 and H-21), 6.89 (1H, d, H-25), 6.10 (1H, dd, H-19), 6.18 (1H, dd, H-20), 10.0 (1H, d, H-26).

Example 13

Acetylation of Sanglifehrin A to give 61-O-Acetyl-sanglifehrin A (Formula XXVI)

XXVI

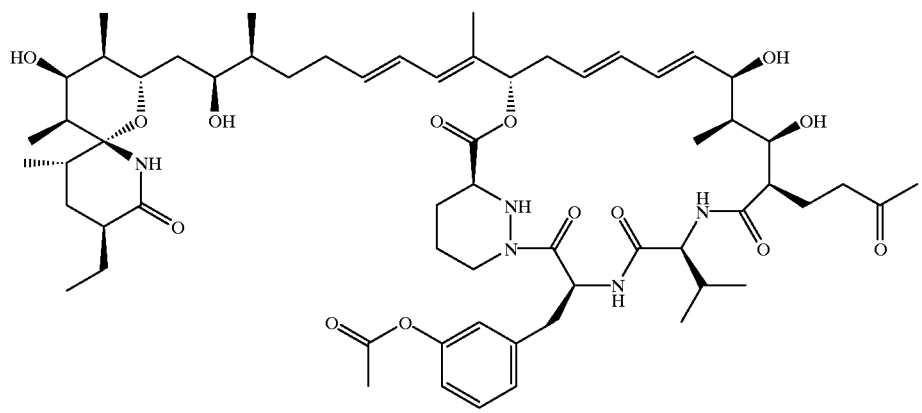

To a stirred, cooled (0° C.) solution of 54 mg (50 μmol) of sanglifehrin A and 50 μL of pyridine in 0.5 mL of methylene chloride is added 5.2 μL (55 μmol) of acetic anhydride. The reaction is kept at 0° C. for one hour, then allowed to warm to room temperature and stirring is continued for twelve hours. Saturated aqueous sodium bicarbonate is added and the resulting mixture is extracted with ethyl acetate. The organic layer is dried over anhydrous sodium sulfate, filtered and concentatred. The residue is purified by reverse phase chromatography (RP18, 40:60 acetonitrile-water to acetonitrile over 45 minutes) yielding the title compound as an amorphous powder.

MS m/z 1132 [M+H]$^+$ (rel. intensity 100); $^1$H NMR (DMSO) (only characteristic signals listed) δ1.68 (3H, s, H-49), 2.06 (3H, s, H-54), 2.25 (3H, s, CH$_3$CO$_2$), 4.04 (1H, d, C31-OH), 4.67 (1H, d, C2-NH), 4.76 (1H, d, C17-OH), 5.42 (2H, m, H-8 and C15-OH), 5.57 (3H, m, H-18, H-21 and C35-OH), 6.85 (1H, s, H-60), 6.98 (1H, d, H-62), 7.06 (1H, d, H-64), 7.31 (1H, dd, H-63), 7.51 (1H, d, H-12), 7.89 (1H, s, H-42), 8.23 (1H, d, H-9).

Example 14

Conversion of Sanglifehrin A into the ring-open compounds of Formula XXVII and XXVIII purified by silica gel chromatography (90:10 CH$_2$Cl$_2$:MeOH).

C$_6$H$_{95}$N$_5$O$_{14}$; MW=1122.46; MS:BT10/818/1:ML$^+$:1128.

20 mg of Sanglifehrin A is dissolved in 95 ml of THF and 100 μl of 1N NaOH is added. The resultant yellow solution is stirred at room temperature for 1 hour and left to stand at room temperature for 3 days. After washing and evaporation of solvent, the compound of formula XXVIII is purified by reverse phase chromatography (30:70 CH$_3$CN: H$_2$O-100 CH$_3$CN over 40 min). C$_{60}$H$_{93}$N$_5$O$_{14}$; MW=1108.44.

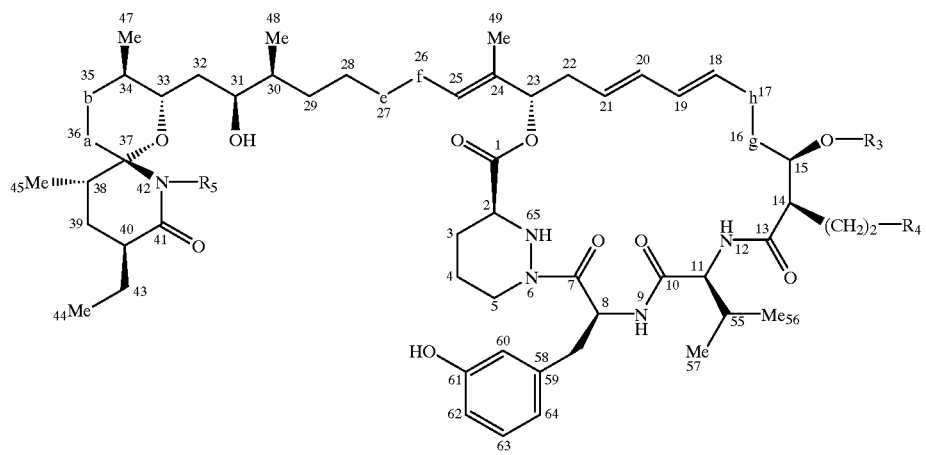

9. A macrolide according to claim 8 wherein the residue of formula X has the configuration
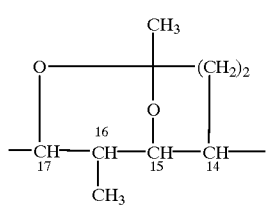
X
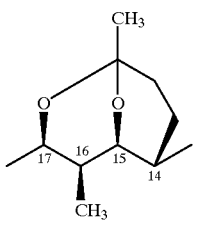

We claim:

1. A macrolide of formula VIII

S—L—M        VIII wherein

S represents a 1-oxo-7-aza-spiro-{5,5}-undecan-8-one-2-yl residue;

L represents a linker comprising a linear sequence of from 6 to 11 carbon atoms; and M represents a macrocyclic ring wherein positions 2 to 6 of said macrocyclic ring are provided by a substituted or unsubstituted piperidazinyl carboxylic acid residue of formula I

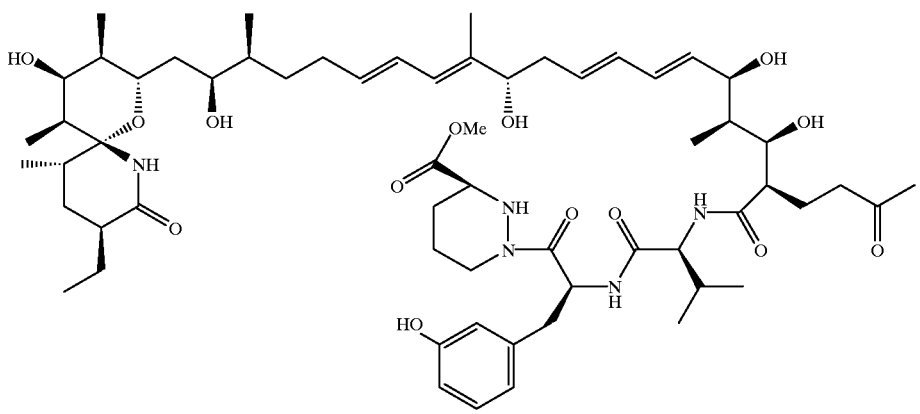

XXVII

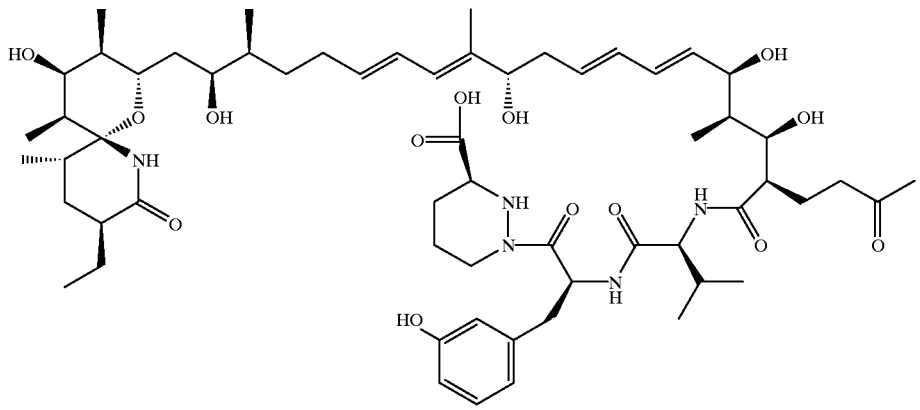

XXVIII 20 mg of Sanglifehrin A is dissolved in 0.5 ml of methanol and 3 mg of K$_2$CO$_3$. The resultant yellow coloured solution is stirred at room temperature for 1 hour, and then left to stand at room temperature for 3 days. After washing and evaporation of solvent, the compound of formula XXVII is

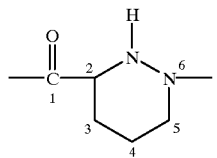

wherein the assigned numbers represent the position of the atoms of the residue in the macrocyclic ring, positions 7 to 9 of said macrocyclic ring are provided by an aromatic α-amino acid residue wherein the carboxy moiety of the aromatic α-amino acid residue occupies the 7-position of said macrocyclic ring, and the α-amino moiety of the aromatic α-amino acid residue occupies the 9-position of said macrocyclic ring, positions 10 to 12 of said macrocyclic ring are provided by an aliphatic α-amino acid residue wherein the carboxy moiety of the aliphatic α-amino acid residue occupies the 10-position of said macrocyclic ring and the α-amino moiety of the aliphatic a-amino acid residue occupies the 12-position of said macrocyclic ring, the remainder of the macrocyclic ring comprising a hydroxy carboxylic acid residue having a chain length of 6 to 20 carbon atoms, the oxy moiety of which completes a macrocyclic lactone linkage and the carbonyl moiety of which forms an amide linkage with the α-amino group at the 12-position of the macrocyclic ring, in free or protected form, or a salt thereof.

2. A macrolide according to claim 1 wherein the 1-oxo-7-aza-spiro-{5,5}-undecan-8-one-2-yl residue is of the formula

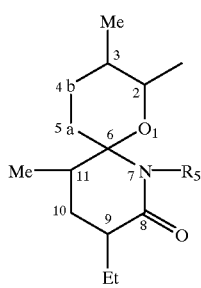

wherein —a—b— is —(Me)C=CH— or —(Me)CH—CH(OH)— and $R_5$ is H or Me.

3. A macrolide according to claim 1, in which the hydroxy carboxylic acid residue is a residue of formula II

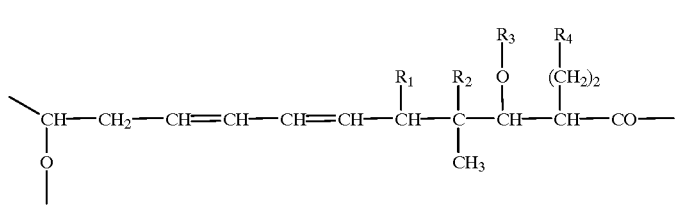

wherein $R_1$ is H, OH or represents an extra bond and $R_2$ is H or represents an extra bond;

$R_3$ is H;

$R_4$ is —CO—CH$_3$ or —CH(OH)—CH$_3$ or $R_3$ and $R_4$ together represent a structure of formula III

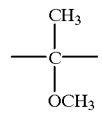

in free or protected form, or salt thereof.

4. A macrolide according to claim 1, in which the linker between the 1-oxo-7-aza-spiro-{5,5}-undecan-8-one-2-yl residue and the macrolide ring is a group of formula VII

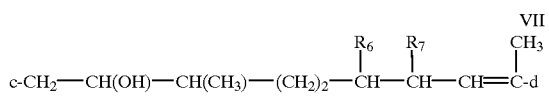

wherein c represents linkage to the 1-oxo-7-aza-spiro-{5,5}-undecan-8-one-2-yl residue;

d represents linkage to the macrocyclic ring and $R_6$ and $R_7$ are each OH or together represent an additional bond, in free or protected form.

5. A compound according to claim 1 of formula IX

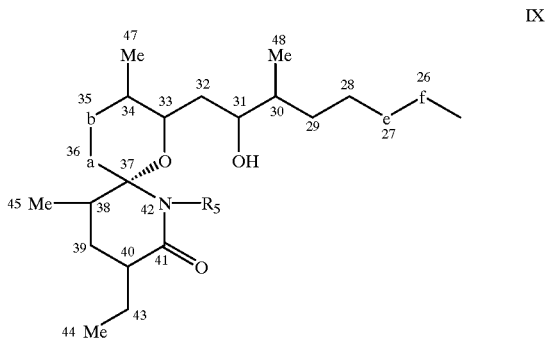

-continued

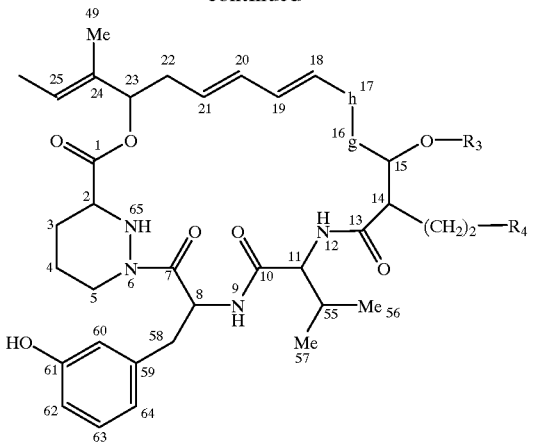

wherein
—a—b— is —(Me)C=CH— or —(Me)CH—CH(OH)—;
—e—f— is —CH(OH)—CH(OH)— or —CH=CH—;
—g—h— is as defined above for —a—b—, and $R_3$ is H;
$R_4$ is —CO—CH$_3$ or —CH(OH)—CH$_3$ or $R_3$ and $R_4$ together represent a structure of formula III

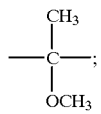

and $R_5$ is H or Me; in free or protected form or salt thereof.

6. A compound according to claim 5 having the following conformation wherein when —a—b— is —(Me)CH—CH(OH)—, it has the configuration:

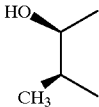

when —e—f— is —CH(OH)—CH(OH)—, it has the (S),(S) configuration or the (R),(R) configuration;
when —g—h—is —(Me)CH—CH(OH)—, it has the configuration:

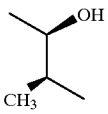

when —g—h— is —(Me)C=CH—, it has the configuration:

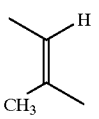

and when $R_3$ and $R_4$ are fused together they are is of configuration

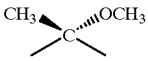

7. A Sanglifehrin selected from the group consisting of Sanglifehrin A, B, C and D.

8. A macrolide according to claim 1 in protected form wherein the 14 to 17 positions of the macrocyclic ring comprise a residue of formula X: